(12) United States Patent
Kirk et al.

(10) Patent No.: US 12,036,283 B2
(45) Date of Patent: Jul. 16, 2024

(54) LONG-ACTING INTERLEUKIN-15 RECEPTOR AGONISTS AND RELATED IMMUNOTHERAPEUTIC COMPOSITIONS AND METHODS

(71) Applicant: Nektar Therapeutics, San Francisco, CA (US)

(72) Inventors: Peter Benedict Kirk, Oxfordshire (GB); Ping Zhang, Millbrae, CA (US); Peiwen Kuo Brewer, San Carlos, CA (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 16/613,757

(22) PCT Filed: May 15, 2018

(86) PCT No.: PCT/US2018/032817
§ 371 (c)(1),
(2) Date: Nov. 14, 2019

(87) PCT Pub. No.: WO2018/213341
PCT Pub. Date: Nov. 22, 2018

(65) Prior Publication Data
US 2020/0078467 A1 Mar. 12, 2020

Related U.S. Application Data

(60) Provisional application No. 62/648,240, filed on Mar. 26, 2018, provisional application No. 62/582,186, filed on Nov. 6, 2017, provisional application No. 62/536,966, filed on Jul. 25, 2017, provisional application No. 62/506,494, filed on May 15, 2017.

(51) Int. Cl.
*C07K 16/24* (2006.01)
*A61K 38/20* (2006.01)
*A61K 47/60* (2017.01)
*A61P 35/04* (2006.01)

(52) U.S. Cl.
CPC .......... *A61K 47/60* (2017.08); *A61K 38/2086* (2013.01); *A61P 35/04* (2018.01)

(58) Field of Classification Search
None
See application file for complete search history.

(56) References Cited

U.S. PATENT DOCUMENTS

| | | |
|---|---|---|
| 5,739,208 A | 4/1998 | Harris |
| 5,795,966 A | 8/1998 | Grabstein et al. |
| 5,932,462 A | 8/1999 | Harris et al. |
| 6,110,721 A | 8/2000 | Gibbs et al. |
| 6,177,079 B1 | 1/2001 | Grabstein et al. |
| 2004/0204548 A1 | 10/2004 | Kozlowski et al. |
| 2004/0253587 A1 | 12/2004 | Grabstein et al. |
| 2005/0014903 A1 | 1/2005 | Kozlowski et al. |
| 2005/0095223 A1 | 5/2005 | Sivakumar et al. |
| 2006/0057102 A1 | 3/2006 | Zheng et al. |
| 2006/0104945 A1 | 5/2006 | Choi |
| 2006/0257361 A1 | 11/2006 | Watanabe et al. |
| 2006/0293499 A1 | 12/2006 | Bentley et al. |
| 2010/0112607 A1 | 5/2010 | Varadi et al. |
| 2015/0017120 A1 | 1/2015 | Wittrup et al. |
| 2016/0022828 A1 | 1/2016 | Bossard et al. |
| 2017/0035898 A1 | 2/2017 | Liu et al. |

FOREIGN PATENT DOCUMENTS

| | | | |
|---|---|---|---|
| CN | 102145178 B | 9/2012 | |
| EP | 0 772 624 B1 | 9/2000 | |
| WO | WO 90/12874 A2 | 11/1990 | |
| WO | WO 99/45964 A1 | 9/1999 | |
| WO | WO 01/62827 A2 | 8/2001 | |
| WO | WO 2004/060300 A2 | 7/2004 | |
| WO | WO 2008/106186 A2 | 9/2008 | |
| WO | WO 2009/095479 A2 | 8/2009 | |
| WO | WO 2012/016131 A1 | 2/2012 | |
| WO | WO 2012/065086 A1 | 5/2012 | |
| WO | WO 2013/020079 A2 | 2/2013 | |
| WO | WO 2015/153753 A2 | 10/2015 | |
| WO | WO-2015153753 A2 * | 10/2015 | ......... A61K 38/2086 |
| WO | WO 2016/060996 A2 | 4/2016 | |
| WO | WO 2017/062832 A1 | 4/2017 | |

OTHER PUBLICATIONS

Riedinger et al. "Ratiometric Optical Sensing of Chloride Ions with Organic Fluorophore-Gold Nanoparticle Hybrids: A Systematic Study of Design Parameters and Surface Charge Effects"; small 2010, 6, No. 22, 2590-2597. (Year: 2010).*
Nellis et al. "Characterization of Recombinant Human IL-15 Deamidation and Its Practical Elimination through Substitution of Asparagine 77"; Pharm Res (2012) 29:722-738 (Year: 2012).*
Structural Isomerism in Organic Molecules. (Sep. 13, 2020). Truro School in Cornwall https://chem.libretexts.org/@go/page/3650 (Year: 2020).*
Pfister and Morbidelli. Process for protein PEGylation. Journal of Controlled Release 180 (2014) 134-149 (Year: 2014).*
Berge et al., "Pharmaceutical Salts", Journal of Pharmaceutical Sciences, vol. 66, No. 1, pp. 1-19, (Jan. 1977).
Chiossone et al., "Maturation of mouse NK cells is a 4-stage development program", Blood, vol. 113, No. 22, pp. 5488-5496, (May 28, 2009).
Di Sabatino et al., "Role of IL-15 in immune-mediated and infectious diseases", Cytokine & Growth Factor Reviews, vol. 22, pp. 19-33, (2011).

(Continued)

Primary Examiner — Michael D Pak
(74) Attorney, Agent, or Firm — Jacqueline F. Mahoney; Susan T. Evans

(57) ABSTRACT

The instant disclosure provides a long acting IL-15 receptor agonist, related compositions and methods of preparation and use, for example, in the treatment of conditions responsive to therapy effective to provide, for example, sustained immune activation and/or anti-tumor activity.

28 Claims, 48 Drawing Sheets
Specification includes a Sequence Listing.

(56) References Cited

OTHER PUBLICATIONS

Fischer et al., "Recombinant human acetylcholinesterase expressed in *Escherichia coli*: refolding, purification and characterization", Biotechnol. Appl. Biochem., vol. 21, pp. 295-311, (1995).
Giri et al., "Identification and cloning of a novel IL-15 binding protein that is structurally related to the α chain of the IL-2 receptor", The EMBO Journal, vol. 14, No. 15, pp. 3654-3663, (1995).
Grabstein et al., "Cloning of a T cell Growth Factor That Interacts with the β Chain of the Interleukin-2 Receptor", Science, vol. 264, pp. 965-968, (May 13, 1994).
Hayakawa et al., "CD27 Dissects Mature NK Cells into Two Subsets with Distinct Responsiveness and Migratory Capacity", The Journal of Immunology, vol. 176, pp. 1517-1524, (2006).
Kronman et al., "Production and secretion of high levels of recombinant human acetylcholinesterase in cultured cell lines: microheterogeneity of the catalytic subunit", Gene, vol. 121, pp. 295-304, (1992).
Mor et al., "Expression of Recombinant Human Acetylcholinesterase in Transgenic Tomato Plants", Biotechnol, Bioeng., vol. 75, ppl. 259-266, (2001).
Morel et al., "Expression and processing of vertebrate acetylcholinesterase in the yeast *Pichia pastoris*", Biochem. J., vol. 328, pp. 121-129, (1997).
Nair et al., "A simple practice guide for dose conversion between animals and human", J. Basic Clin. Pharma., vol. 7, pp. 27-31, (2016).
Pettit et al., "Structure-Function Studies of Interleukin 15 using Site-specific Mutagenesis, Polyethylene Glycol Conjugation, and Homology Modeling", The Journal of Biological Chemistry, vol. 272, No. 4, pp. 2312-2318, (Issue of Jan. 24, 1997).
Ring et al., "Mechanistic and structural insight into the functional dichotomy between interleukin-2 and interleukin-15", Nat. Immunol., vol. 13, No. 12, pp. 1187-1195, (Dec. 2012).
Sims et al., "A Method for the Estimation of Polyethylene Glycol in Plasma Protein Fractions", Analytical Biochemistry, vol. 107, pp. 60-63, (1980).
Steel et al., "Interleukin-15 biology and its therapeutic implications in cancer", Trends Pharmacol. Sci., vol. 33, No. 1, pp. 35-41, (Jan. 2012).
Wong et al., "The IL-15-based superagonist ALT-803 promotes the antigen-independent conversion of memory CD8+ T cells into innate-like effector cells with antitumor activity", OncoImmunology, vol. 2, No. 11, pp. e26442-1-e26442-3, (Nov. 2013).
International Search Report and the Written Opinion corresponding to PCT Application No. PCT/US2018/032817 date of mailing Aug. 9, 2018.
International Preliminary Report on Patentability corresponding to PCT Application No. PCT/US2018/032817 date of mailing Nov. 28, 2019.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003-1$^{st}$, (Jan. 2003).
NOF Corporation, PEG Derivatives, Phospholipid and Drug Delivery Materials for Pharmaceuticals, 27 pages, Catalogue 2003-2$^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
Bailon et al., "PEG-modified biopharmaceuticals", Expert Opinion Drug Delivery, vol. 6, No. 1, pp. 1-16, (2009).
Heldt et al., "The Use of Glycidol to Introduce Aldehyde Functions Into Proteins—Applications to the Fluorescent Labelling of Bovine Serum Albumin and Avidin", Eur. J. Org. Chem., pp. 5429-5433, (2007).
Luchansky et al., "Metabolic Functionalization of Recombinant Glycoproteins", Biochemistry, vol. 43, pp. 12358-12366, (2004).
Ouchi et al., "Design of Antitumor Agent-Terminated Poly(Ethylene Glycol) Conjugate as Macromolecular Prodrug", Polymer Preprints, vol. 38, No. 1, pp. 582-583, (1997).
Pettit et al., "Polyethylene Glycol Conjugation to Lysine Residues of Recombinant IL-15 Generates a Specific IL-15 Antagonist", Proceed. Intern. Symp. Control Rel. Bioact. Mater, vol. 22, pp. 496-497, (1995).
Roberts et al., "Chemistry for peptide and protein PEGylation", Advanced Drug Delivery Reviews, vol. 54, pp. 459-476, (2002).
Zalipsky, "Chemistry of polyethylene glycol conjugates with biologically active molecules", Advanced Drug Delivery Reviews, vol. 16, pp. 157-182, (1995).
Zalipsky et al., "Use of Functionalized Poly(Ethylene Glycol)s for Modification of Polypeptides", Poly(Ethylene Glycol) Chemistry: Biotechnical and Biomedical Applications, edited by J. Milton Harris, Plenum Press, New York, pp. 347-370, (1992).
PCT International Search Report and Written Opinion corresponding to PCT Application No. PCT/US2015/023871 date of mailing Jul. 20, 2015.
PCT International Preliminary Report on Patentability corresponding to PCT Application No. PCT/US2015/023871 date of mailing Oct. 13, 2016.
European Extended Search Report corresponding to European Patent Application No. 18803095.1-1109 dated Jan. 29, 2021.
"IL-15 Gene" accessed on Jul. 2, 2018 at https://www.genecards.org/cgi-bin/carddisp.pl?gene=IL15.
Australian Examination Report No. 1 corresponding to Australian Patent Application No. 2018270926 date of report Jul. 27, 2021.
English Translation of the Eurasian Official Action corresponding to Eurasian Patent Application No. 201992716 dated Feb. 20, 2021.
English Translation of the Eurasian Official Action corresponding to Eurasian Patent Application No. 201992716 dated Mar. 3, 2022.
English Translation of the Israeli Official Action corresponding to Israel Patent Application No. 270634 dated May 12, 2022.
English Translation of the Japanese Notice of Reasons for Rejection corresponding to Japanese Patent Application No. 2019-563255 dated Feb. 21, 2022.

(56) References Cited

OTHER PUBLICATIONS

English Translation of Notice of Final Rejection corresponding to Japanese Patent Application No. 2019-563255 mailing date Dec. 9, 2022.

Burkett et al., "IL-15Rα expression on CD8+ T cells is dispensable for T cell memory", PNAS, vol. 100, No. 8, pp. 4724-4729, (Apr. 15, 2003).

Marcais et al., "Regulation of mouse NK cell development and function by cytokines", Frontiers in Immunology, vol. 4, Article 450, pp. 1-14, (Dec. 12, 2013).

Patidar et al., "Interleukin 15: A key cytokine for immunotherapy", Cytokine & Growth Factor Reviews, vol. 31, pp. 49-59, (2016).

Robinson et al., "The potential and promise of IL-15 in immuno-oncogenic therapies", Immunology Letters, vol. 190, pp. 159-168, (2017).

Schluns et al., "Transregulation of memory CD8 T-cell proliferation by IL-15 Rα+ bone marrow-derived cells", Blood, vol. 103, No. 3, pp. 988-994, (Feb. 1, 2004).

Stonier et al., "Trans-presentation: a novel mechanism regulating IL-15 delivery and responses", Immunol. Lett., vol. 127, No. 2, pp. 85-92, (Jan. 4, 2010).

Van Den Bergh et al., "IL-15 receptor alpha as the magic wand to boost the success of IL-15 antitumor therapies: The upswing of IL-15 transpresentation", Pharmacology & Therapeutics, vol. 170, pp. 73-79, (2017).

Australian Examination Report No. 1 corresponding to Australian Patent Application No. 2022203691 date of report Feb. 13, 2023.

Canadian Office Communication corresponding to Canadian Patent Application No. 3,060,410, dated Nov. 30, 2023.

English translation of Chinese Notification of the First Office Action corresponding to Chinese Patent Application No. 201880032373.3 date of notification Feb. 27, 2023.

English translation of Chinese Notification of Second Office Action corresponding to Chinese Patent Application No. 201880032373.3 date of notification Jan. 26, 2024.

English translation of Eurasian Office Action corresponding to Eurasian Patent Application No. 202390881 dated Apr. 13, 2023.

English translation of Israeli Office Communication corresponding to Israeli Patent Application No. 270,634 date of notification Jul. 12, 2023.

English translation of Korean Notice of Grounds for Rejection corresponding to Korean Patent Application No. 10-2019-7036787 issuance date Sep. 15, 2023.

English translation of Mexican Office Action corresponding to Mexican Patent Application No. MX/a/2019/013621 date of notification Jan. 16, 2024.

* cited by examiner

SEQ ID NO:1

```
         10          20          30          40          50          60
MNWVNVISDL KKIEDLIQSM HIDATLYTES DVHPSCKVTA MKCFLLELQV ISLESGDASI 70          80          90         100         110
HDTVENLIIL ANNSLSSNGN VTESGCKECE ELEEKNIKEF LQSFVHIVQM FINTS
```

1: Mark12; 2: IL-15;
3: mono-mPEG-sba40k-IL-15;

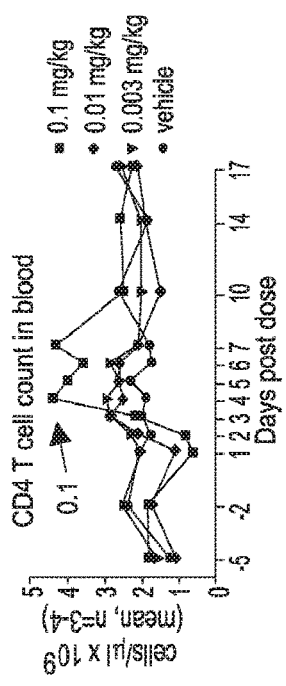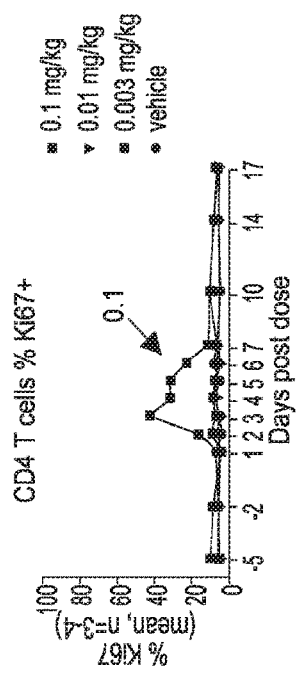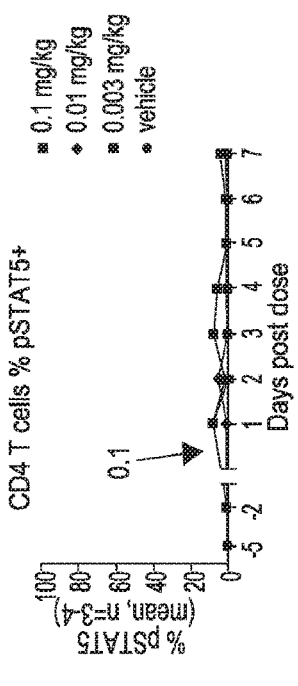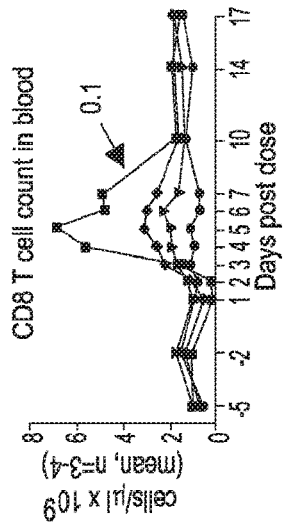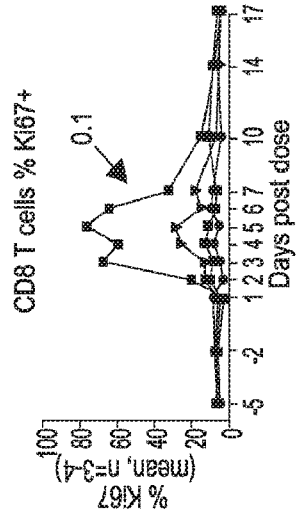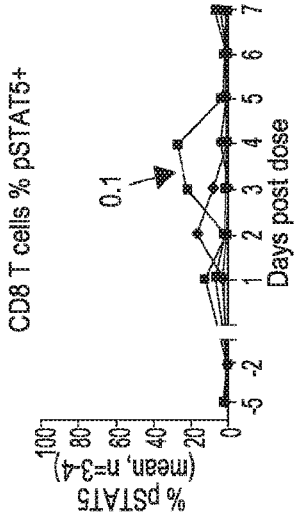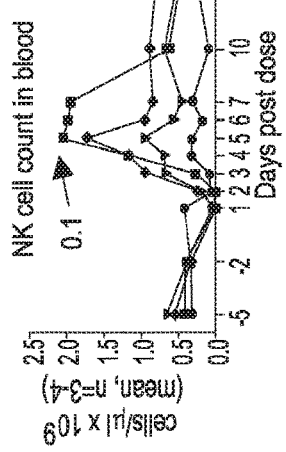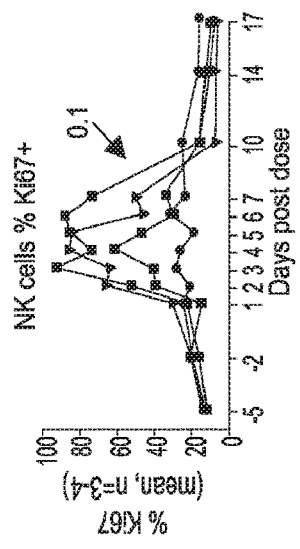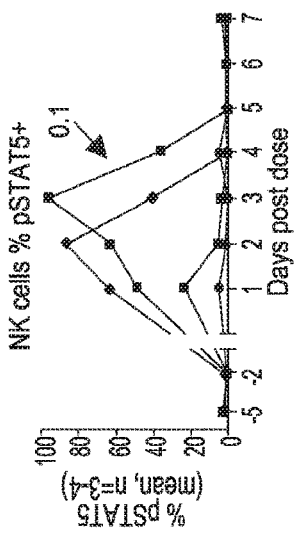

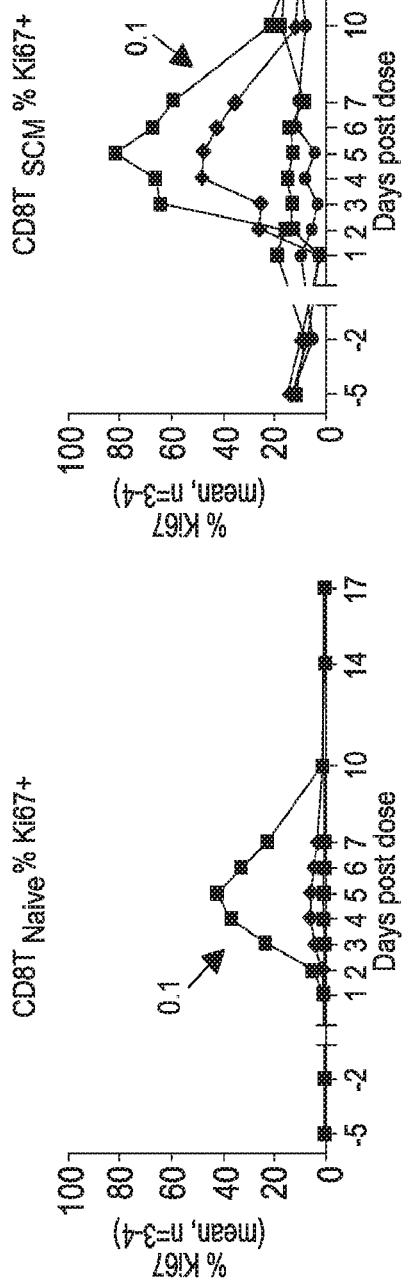
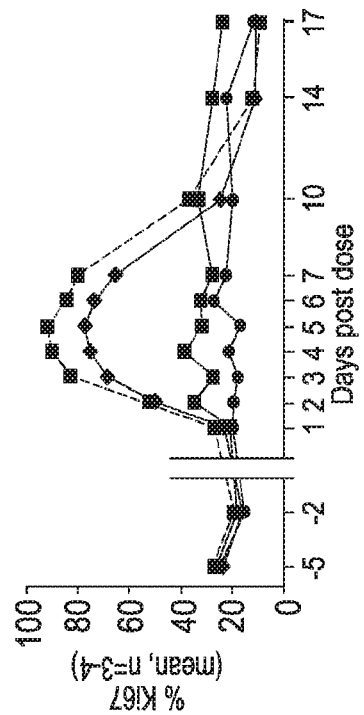
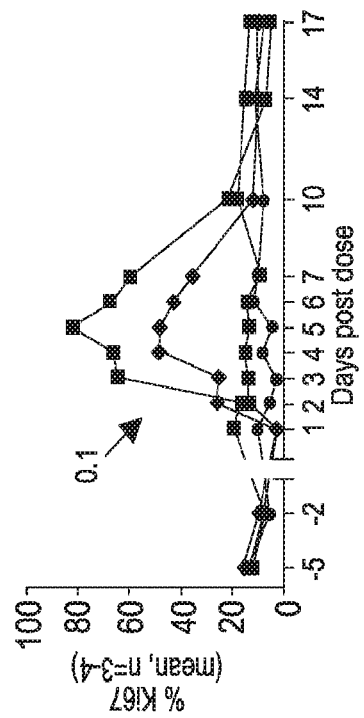
FIG. 47A, FIG. 47B, FIG. 47C, FIG. 47D

SEQUENCE LISTING

<160> NUMBER OF SEQ ID NOS: 3

<210> SEQ ID NO 1
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Asn Trp Val Asn Val Ile Ser Asp Leu Lys Lys Ile Glu Asp Leu Ile
1               5                   10                  15

```
Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 2
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Asn Trp Val Asn Val Ile Ser Asp Leu Lys Lys Ile Glu Asp Leu
 1               5                  10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
            35                  40                  45

Gln Val Ile Ser Leu Glu Ser Gly Asp Ala Ser Ile His Asp Thr Val
 50                  55                  60

Glu Asn Leu Ile Ile Leu Ala Asn Asn Ser Leu Ser Ser Asn Gly Asn
 65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 3
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Arg Ile Ser Lys Pro His Leu Arg Ser Ile Ser Ile Gln Cys Tyr
 1               5                  10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
 50                  55                  60

Gln Ser Met His Ile Asp Ala Thr Leu Tyr Thr Glu Ser Asp Val His
```

```
                65                  70                  75                  80
Pro Ser Cys Lys Val Thr Ala Met Lys Cys Phe Leu Leu Glu Leu Gln
                        85                  90                  95

Val Ile Ser Leu Glu Ser Gly Asp Ala Ser Ile His Asp Thr Val Glu
                100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
        130                 135                 140

Lys Glu Phe Leu Gln Ser Phe Val His Ile Val Gln Met Phe Ile Asn
145                 150                 155                 160

Thr Ser
```

LONG-ACTING INTERLEUKIN-15 RECEPTOR AGONISTS AND RELATED IMMUNOTHERAPEUTIC COMPOSITIONS AND METHODS

CROSS REFERENCE TO RELATED APPLICATIONS

This application is a 35 U.S.C. § 371 application of International Application No. PCT/US2018/032817 filed May 15, 2018, designating the United States, which claims the benefit of priority under 35 U.S.C. 119(e) to U.S. Provisional Patent Application No. 62/506,494, filed on May 15, 2017; and to U.S. Provisional Patent Application No. 62/536,966, filed Jul. 25, 2017; and to U.S. Provisional Patent Application No. 62/582,186, filed Nov. 6, 2017; and to U.S. Provisional Patent Application No. 62/648,240, filed Mar. 26, 2018, the disclosures of which are each incorporated herein by reference in their entireties.

REFERENCE TO A SEQUENCE LISTING SUBMITTED VIA EFS-WEB

The contents of the ASCII text file of the sequence listing named, "SHE0546_00_SL.txt", having a size of 4,299 bytes, created Nov. 14, 2019 and filed via EFS-WEB on the same date, is incorporated herein by reference in its entirety.

FIELD

The instant disclosure is directed to (among other things) a long acting interleukin-15 ("IL-15") receptor agonist, related compositions and methods of preparation and use, for example, in the treatment of conditions responsive to therapy effective to provide, for example, sustained immune activation and anti-tumor activity.

BACKGROUND

Interleukin-15 ("IL-15") is a pleiotropic cytokine that was first reported by Grabstein et al. (Grabstein et al. (1994) *Science* 264:965-968). Secreted as a 162-amino acid precursor, human IL-15 contains a 29-amino acid leader sequence and a 19-amino acid pro sequence; the mature protein is therefore 114 amino acids in length. Belonging to the four α-helix bundle family of cytokines, IL-15 binds to a heterotrimeric receptor, wherein a unique a subunit (IL-15Rα) confers receptor specificity to IL-15, and the β and γ subunits of this receptor share commonality with one or more other cytokine receptors. Giri et al. (1995) *EMBO J.* 14:3654-3663.

As a cytokine, IL-15 has effects on both the innate immune system and the adaptive immune system (DiSabitino et al. (2011) *Cytokine Growth Factor Rev.* 22:19-33). With respect to the innate immune system (which defends the host from foreign invaders generically), IL-15 causes the development of and maintains the survival of natural killer cells ("NK cells") and natural killer-T cells ("NK-T cells"), in addition to having other properties. Consistent with their role in the innate immune system, NK cells do not specifically attack the invading pathogen, rather, these cells destroy compromised host cells (such as tumor cells or virus-infected cells). NK-T cells generate immunomodulatory cytokines, particularly interferon-γ, which result in a general activation of the immune response.

With respect to the adaptive immune system (which defends the host from a specific foreign invader following an initial encounter with that particular pathogen), IL-15 is necessary for the maintenance of the immunomodulatory cytokine-generating helper T cells. Importantly, IL-15 also supports the long-term maintenance of "antigen-experienced" memory T cells, which have the ability to rapidly reproduce, thereby generating a faster and stronger immune response upon re-exposure to the particular foreign pathogen invading the host.

Finally, notwithstanding its specific roles within both the innate and adaptive immune systems, IL-15 has significant and broad effects across both categories of immune systems. In particular, IL-15 inhibits or reduces apoptosis (or cell death) of a number of cells types (including dendritic cells, neutrophils, eosinophils, mast cells, CD4+ T cells, and B cells) associated within both categories of immune systems.

Because it stimulates the proliferation and maintenance of many cells within the immune system that can fight against cells that appear to the host as foreign (or "non-self"), IL-15 has been proposed for use in the treatments of individuals suffering from cancer (Steel et al. (2012) *Trends Pharmacol. Sci.* 33(1):35-41). For example, an IL-15-based agonist has been proposed to treat myelomas (Wong et al. (2013) *OncoImmunology* 2(11), e26442:1-3). In addition, IL-15 pharmacotherapy has been proposed for treating individuals suffering from viral infections, such as HIV infection.

Despite its potential for use in the treatment of individuals suffering from a number of diseases, IL-15-based therapies face a number of challenges. For example, IL-15 is rapidly cleared from plasma and is relatively unstable under physiological conditions. Moreover, in vivo signaling activity of IL-15 is similarly short-lived, and the molecule unfavorably requires daily dosing or multi-day continuous infusion for optimal activity. Certain approaches attempt to overcome these limitations by complexing IL-15 with the IL-15 receptor alpha subunit. Such an approach, however, may abrogate the desirable signaling that occurs uniquely through the IL-15 receptor alpha, expressed on multiple cell types. A non-releasable PEGylation with a succinimidyl carbonate-terminated polymer of relatively small molecular weight (5 kDa) has been reported, but this resulted in significant alteration of IL-15's biological activity. Pettit et al. (1997) *J. Biol. Chem.* 272(4):2312-2318.

Notwithstanding the foregoing approaches, however, there remains a need for new IL-15 receptor agonists having improved characteristics and profiles, such as, for example, potent immune stimulatory effects, low systemic toxicity, stability and/or improved pharmacokinetics. Thus, among other things, the instant disclosure provides a long-acting IL-15 receptor agonist having a number of advantageous features to be described in greater detail below, as well as compositions and kits comprising such agonist, as well as related methods of preparation and use, as described herein, which are believed to be new and completely unsuggested by the art.

SUMMARY

In a first aspect, provided herein is a long acting IL-15 receptor agonist including pharmaceutically acceptable salt forms thereof. The long acting IL-15 receptor (IL-15 agonist comprises at least a single linear PEG (polyethylene glycol) moiety stably covalently attached to an IL-15 amino group via an amide linkage. Intervening between the linear PEG strand and the stable amide linkage to an IL-15 amino group may be a linear unsubstituted alkylene group $(\sim CH_2 \sim)_m$ having from 2 to 5 carbon atoms (i.e., m=2, 3, 4, or 5).

For example, in some embodiments, the unsubstituted alkylene group is (~CH$_2$~)$_2$; or, in some additional embodiments, the unsubstituted alkylene group is (~CH$_2$~)$_3$; in yet some further embodiments, the unsubstituted alkylene group is (~CH$_2$~)$_4$; in yet some further embodiments, the unsubstituted alkylene group is (~CH$_2$~)$_5$.

For example, in some embodiments, the long acting IL-15 receptor agonist has the following structure:

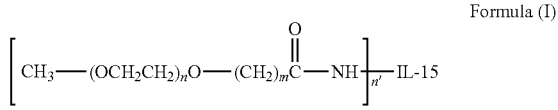

Formula (I)

wherein IL-15 is an interleukin-15 moiety, n is an integer from about 150 to about 3,000; m is an integer from 2-5 (e.g., 2, 3, 4, or 5) and n' is 1. Formula (I) may also be depicted as [CH$_3$O—(CH$_2$CH$_2$O)$_n$(CH$_2$)$_m$C(O)—NH—]$_{n'}$—IL15, and the two formulae may be used interchangeably. In Formula I (and in similar formulae provided herein) the ~NH~ in the structure represents an amino group of the IL-15 moiety.

In some further embodiments, n is an integer from about 200 to about 2000, or from about 400 to about 1300, or from about 450 to about 1200.

In yet one or more additional embodiments, m is 2 or 3, such that the linear alkylene group separating the PEG moiety from the stable amide linkage to IL-15 is either ~(CH$_2$)$_2$~ or (CH$_2$)$_3$~. In some preferred embodiments, m is 3.

In one or more embodiments, n is an integer having a value that corresponds to a polyethylene glycol polymer having a weight average molecular weight selected from the group consisting of 10,000 daltons (e.g., n is ~227), 15,000 daltons (e.g., n is ~340), 20,000 daltons (e.g., n is ~454), 25,000 daltons (e.g., n is ~568), 30,000 daltons (e.g., n is ~681), 40,000 daltons (e.g., n is ~909), 50,000 daltons (e.g., n is ~1136) and 60,000 daltons (e.g., n is ~1364).

In one or more illustrative embodiments, provided is a composition comprising a long acting IL-15 receptor agonist in accordance with Formula (I), including without limitation each and every one of its related embodiments as provided herein.

In some embodiments, the long acting IL-15 receptor agonist composition comprises no more than about 15 mole percent of long-acting IL-15 receptor agonists, when considered collectively, encompassed by the formula:

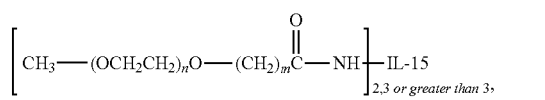

Formula (II)

where the values of n and m are as provided for Formula (I) above. That is to say, in terms of the long-acting IL-15 receptor agonist component of such compositions, no more than about 15 mol percent of long-acting IL-15 receptor agonists comprised in the composition are of Formula (II).

For example, in some embodiments, the long acting IL-15 receptor agonist composition comprises no more than about 10 mole percent of long-acting IL-15 receptor agonists, that when considered collectively, are encompassed by Formula (II).

In some additional embodiments of the foregoing, the composition comprises no more than about 7 mole percent of long acting IL-15 receptor agonists having n' equal to 2, 3, or greater than 3 (i.e., higher PEGmers, also referred to as "high-mers"). In yet some other embodiments, the composition comprises no more than about 5 mole percent, 6 mole percent, 9 mole percent or 10 mole percent of long acting IL-15 receptor agonists having n' equal to 2, 3 or greater than 3 (i.e., of 2 or greater).

In some further embodiments, the composition comprises a long-acting IL-15 receptor agonist according to Formula (I),

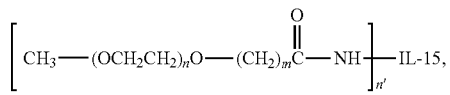

where n and m are as described above, and n' represents the average number of polyethylene glycol moieties covalently attached to IL-15 amino groups (for the composition), and n' for the composition is in a range from 1.0 to about 1.3. For example, the average number of polyethylene glycol moieties per IL-15 moiety is selected from about 1.0, 1.1, 1.2 and about 1.3.

In yet another aspect, provided herein is a method of preparing a long acting interleukin-15 receptor agonist such as described in Formula (I), e.g., Formulae (Ia), (Ib), (Ic), (Id), and in Formula (II), e.g., (IIa), (IIb), (IIc), and (IId). In the method, interleukin-15 (generally dissolved in a buffer such as phosphate buffered saline or any other suitable buffer, at a pH of around 7 (e.g., 7.0, 7.1, 7.2, 7.3, 7.4, 7.5, 7.6), is reacted with an activated PEG reagent, such as a methoxyPEG-succinimidyl alkanoate (where n is an integer from about 150 to about 3,000) according to the following structure:

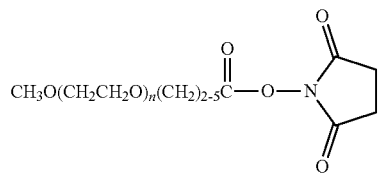

for a period of time sufficient to form,

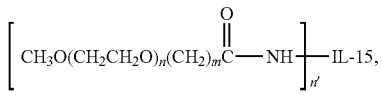

where n' is 1. Exemplary methoxyPEG-succinimidyl alkanoate reagents for reacting with interleukin-15 include the following:

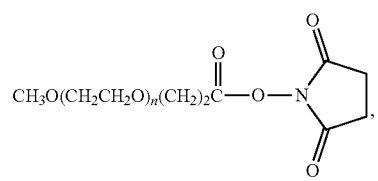

-continued

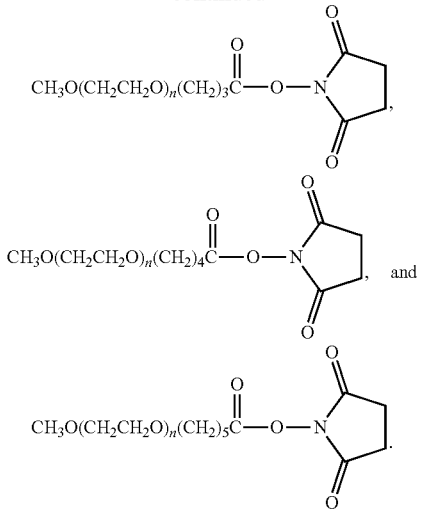

In some preferred embodiments, the methoxyPEG-succinimidyl alkanoate reagent is

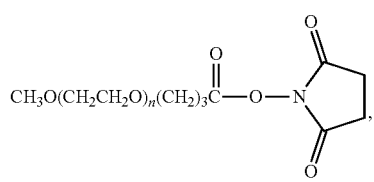

mPEG-succinimidyl butanoate.

In some embodiments, the methoxyPEG-succinimidyl alkanoate reagent has a weight average molecular weight selected from the group consisting of about 10,000 daltons (e.g., n is ~227), about 15,000 daltons (e.g., n is ~340), about 20,000 daltons (e.g., n is ~454), about 25,000 daltons (e.g., n is ~568), about 30,000 daltons (e.g., n is ~681), about 40,000 daltons (e.g., n is ~909), about 50,000 daltons (e.g., n is ~1136) and about 60,000 daltons (e.g., n is ~1364).

In one or more embodiments of the method, the methoxyPEG-succinimidyl alkanoate reagent is added in an equimolar amount (i.e., equimolar ratio) to interleukin-15.

In one or more alternative embodiments, the methoxyPEG-succinimidyl alkanoate reagent is added in a molar excess of interleukin-15. In some particular embodiments, the methoxyPEG-succinimidyl alkanoate reagent is present in a 2-fold molar excess, or a 5-fold molar excess, or a 7-fold molar excess, or a ten-fold molar excess, or even a 12-fold molar excess or more. In some embodiments, the methoxyPEG-succinimidyl alkanoate reagent is added at a 5 to 10-fold molar excess.

In some embodiments, the methoxyPEG-succinimidyl alkanoate reagent is added as a solid.

In some other embodiments, the methoxyPEG-succinimidyl alkanoate reagent is dissolved in a suitable solvent. In a particular embodiment, the methoxyPEG-succinimidyl alkanoate reagent is dissolved in an aqueous acid, such as, for example, dilute hydrochloric acid, although any suitable acid may be employed.

In some further embodiments of the method, the interleukin-15 is initially present in solution, i.e., prior to mixing with the methoxyPEG-succinimidyl alkanoate reagent, at a concentration of about 0.5 mg/mL to about 10 mg/mL.

Additional illustrative concentration ranges include, for example, from about 0.5 mg/mL to about 5 mg/mL interleukin-15, from about 0.5 mg/mL to about 3 mg/mL, and from about 1.0 mg/mL to about 4 mg/mL interleukin-15.

In some further embodiments, the pH of the interleukin-15 solution is adjusted to about 8.0 prior to addition of the methoxyPEG-succinimidyl alkanoate reagent.

In some further embodiments, the pH of the reaction mixture is adjusted to about 8.0 following addition of the methoxyPEG-succinimidyl alkanoate reagent.

In some further embodiments, the resulting reaction mixture is stirred (or mixed) for a period of time sufficient to allow reaction between the reactants. In some embodiments, the reactants are mixed for up and including from about 15 minutes to about 10 hours. In some further embodiments, the reactants are mixed from about 30 minutes to about 5 hours, or from about 30 minutes to about 2 hours.

In some embodiments, the reaction is carried out under ambient conditions, e.g., at room temperature, i.e., absent the addition of heat. Illustrative temperatures ranges for carrying out the reaction include, for example, from about 5° C. to about 50° C., or from about 10° C. to about 40° C., or from about 15° C. to about 30° C. In some further embodiments, the reaction is carried out at a temperature from about 20° C. to about 25° C.

In some embodiments of the method, the reaction is quenched by addition of an amino acid. In some related embodiments, the reaction is quenched by addition of glycine.

In some further embodiments of the method, conjugation products, i.e., methoxyPEG-alkanoate-interleukin-15 conjugates, are separated from the reaction mixture.

In some additional embodiments, the reaction mixture comprising methoxyPEG-alkanoate-interleukin-15 conjugates is purified.

In some particular embodiments, the reaction results in formation of

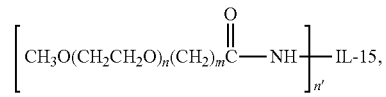

where n' is 1.

In some further embodiments, the reaction is effective to form a composition comprising no more than about 15 mole percent (mol %) of long-acting IL-15 receptor agonists (of the IL-15 containing molecules in the composition), when considered collectively, encompassed by the formula:

Formula (II)

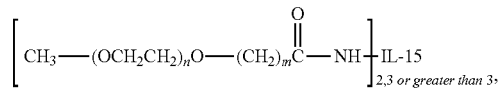

where the values of n and m are as provided for Formula (I) above.

In yet some additional embodiments, the reaction is effective to product PEGylated interleukin-15 that is less than 20-35% or less than about 25% deamidated.

In some embodiments, the long-acting IL-15 receptor agonist exhibits no more than about a 7-fold reduction in EC50 value (ng/mL, CTLL-2 pSTAT5) when compared to unmodified (i.e., unconjugated) IL-15. For example, in one or more related embodiments, the long-acting IL-15 receptor agonist exhibits no more than about a 6.5-fold reduction in EC50 value (ng/mL, CTLL-2 pSTAT5), or no more than about a 6-fold reduction in EC50 value (ng/mL, CTLL-2 pSTAT5), or no more than about a 5.5-fold reduction in EC50 value (ng/mL, CTLL-2 pSTAT5), or no more than about a 5-fold reduction in EC50 value (ng/mL, CTLL-2 pSTAT5), or no more than about a 4.5-fold reduction in EC50 value (ng/mL, CTLL-2 pSTAT5), or no more than about a 4-fold reduction in EC50 value (ng/mL, CTLL-2 pSTAT5), or no more than about a 3.5-fold reduction in EC50 value (ng/mL, CTLL-2 pSTAT5), or even no more than about a 3-fold reduction in EC50 value (ng/mL, CTLL-2 pSTAT5) when compared to IL-15.

In some further embodiments, the long-acting IL-15 receptor agonist exhibits no more than about a 50% reduction in receptor alpha binding ($K_D$, pM) when compared to unconjugated IL-15, e.g., when measured using a technique suitable for determining receptor alpha binding, such as, for example surface plasmon resonance (SPR). In some related embodiments, the long-acting IL-15 receptor agonist exhibits no more than about a 45% reduction in receptor alpha binding ($K_D$, pM), or exhibits no more than about a 40% reduction in receptor alpha binding ($K_D$, pM), or exhibits no more than about a 35% reduction in receptor alpha binding ($K_D$, pM), or even exhibits no more than about a 30% reduction in receptor alpha binding ($K_D$, pM) when compared to unconjugated IL-15.

In yet some further embodiments, the long-acting IL-15 receptor agonist exhibits no more than about a 7-fold reduction in EC50 value (ng/mL, CTLL-2 pSTAT5) when compared to unmodified IL-15 and no more than about a 50% reduction in receptor alpha binding ($K_D$, pM) when compared to IL-15, including any one or more particular combinations of reductions in EC50 values or $K_D$ values described above.

In yet one or more embodiments, provided is a composition comprising a long acting IL-15 R agonist as described herein, or a pharmaceutically acceptable salt thereof, and at least one pharmaceutically acceptable excipient.

In yet some further embodiments, the long acting IL-15 R agonist or composition is effective when administered at a therapeutically effective dose to a subject to stimulate NK activation and/or proliferation.

In yet one or more further embodiments, the long acting IL-15 R agonist or composition is effective when administered at a therapeutically effective dose to a subject to support CD8 T-cell survival and/or memory formation.

In another aspect, provided herein is a method of treating a condition that is responsive to treatment with IL-15 by administering to a subject having the condition a therapeutically effective dose of a long-acting IL-15 R agonist, or a composition comprising such agonist, as provided herein.

In yet a further aspect, provided is a method for treating a cancer by administering to a subject having cancer a therapeutically effective dose of a long-acting IL-15 R agonist or composition as provided herein.

Additional aspects and embodiments are set forth in the following description and claims.

BRIEF DESCRIPTION OF THE DRAWINGS

FIG. 11A illustrates Ki67 expression (expressed as a percentage) over time, while FIG. 11B illustrates NK cell counts (cells/ul) versus time post administration for each of the sample groups.

FIG. 12A demonstrates increases in numbers of terminal effector cells, expressed in cells/µL from 24 hours to 120 hours post administration; FIG. 12B demonstrates increases in numbers of pre-NK cells, expressed in cells/ηL from 24 hours to 120 hours post administration; FIG. 12C demonstrates increases in numbers of high effector cells, expressed in cells/µL from 24 hours to 120 hours post administration and FIG. 12D demonstrates increases in numbers of early NK cells, expressed in cells/µL from 24 hours to 120 hours post administration.

FIG. 16A illustrates Ki67 expression (expressed as a percentage) in NK cells from pre-dose to 15 days post-administration, while FIG. 16B illustrates NK cell counts from pre-dose to 15 days post-administration.

FIG. 22A demonstrates increases in numbers of terminal effector cells, expressed in cells/4 from 24 hours to 120 hours post administration; FIG. 22B demonstrates increases in numbers of pre-NK cells, expressed in cells/4 from 24 hours to 120 hours post administration; FIG. 22C demonstrates increases in numbers of high effector cells, expressed in cells/4 from 24 hours to 120 hours post administration and FIG. 22D demonstrates increases in numbers of early NK cells, expressed in cells/4 from 24 hours to 120 hours post administration.

FIG. 28A demonstrates increases in percentage of Ki67 CD49b cells, from 24 hours to 240 hours post administration; FIG. 22B demonstrates increases in percentage of Granzyme B CD49b cells, from 24 hours to 240 hours post administration; FIG. 28C demonstrates increases in number of CD49b cells, expressed in cells/µL from 24 hours to 240 hours post administration; and FIG. 28D demonstrates increases in percentage of granB+MFI CD49b cells, from 24 hours to 240 hours post administration.

FIG. 29A is a plot of plasma concentration of test article (IL-15 or Conjugate 1) during a 144 hour time course following administration of a single intravenous dose of test articles in balb/c mice at 0.5 and 0.3 mg/kg, respectively. Conjugate 1 exhibits a half-life of approximately 12 hours, whereas IL-15 is quickly cleared from the plasma with a half-life of less than 1 hour. FIG. 29B is a graph of pSTAT5 percent positivity within CD8 T cells in mice after a single injection of Conjugate 1 at 0.03 and 0.3 mg/kg. Conjugate 1 at both dose levels induces sustained pSTAT5 signaling in CD8 T cells. A 120 hour time course, including pre-dose, are shown. FIG. 29C is a graph of pSTAT5 percent positivity within murine NK cells after a single injection of Conjugate 1 at 0.03 and 0.3 mg/kg. Conjugate 1 at both dose levels induces robust and sustained pSTAT5 signaling in NK cells.

FIGS. 44A, 44B and 44C are plots illustrating cell counts versus time post administration for NK cells (FIG. 44A), CD8 T cells (FIG. 44B) and CD4 T cells (FIG. 44C) in cynomolgus monkeys following i.v. administration of a vehicle (black) or Conjugate 1 at doses of 0.003 mg/kg (blue, downward-facing triangles), 0.01 mg/kg (green, diamonds) or 0.1 mg/kg (orange, solid squares) as described in Example 27.

FIGS. 45A, 45B and 45C are plots illustrating Ki-67 percent positivity after a single dose of Conjugate 1 at a dose of 0.001 mg/kg (purple, solid squares), 0.003 mg/kg (blue, downward-facing triangles) or 0.1 mg/kg (orange, solid squares) in cynomolgus monkeys as described in Example 27. The vehicle (black) levels are also shown. All dose levels returned to baseline by at least 17 days post dose. The 0.1 mg/kg and 0.003 mg/kg dose levels induced a robust increase of Ki-67 percent positivity in NK cells and CD8 T cells. The 0.1 mg/kg dose level induced an increase of Ki-67 percent positivity in all cell types tested.

FIGS. 46A, 46B and 46C illustrate the degree of STAT5 phosphorylation in NK cell (FIG. 46A), CD8 T cell (FIG. 46B) and CD4 T cell (FIG. 46C) lymphocytes following administration of a single i.v. dose of either vehicle (black) or 0.001 mg/kg (purple, solid squares), 0.01 mg/kg (green, diamonds) or 0.1 mg/kg (orange, solid squares) of Conjugate 1 in cynomolgus monkeys as described in Example 27.

FIGS. 47A-D are plots illustrating Ki-67 percent positivity after a single dose of Conjugate 1 at a dose of 0.001 mg/kg (purple, solid squares), 0.01 mg/kg (green, diamonds) or 0.1 mg/kg (orange, solid squares) in cynomolgus monkeys as described in Example 27. The vehicle (black) levels are also shown. FIG. 47A shows results for CD8 $T_{naive}$ cells, FIG. 47B shows results for CD8 $T_{scm}$ cells. FIG. 47C shows results for CD8 $T_{cm}$ cells. FIG. 47D shows results for CD8 $T_{em}$ cells.

DETAILED DESCRIPTION

Figures 1, 2:
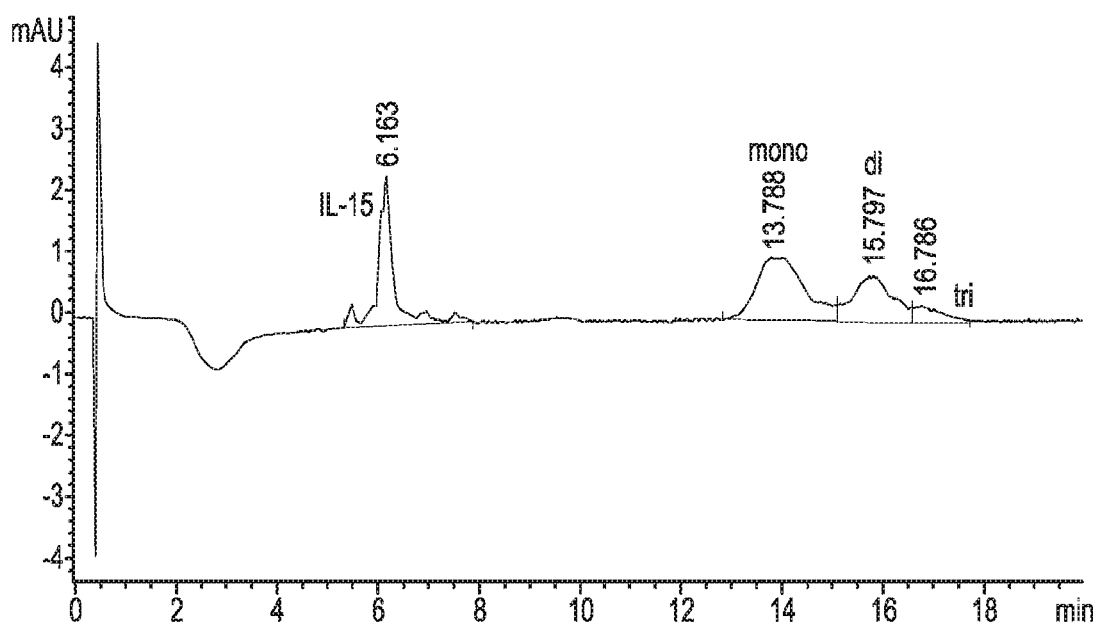
FIG. 1 provides the amino acid sequence of an exemplary recombinant human IL-15 from *E. coli* (SEQ ID NO:1), a single, non-glycosylated polypeptide chain containing 115 amino acids, with a molecular weight of 12.9 kDa.
FIG. 2 is a chromatogram illustrating the RP-HPLC analysis of an exemplary conjugation reaction mixture as described in Example 1.

Before describing one or more aspects or embodiments of the present disclosure in detail, it should be noted that the presented disclosure is not intended to be limited to the particular synthetic techniques, IL-15 moieties, and the like, as such may vary as would be understood by one having ordinary skill in the art to which this disclosure applies.

In describing and claiming certain features of this disclosure, the following terminology will be used in accordance with the definitions described below unless indicated otherwise.

It must be noted that, as used in this specification and the appended claims, the singular forms "a," "an," and "the" include plural referents unless the context clearly dictates otherwise.

In describing and claiming one or more embodiments, the following terminology will be used in accordance with the definitions described below.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two atoms within a given molecule but also on the substituents attached to these atoms. Appropriate hydrolytically unstable or weak linkages may include but are not limited to carboxylate ester, phosphate ester, anhydrides, acetals, ketals, acyloxyalkyl ether, imines, orthoesters, peptides, oligonucleotides, thioesters, and carbonates.

An "enzymatically degradable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages generally include but are not limited to the following: carbon-carbon bonds (e.g., in aliphatic chains), ethers, amides, amines, and the like. Generally, a stable linkage is one that exhibits a rate of hydrolysis of less than about 1-2% per day under physiological conditions. Hydrolysis rates of representative chemical bonds can be found in most standard chemistry textbooks.

A covalent "releasable" linkage, for example, in the context of a polyethylene glycol that is covalently attached to an active moiety such as interleukin-15, is one that releases or detaches a polyethylene glycol polymer from the active moiety under physiological conditions, e.g., by any suitable mechanism, at a rate that is clinically useful and includes, for example and without limitation, hydrolyzable bonds and enzymatically degradable linkages.

"Substantially" or "essentially" means nearly totally or completely, for instance, 95% or greater of a given quantity.

Similarly, "about" or "approximately" as used herein means within plus or minus 5% of a given quantity.

"Optional" or "optionally" means that the subsequently described circumstance may but need not necessarily occur, so that the description includes instances where the circumstance occurs and instances where it does not.

"Pharmaceutically acceptable excipient" or "pharmaceutically acceptable carrier" refers to a component that may be included in a composition as described herein and causes no significant adverse toxicological effects to a subject.

The phrases "pharmaceutically effective amount" and "pharmacologically effective amount" and "therapeutically effective amount" and "physiologically effective amount" are used interchangeably herein and refer to the amount of a long acting IL-15 R agonist as provided herein that is needed to provide a desired level of the substance in the bloodstream or in a target tissue to produce a desired biological or medicinal response. For example, such a response may be to destroy target cancer cells or to slow or arrest the progression of cancer in a subject. The term also applies to a dose that will induce a particular response in target cells. The precise amount will depend upon numerous factors, such as for example, the particular condition being treated, the intended patient population, individual patient considerations, the components and physical characteristics of the therapeutic composition to be administered, and the like.

Reference to a long acting IL-15 R agonist as described herein is meant to encompass pharmaceutically acceptable salt forms thereof.

The term "patient," or "subject" as used herein refers to a living organism suffering from or prone to a condition that can be prevented or treated by administration of a compound or composition as provided herein. Subjects include, but are not limited to, mammals (e.g., murines, simians, equines, bovines, porcines, canines, felines, and the like), and preferably are human.

Molecular weight in the context of a water-soluble polymer, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques (e.g. gel filtration chromatography). Most commonly employed are gel permeation chromatography and gel filtration chromatography. Other methods for determining molecular weight include end-group analysis or the measurement of colligative properties (e.g., freezing-point depression, boiling-point elevation, or osmotic pressure) to determine number average molecular weight or the use of light scattering techniques, ultracentrifugation, MALDI TOF, or viscometry to determine weight average molecular weight. PEG polymers are typically polydisperse (i.e., the number average molecular weight and the weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

The terms "active," "reactive" or "activated" when used in conjunction with a particular functional group, refer to a reactive functional group that reacts readily with an electrophile or a nucleophile on another molecule. This is in contrast to those groups that require strong catalysts or highly impractical reaction conditions in order to react (i.e., a "non-reactive" or "inert" group).

As used herein, the term "functional group" or any synonym thereof is meant to encompass protected forms thereof as well as unprotected forms.

The terms "spacer moiety," "linkage" and "linker" may be used herein to refer to a bond or an atom or a collection of atoms optionally used to link interconnecting moieties such as a terminus of a polymeric reagent and an IL-15 moiety. The spacer moiety may be hydrolytically stable or may include a physiologically hydrolysable, enzymatically degradable, or otherwise releasable linkage. Unless the context clearly dictates otherwise, a spacer moiety optionally exists between any two elements of a compound (e.g., an IL-15 moiety and a water-soluble polymer such as a PEG can be attached directly or indirectly through a spacer moiety).

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include methyl, ethyl, propyl, butyl, pentyl, 3-methylpentyl, and the like.

"Lower alkyl" refers to an alkyl group containing from 1 to 6 carbon atoms, and may be straight chain or branched, as exemplified by methyl, ethyl, n-butyl, i-butyl, and t-butyl.

"Alkoxy" refers to an —OR group, wherein R is alkyl or substituted alkyl, preferably $C_{1-6}$ alkyl (e.g., methoxy, ethoxy, propyloxy, and so forth).

The term "substituted" as in, for example, "substituted alkyl," refers to a moiety (e.g., an alkyl group) substituted with one or more noninterfering substituents, such as, but not limited to: alkyl, $C_{3-8}$ cycloalkyl, e.g., cyclopropyl, cyclobutyl, and the like; halo, e.g., fluoro, chloro, bromo, and iodo; cyano; alkoxy, lower phenyl; substituted phenyl; and the like. "Substituted aryl" is aryl having one or more noninterfering groups as a substituent. For substitutions on a phenyl ring, the substituents may be in any orientation (i.e., ortho, meta, or para).

"Noninterfering substituents" are those groups that, when present in a molecule, are typically nonreactive with other functional groups contained within the molecule.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably sulfur, oxygen, or nitrogen, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is heteroaryl having one or more noninterfering groups as substituents.

"Substituted heterocycle" is a heterocycle having one or more side chains formed from noninterfering substituents.

An "organic radical" as used herein shall include alkyl, substituted alkyl, aryl, and substituted aryl.

"Pharmaceutically acceptable excipient or carrier" refers to an excipient that may optionally be included in the compositions of the invention and that causes no significant adverse toxicological effects to the patient.

The term "IL-15 moiety," as used herein, refers to a peptide or protein moiety having human IL-15 activity. In addition, the term "IL-15 moiety" encompasses both the IL-15 moiety prior to conjugation as well as the IL-15 moiety residue following conjugation. As will be explained in further detail below, one of ordinary skill in the art can determine whether any given moiety has IL-15 activity. Proteins comprising an amino acid sequence corresponding to any one of SEQ ID NOs: 1 through 3 is an IL-15 moiety, as well as any protein or polypeptide substantially homologous thereto. As used herein, the term "IL-15 moiety" includes such peptides and proteins modified deliberately, as for example, by site directed mutagenesis or accidentally through mutations. These terms also include analogs having from 1 to 6 additional glycosylation sites, analogs having at least one additional amino acid at the carboxy terminal end of the peptide or protein wherein the additional amino acid(s) includes at least one glycosylation site, and analogs having an amino acid sequence which includes at least one glycosylation site. The term includes naturally, recombinantly and synthetically produced moieties.

The term "substantially homologous" or "substantially identical" means that a particular subject sequence, for example, a mutant sequence, varies from a reference sequence by one or more substitutions, deletions, or additions, the net effect of which does not result in an adverse functional dissimilarity between the reference and subject sequences. For purposes herein, a sequence having greater than 95 percent homology (identity), equivalent biological activity (although not necessarily equivalent strength of biological activity), and equivalent expression characteristics to a given sequence is considered to be substantially homologous (identical). For purposes of determining homology, truncation of the mature sequence should be disregarded. Exemplary IL-15 polypeptides for use herein include those sequences that are substantially homologous to SEQ ID NO: 1. SEQ ID NO:2 is nearly identical to SEQ ID NO:1, with the exception that SEQ ID NO:2 has a methionine at the beginning of the sequence that is required for initiating translation in E. coli.

The term "fragment" means any protein or polypeptide having the amino acid sequence of a portion or fragment of an IL-15 moiety, and having the biological activity, or substantially the biological activity, of IL-15. Fragments include proteins or polypeptides produced by proteolytic degradation of an IL-15 moiety as well as proteins or polypeptides produced by chemical synthesis by methods routine in the art.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

Overview

The instant disclosure is directed to providing a long-acting IL-15 receptor agonist. Such an agonist will ideally possess several advantageous and unpredictable features, such as, for example, at least one if not more of the following: (i) the ability to deliver sustained IL-15 activity by providing a measurable pharmacodynamic effect without the need for daily dosing, (ii) retains to a large degree binding to IL-15 receptor a (i.e., in comparison to IL-15), (iii) stimulates NK cell activation and/or proliferation, and/or (iv) supports CD8 T-cell survival and/or memory formation, and (v) provides inhibition of tumor growth. Surprisingly, the Applicants have arrived at a long acting IL-15 R agonist that possesses a unique combination of advantageous properties, to be described in greater detail below.

Long Acting IL-15 R Agonist and Related Compositions

Generally, a long acting IL-15 receptor agonist or a pharmaceutically acceptable salt form thereof comprises a single linear PEG (polyethylene glycol) moiety stably covalently attached to an IL-15 amino group via an amide linkage. Intervening between the PEG moiety and the stable amide linkage to an IL-15 amino group is a linear unsubstituted alkylene group ($-CH_2-)_m$ having from 2 to 5 carbon atoms (i.e., m=2, 3, 4, or 5).

When considering the IL-15 moiety, the term "IL-15 moiety" refers to the IL-15 moiety prior to conjugation as well as to the IL-15 moiety following attachment to a non-peptidic, water-soluble polymer such as a poly(alkylene oxide) (e.g. a poly(ethylene glycol) or PEG). While specific reference is made to PEG hereafter as the non-peptidic, water-soluble polymer below, it will be understood that the disclosure relates generally to a non-peptidic, water-soluble polymer or poly(alkylene glycol). It will be understood, however, that when the original IL-15 moiety is attached to a polyethylene glycol moiety, the IL-15 moiety is slightly altered due to the presence of one or more covalent bonds associated with linkage to the polymer(s).

The IL-15 moiety can be derived from non-recombinant methods and from recombinant methods, and the disclosure is not limited in this regard. In addition, the IL-15 moiety can be derived from human sources, animal sources (including insects), fungi sources (including yeasts), and plant sources.

The IL-15 moiety can be obtained according to the procedures described by, for example, Grabstein et al. [See. Grabstein et al. (1994) *Science* 264:965-968]. The IL-15 moiety can also be prepared using recombinant methods, such as, for example, those described in EP Patent No. 0 772 624 B2 to Immunex Corporation. Alternatively, the IL-15 moiety can be purchased commercially from, for example, GenScript USA Inc. (Piscataway NJ) and Peprotech (Rockyhill, NJ).

The IL-15 moiety can be expressed in bacterial [e.g., *E. coli*, see, for example, Fischer et al. (1995) *Biotechnol. Appl. Biotechnol.* 21(3):295-311], mammalian [see, for example, Kronman et al. (1992) *Gene* 121:295-304], yeast [e.g., *Pichia pastoris*, see, for example, Morel et al. (1997) *Biochem. J.* 328(1):121-129], and plant [see, for example, Mor et al. (2001) *Biotechnol. Bioeng.* 75(3):259-266] expression systems. The expression can occur via exogenous expression (when the host cell naturally contains the desired genetic coding) or via endogenous expression.

Although recombinant-based methods for preparing proteins can differ, recombinant methods typically involve constructing the nucleic acid encoding the desired polypeptide or fragment, cloning the nucleic acid into an expression vector, transforming a host cell (e.g., plant, bacteria, yeast, transgenic animal cell, or mammalian cell such as Chinese hamster ovary cell or baby hamster kidney cell), and expressing the nucleic acid to produce the desired polypeptide or fragment. Methods for producing and expressing recombinant polypeptides in vitro and in prokaryotic and eukaryotic host cells are known to those of ordinary skill in the art.

To facilitate identification and purification of the recombinant polypeptide, nucleic acid sequences that encode for an epitope tag or other affinity binding sequence can be inserted or added in-frame with the coding sequence, thereby producing a fusion protein comprised of the desired polypeptide and a polypeptide suited for binding. Fusion proteins can be identified and purified by first running a mixture containing the fusion protein through an affinity column bearing binding moieties (e.g., antibodies) directed against the epitope tag or other binding sequence in the fusion proteins, thereby binding the fusion protein within the column. Thereafter, the fusion protein can be recovered by washing the column with the appropriate solution (e.g., acid) to release the bound fusion protein. The recombinant polypeptide can also be purified by lysing the host cells, separating the polypeptide, e.g., by ion-exchange chromatography, affinity binding approaches, hydrophobic interaction approaches, and thereafter identify by MALDI or western blot, and collecting the polypeptide. These and other methods for identifying and purifying recombinant polypeptides are known to those of ordinary skill in the art. In one or more embodiments, however, the IL-15 moiety is not in the form of a fusion protein.

Depending on the system used to express proteins having IL-15 activity, the IL-15 moiety can be unglycosylated or glycosylated and either may be used. That is, the IL-15 moiety can be unglycosylated or the IL-15 moiety can be glycosylated. In one or more embodiments, the IL-15 moiety is unglycosylated.

The IL-15 moiety can advantageously be modified to include and/or substitute one or more amino acid residues such as, for example, lysine, cysteine and/or arginine, in order to provide facile attachment of the polymer to an atom within the side chain of the amino acid. An example of substitution of an IL-15 moiety is described in U.S. Pat. No. 6,177,079. In addition, the IL-15 moiety can be modified to include a non-naturally occurring amino acid residue. Techniques for adding amino acid residues and non-naturally occurring amino acid residues are well known to those of ordinary skill in the art. Reference is made to J. March, Advanced Organic Chemistry: Reactions Mechanisms and Structure, 4th Ed. (New York: Wiley-Interscience, 1992), and *Bioinformatics for Geneticists* (eds. Michael R. Barnes and Ian C Gray), 2003 John Wiley & Sons, Ltd, Chapter 14, *Amino Acid Properties and Consequences of Substitutions*, Betts, M. J., and Russell, R. B.

In addition, the IL-15 moiety can advantageously be modified to include attachment of a functional group (other than through addition of a functional group-containing amino acid residue). For example, the IL-15 moiety can be modified to include a thiol group. In addition, the IL-15 moiety can be modified to include an N-terminal alpha carbon. In addition, the IL-15 moiety can be modified to include one or more carbohydrate moieties. In addition, the IL-15 moiety can be modified to include an aldehyde group. In addition, the IL-15 moiety can be modified to include a ketone group. In some embodiments of the invention, it is preferred that the IL-15 moiety is not modified to include one or more of a thiol group, an N-terminal alpha carbon, carbohydrate, aldehyde group and ketone group.

Exemplary IL-15 moieties are described herein, in the literature, and in, for example, U.S. Patent Application Publication No. US 2006/0104945, Pettit et al. (1997) *J. Biol. Chem.* 272(4):2312-2318, and Wong et al. (2013) *OncoImmunology* 2(11), e26442:1-3. Preferred IL-15 moieties include those having an amino acid sequence comprising sequences selected from the group consisting of SEQ ID NOs: 1 through 3, and sequences substantially homologous thereto (wherein even if SEQ ID NOs 2 and 3, and sequences substantially homologous thereto do not meet the in vitro activity standard of an IL-15 moiety provided herein, it will be understood for purposes of the present invention that these sequences are also understood to be "IL-15 moieties"). A preferred IL-15 moiety has an amino acid sequence corresponding to SEQ ID NO: 1. In some embodiments, the IL-15 moiety is a functional homolog having at least about 85% or at least about 90% identity with any one of SEQ ID NOs: 1-3. In some embodiments, the IL-15 moiety is a functional homolog having at least about 95%, 98% or 99% identity with any one of SEQ ID NOs: 1-3.

In some instances, the IL-15 moiety will be in a "monomer" form, wherein a single expression of the corresponding peptide is organized into a discrete unit. In other instances, the IL-15 moiety will be in the form of a "dimer" (e.g., a dimer of recombinant IL-15) wherein two monomer forms of the protein are associated to each other.

In addition, precursor forms of IL-15 can be used as the IL-15 moiety. An exemplary precursor form of IL-15 has the sequence of SEQ ID NO: 3.

Truncated versions, hybrid variants, and peptide mimetics of any of the foregoing sequences can also serve as the IL-15 moiety. Biologically active fragments, deletion variants, substitution variants or addition variants of any of the foregoing that maintain at least some degree of IL-15 activity can also serve as an IL-15 moiety.

For any given peptide, protein moiety or conjugate, it is possible to determine whether that peptide, protein moiety or conjugate has IL-15 activity. Various methods for determining in vitro IL-15 activity are described in the art. An exemplary approach is based on a pSTAT assay. Briefly, if an IL-15-dependent CTLL-2 cell is exposed to a test article having IL-15 activity, initiation of a signaling cascade results that includes the phosphorylation of STAT5 at tyrosine residue 694 (Tyr694), which can be quantitatively measured. Assay protocols and kits are known and include, for example, the MSD Phospho(Tyr694)/Total STATa,b Whole Cell Lysate Kit (Meso Scal Diagnostics, LLC, Gaithersburg, MD). For example, using this approach, a proposed IL-15 moiety that exhibits a pSTAT5 $EC_{50}$ value of no more than about 300 ng/mL (more preferably no more than about 150 ng/mL) at least one of 5 minutes or at 10 minutes is considered an "IL-15 moiety" in connection with the present disclosure. It is preferred, however, that the IL-15 moiety used is more potent (e.g., having a pSTAT5 $EC_{50}$ value of less than 150 ng/mL at one of least 5 minutes or 10 minutes, such as less than about 1 ng/mL, and even more preferably less than 0.5 ng/mL at least one of 5 minutes or at 10 minutes).

Other methodologies known in the art can also be used to assess IL-15 function, including electrometry, spectrophotometry, chromatography, and radiometric methodologies. See, for example, Ring et al. (2012) Nat. Immunol. 13(12): 1187-1195 for one such additional type of assay.

Assays for use in connection with measuring the activity of an IL-15 moiety can also be used to measure the activity of the long acting IL-15 R agonists described herein. See, for example, the supporting examples provided herein.

A compound is considered to be a long-acting, IL-15 R agonist in accordance with the present disclosure so long as, following administration to a subject, the agonist exhibits IL-15 agonism in vivo for an amount of time that is longer than would be the case for administration of IL-15. Conventional approaches, such as those involving radiolabeling a compound, administering the compound in vivo, and determining its clearance, can be used to assess whether a compound proposed to be a long-acting, IL-15 R agonist is "long-acting" (i.e., has a clearance that is longer than that of IL-15 administered in the same in vivo system). For the purposes herein, the long acting nature of a long-acting IL-15 R agonist may be, and is typically determined using flow cytometry to measure STAT5 phosphorylation in lymphocytes at various time points after administration of the agonist to be evaluated in mice. As a reference, the signal is lost by around 24 hours with IL-15, but is sustained for a period greater than that for a long-acting IL-15 agonist.

As previously discussed, a preferred long acting IL-15 R agonist will generally comprise a single linear PEG (polyethylene glycol) moiety stably covalently attached to an IL-15 amino group via an amide linkage. Intervening between the PEG moiety and the stable amide linkage to an IL-15 amino group is a linear unsubstituted alkylene group $(\sim CH_2 \sim)_m$ having from 2 to 5 carbon atoms (i.e., where m=2, 3, 4, or 5).

For example, in some embodiments, the unsubstituted alkylene group is (~CH$_2$~)$_2$, or, in some additional embodiments, the unsubstituted alkylene group is (~CH$_2$~)$_3$, in yet some further embodiments, the unsubstituted alkylene group is (~CH$_2$~)$_4$, in yet some further embodiments, the unsubstituted alkylene group is the unsubstituted alkylene group is (~CH$_2$~)$_5$.

For example, in some embodiments, the long acting IL-15 receptor agonist has the following structure:

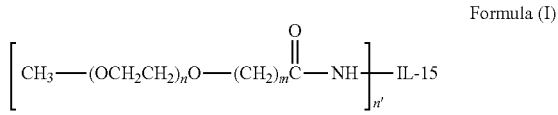

Formula (I)

wherein IL-15 is an interleukin-15 moiety, n is an integer from about 150 to about 3,000; m is an integer from 2-5 (e.g., 2, 3, 4, or 5) and n' is 1. In Formula I (and in similar formulae provided herein) the ~NH~ in the structure represents an amino group of the IL-15 moiety. Formula (I) may also be depicted as follows, where the parentheses are shifted to reflect a terminal PEG methoxy group,

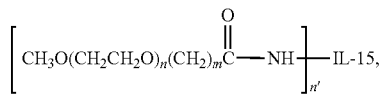

and the two formulae may be used interchangeably. Illustrative exemplary compounds include the following encompassed by Formula (I):

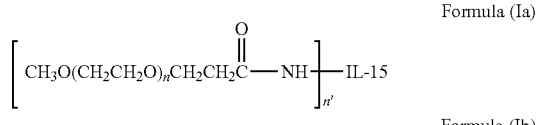

Formula (Ia)

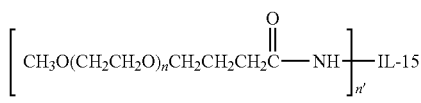

Formula (Ib)

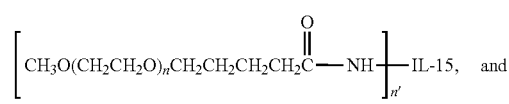

Formula (Ic)

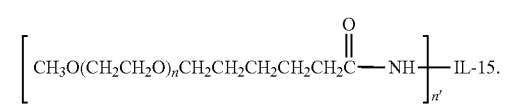

Formula (Id)

In some preferred embodiments, the long acting IL-15 receptor agonist corresponds to Formula (Ia) or Formula (Ib). In some particularly preferred embodiments, the long acting IL-15 receptor agonist corresponds to Formula (Ib).

In some further embodiments, in reference to the structures and formulae described herein, n is an integer from about 200 to about 2000, or from about 400 to about 1300, or from about 450 to about 1200. That is to say, in some embodiments, n is an integer from about 200 to about 2000. In yet some further embodiments, n is an integer from about 400 to about 1300. In yet some further embodiments, n is an integer from about 450 to about 1200.

PEGs having a molecular weight corresponding to any one of the foregoing ranges of n values are generally preferred.

In one or more embodiments, n is an integer having a value that corresponds to a polyethylene glycol polymer having a weight average molecular weight selected from the group consisting of about 10,000 daltons (where n is ~227), or about 15,000 daltons (where n is ~340), or about 20,000 daltons (where n is ~454), or about 25,000 daltons (where n is ~568), or about 30,000 daltons (where n is ~681), or about 40,000 daltons (where n is ~909), or about 50,000 daltons (where n is ~1136) or even about 60,000 daltons (where n is 1364) or greater.

Further exemplary weight-average molecular weights for the polyethylene glycol portion of the compound, in addition to the foregoing, include about 11,000 daltons, about 12,000 daltons, about 13,000 daltons, about 14,000 daltons, about 22,500 daltons, about 35,000 daltons, about 45,000 daltons, about 55,000 daltons, about 65,000 daltons, about 70,000 daltons, and about 75,000 daltons.

In some preferred embodiments, the weight-average molecular weight of the polyethylene glycol polymer portion of the compound is about 40,000 daltons.

While the PEG moiety is preferably end-capped as shown above in Formula (I) with a methoxy group, the PEG moiety may be capped at its terminus with any lower C$_{1-6}$ alkoxy group, or may terminate in a hydroxyl group, or other suitable end-capping group.

In some embodiments, the long acting IL-15 receptor agonist composition comprises no more than about 20 mole percent (mol %) of long-acting IL-15 receptor agonists (of the IL-15 containing molecules in the composition), when considered collectively, encompassed by the formula:

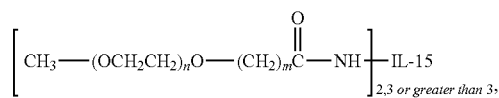

Formula (II)

where the values of n and m are as provided for Formula (I) above. That is to say, in terms of the long-acting IL-15 receptor agonist component of such compositions, no more than about 20 mole percent of long-acting IL-15 receptor agonists comprised in the composition are of Formula (II).

In some additional embodiments, the long acting IL-15 receptor agonist composition comprises no more than about 15 mole percent (mol %) of long-acting IL-15 receptor agonists (of the IL-15 containing molecules in the composition), when considered collectively, encompassed by the formula:

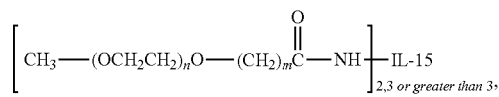

Formula (II)

where the values of n and m are as provided for Formula (I) above. That is to say, in terms of the long-acting IL-15 receptor agonist component of such compositions, no more than about 15 mol percent of long-acting IL-15 receptor agonists comprised in the composition are of Formula (II). In some embodiments, the long-acting IL-15 receptor agonist composition comprises no more than about 0.1-20 mol % of compounds of Formula (II). In embodiments, the compositions comprise no more than about 0.1-15, 0.1-10, 0.1-5, 0.1-1, 1-20, 1-15, 1-10, 1-5, 5-20, 5-15, 5-10, 10-20, 10-15, or 15-20 mol % of compounds of Formula (II).

In some particular embodiments related to the foregoing, the long acting IL-15 receptor agonist composition, in reference to Formula (Ia), comprises no more than about 15 mole percent (mol %) of long-acting IL-15 receptor agonists (of the IL-15 containing molecules in the composition), when considered collectively, encompassed by the formula:

Formula (IIa)

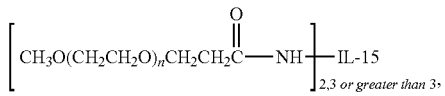

where the values of n and m are as provided for Formula (Ia) above.

In some other preferred embodiments, the long acting IL-15 receptor agonist composition, in reference to Formula (Ib), comprises no more than about 15 mole percent (mol %) of long-acting IL-15 receptor agonists (of the IL-15 containing molecules in the composition), when considered collectively, encompassed by the formula:

Formula (IIb)

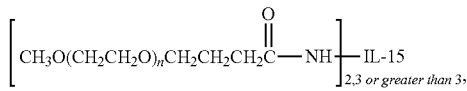

where the values of n and m are as provided for Formula (Ib) above.

In some other embodiments, the long acting IL-15 receptor agonist composition, in reference to Formula (Ic), comprises no more than about 15 mole percent (mol %) of long-acting IL-15 receptor agonists (of the IL-15 containing molecules in the composition), when considered collectively, encompassed by the formula:

Formula (IIc)

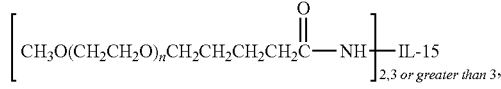

where the values of n and m are as provided for Formula (Ic) above.

In some other embodiments, the long acting IL-15 receptor agonist composition, in reference to Formula (Id), comprises no more than about 15 mole percent (mol %) of long-acting IL-15 receptor agonists (of the IL-15 containing molecules in the composition), when considered collectively, encompassed by the formula:

Formula (IId)

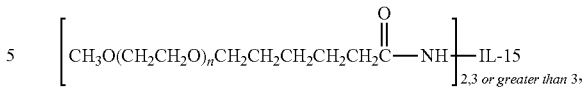

where the values of n and m are as provided for Formula (Id) above.

In some embodiments, the long-acting IL-15 receptor agonist composition comprises no more than about 0.1-20 mol % of compounds of Formula (II), including compounds of Formulae (IIa), (IIb), (IIc), and (IId). In some additional embodiments, the compositions comprise no more than about 0.1-15, 0.1-10, 0.1-5, 0.1-1, 1-20, 1-15, 1-10, 1-5, 5-20, 5-15, 5-10, 10-20, 10-15, or 15-20 mol % of compounds of Formula (II), including compounds of Formulae (IIa), (IIb), (IIc), and (IId). In some embodiments, the compositions comprise no more than about 0.1, 1, 5, 10, 15, or 20 mol % of compounds of Formula (II), including compounds of Formulae (IIa), (IIb)), (IIc), and (IId). It will be appreciated that the compositions may be purified by methods known in the art for compounds of Formula (I) resulting in no, trace amounts, or substantially no compounds of Formula (II) present in the composition.

For example, in some embodiments, the long acting IL-15 receptor agonist composition comprises no more than about 12 mole percent, or no more than about 10 mole percent of long-acting IL-15 receptor agonists, that when considered collectively, are encompassed by Formula (II), including compounds of Formulae (IIa), (IIb), (IIc), and (IId).

In some additional embodiments of the foregoing, the composition comprises no more than about 7 mol % of long acting IL-15 receptor agonists having n' equal to 2, 3, or greater than 3 (i.e., higher PEGmers). In yet some other embodiments, the composition comprises no more than about 5 mol % of long acting IL-15 receptor agonists having n' equal to 2, 3 or greater than 3 (i.e., of 2 or greater).

In some further embodiments, the composition comprises a long-acting IL-15 receptor agonist according to Formula (I),

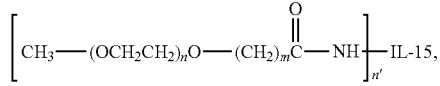

where n and m are as described above, and n' represents the average number of polyethylene glycol moieties covalently attached to IL-15 amino groups (for the composition), and n' for the composition is in a range from 1.0 to about 1.3. For example, the average number of polyethylene glycol moieties per IL-15 moiety is selected from about 1.0, 1.1, 1.2 and about 1.3. That is to say, a preferred long-acting IL-15 receptor agonist according to Formula (I) may be referred to herein as "monoPEGylated", where it is to be understood that some variability exists around the degree of PEGylation as described above. In some preferred embodiments in reference to the formulae described herein, "m" is equal to 3.

A composition of the long-acting IL-15 R agonist may comprise a single species where n' equals about 1 and the PEG moiety is attached at the same location for substantially all IL-15 conjugates in the composition, or alternatively, may comprise a mixture of monoPEGylated conjugate species where attachment of the linear polyethylene glycol moiety occurs at different sites on the interleukin-15 moiety, that is to say, where the particular attachment sites are not the same for all of the monoPEGylated IL-15 species comprised in the composition. Thus, such compositions are substantially homogeneous in terms of the number of PEG moieties attached to IL-15 (e.g., 1-mers), but are heterogeneous in terms of the locations of amino group attachment on the IL-15 molecule.

While additional PEG architectures and linkage chemistries may be employed for arriving at a long acting IL-15 R agonist, compounds such as previously described are preferred in one or more embodiments, as will become apparent when considered in light of the supporting examples. However, additional long acting IL-15 R agonists having structures as provided herein are also contemplated.

In some embodiments, the long acting IL-15 receptor agonist composition comprises at least about 80 mol % of long acting IL-15 receptor agonists (of the IL-15 containing molecules in the composition), when considered collectively, encompassed by Formula (I), including Formulae (Ia-d). In one or more embodiments, the long acting IL-15 receptor agonist composition comprises at least about 85 mol %, 90 mol %, 95 mol %, 98 mol % or 99 mol % of the long acting IL-15 receptor agonists of Formula (I).

As described above, the long acting IL-15 R agonist may be in the form of a pharmaceutically-acceptable salt. Typically, such salts are formed by reaction with a pharmaceutically-acceptable acid or an acid equivalent. The term "pharmaceutically-acceptable salt" in this respect, will generally refer to the relatively non-toxic, inorganic and organic acid addition salts. These salts can be prepared in situ in the administration vehicle or the dosage form manufacturing process, or by separately reacting a long-acting interleukin-15 receptor agonist as described herein with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, oxylate, mesylate, glucoheptonate, lactobionate, and laurylsulphonate salts and the like. (See, for example, Berge et al. (1977) "*Pharmaceutical Salts*", *J. Pharm. Sci.* 66:1-19). Thus, salts as described may be derived from inorganic acids such as hydrochloride, hydrobromic, sulfuric, sulfamic, phosphoric, nitric, and the like; or prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In some embodiments, the long acting IL-15 receptor agonist composition comprises no more than about 1-5 mol % of free IL-15 protein (of the IL-15 containing molecules in the composition), when considered collectively. In some further embodiments, the long acting IL-15 agonist composition comprises no more than about 0.5 mol %, 1 mol %, 2 mol %, 3 mol %, 4 mol %, or 5 mol % of free (i.e., unconjugated) IL-15.

To prepare a long acting IL-15 receptor agonist, the IL-15 moiety may, for example, be conjugated at its amino groups (e.g. lysines or the N-terminus) to a PEG reagent functionalized with a succinimidyl group (or other activated ester group). Using this approach, the succinimidyl activated PEG can be attached to amino groups on the IL-15 moiety in an aqueous media at a pH of about 7.0 to 9.0, although using different reaction conditions (e.g., a lower pH such as 6 to 7 or 7 to 8, or different temperatures and/or less than 15° C.) can result in the attachment of the PEG moiety to a different location on the IL-15 moiety.

A long acting IL-15 R agonist can be prepared as described in Example 1. For example, the long acting IL-15 R agonist may generally be prepared by reacting an interleukin-15, for example, purified IL-15, such as recombinant IL-15, with an activated PEG reagent such as the activated ester, methoxyPEG-succinimidyl butanoate, mPEG-SBA. Other suitable activated PEG reagents include methoxyPEG-succinimidyl propionate, methoxyPEG-succinimidyl pentanoate, and methoxyPEG-succinimidyl hexanoate. While a succinimidyl activating group is typically used, any suitable active ester or activating group may be used, wherein such reacting group is suitable for forming the desired stable amide linkage. Generally, the interleukin-15 is dissolved in a suitable buffer, such as for example, phosphate buffered saline (PBS). The PEG reagent may be added at an equimolar ratio to the IL-15 (relative to the molar amount of interleukin-15), generally in solution in a suitable buffer, or at a molar excess (based upon the molar amount of IL-15), that is up to about a 15-fold molar excess, e.g., a 2-fold molar excess, or a 5-fold molar excess, or a 7-fold molar excess, or a ten-fold molar excess, or even a 12-fold molar excess or more. In some embodiments, the PEG reagent is added at a molar excess of about 5 to 10-fold. The PEG reagent may be added in solid form, or as a solution in a suitable solvent, for example in aqueous acid such as dilute hydrochloric acid.

In some further embodiments of the method, the interleukin-15 is initially present in solution, i.e., prior to mixing with the methoxyPEG-succinimidyl alkanoate reagent, at a concentration of about 0.5 mg/mL to about 10 mg/mL. Additional illustrative concentration ranges include, for example, about 0.5-5 mg/mL, about 0.5-4 mg/mL, about 0.5-3 mg/mL, about 0.5-2 mg/mL, about 0.5-1.5 mg/mL, about 0.5-1 mg/mL, about 1-10 mg/mL, about 1-5 mg/mL, about 1-4 mg/mL, about 1-3 mg/mL, about 1-2 mg/mL, about 1-1.5 mg/mL, about 1.5-10 mg/mL, 1.5-5 mg/mL, about 1.5-4 mg/mL, about 1.5-3 mg/mL, about 1.5-2 mg/mL, about 2-10 mg/mL, about 2-5 mg/mL, about 2-4 mg/mL, about 2-3 mg/mL, about 3-10 mg/mL, about 3-5 mg/mL, about 3-4 mg/mL, about 4-10 mg/mL, about 4-5 mg/mL or about 5-10 mg/mL interleukin-15 in the solution. In some specific, but not limiting embodiments, the concentration of interleukin-15 in the solution is about 0.5 mg/mL, 1 mg/mL, 1.5 mg/mL, 2 mg/mL, 2.5 mg/mL, 3 mg/mL, 4 mg/mL, 5 mg/mL, or 10 mg/mL.

It will be appreciated that any suitable buffer may be used/or added to the reaction mixture. Some exemplary buffers include sodium phosphate (NaPi), sodium acetate (NaAc), borate, bicine, citrate, and Bis-TRIS buffers.

In some embodiments, the pH of the IL-15 solution is adjusted to around pH 8 prior to addition of the PEG reagent.

Following addition of the PEG reagent, the reaction mixture may then be adjusted, if necessary, to a suitable pH, for example, from about 7.0-8.5, or to about 8.0. In some embodiments, the reaction mixture is adjusted to a pH of about 7.0-8.0 or to about 7.4-8.5. In some particular embodiments, the reaction mixture is adjusted to a pH of about 8.0. It will be appreciated that the pH may be adjusted both prior to and following addition of the PEG reagent, as necessary to achieve the desired pH.

Interleukin-15, like many proteins, is subject to deamidation, especially at higher pHs, while lower pH levels may lead to a number is possible disadvantages such as, for example, a lower degree of conjugation at epsilon (ε) amines, and/or increased and/or undesirable positional isoforms, as well as protein aggregation. Deamidation introduces a negative charge into a protein, which may lead to changes in the protein's activity, structure, function, stability and/or may change the susceptibility of the protein to degradation. Thus, one of the challenges addressed by the instant agonists and related methods was to provide a long acting interleukin-15 receptor agonist that maintains a sufficient degree of activity (i.e., to be therapeutically useful) whilst balancing at least (i) a desired degree of conjugation, (ii) low amounts of deamidation of the interleukin-15 moiety, both before and after conjugation with the subject PEG reagents (which can, for example, lead to decreased interleukin-15 activity), and (iii) protein aggregation (e.g., both before and after conjugation), among other considerations.

Based on the competing and conflicting challenges associated with reaction parameters for preparing a long-acting interleukin-15 receptor agonist as described herein, it has been discovered by the Applicants that by adjusting the pH of the interleukin-15 solution (prior to or after reaction with the PEG reagent), and/or the IL-15-PEG reagent reaction mixture, one can arrive at optimal (lower levels) of deamidation, while still promoting conjugation of the PEG moieties to the interleukin-15 moiety (e.g., at ε amines as well as the N-terminus) to provide a long acting IL-15 R agonist as described herein. While not being bound by theory, based upon a series of reactions in which numerous reaction parameters were varied, it appears that a pH range of about 7.0 to about 8.5, or from about 7.5 to about 8.2, or from about 7.8 to about 8.2, or at about 8.0, is effective to provide for lower levels of deamidation in the product, while still promoting conjugation of the PEG moieties to form a product as described herein, which also maintains a desirable therapeutic profile.

For example, the methods described herein are effective to produce PEGylated interleukin-15 that is less than about 35% deamidated, or in some embodiments, is less than about 30% deamidated, or is less than about 25% deamidated, or is less than about 20% deamidated. In some embodiments, the level of deamidation of the product is in a range of from about 20-35%, or is in a range of about 20-25%, or is in a range of about 25-35%, or is in a range of about 25-30%. Alternatively, in some embodiments, PEGylated interleukin-15 having degrees of deamidation less than stated above are contemplated. As shown in Experiment 2 of Example 1, adjusting the pH in a range of about 7.0-8.5 resulted in a level of deamidation of 21.29% (Composition 1) or 33.26% (Composition 2).

The reactants are generally mixed for up to, and including, about 5 to 10 hours. In some embodiments, the reactants are mixed for up to, and including about 2 to 5 hours. In some embodiments, the reactants are mixed for up to, and including about 2 hours. In some exemplary embodiments, the reactants are mixed for about 30 minutes to about 3.0 hours, or from about 30 minutes to 2.5 hours, or from about 30 minutes to 2 hours, or from about 30 minutes to 1.5 hour, or from about 45 minutes to about 3.0 hours, or from about 45 minutes to about 2.5 hours, or from about 45 minutes to about 2.0 hours, or from about 45 minutes to about 1.5 hours, or from about 45 minutes to about 1.0 hour. The mixing is generally carried out under mild conditions, e.g., from about 20° C. to about 65° C., or from about 20° C. to about 40° C., or at ambient or room temperature (e.g. about 22° C.). Lower temperatures may be employed to favor a lower degree of PEGylation. The reaction may be quenched, for example, by addition of an amino acid such as glycine.

In embodiments, the pH of the composition may further be adjusted in order to mitigate deamidation. In some embodiments, the composition is adjusted to a pH of about 6.5-7.5 or 6.5-7.0. In some embodiments, the composition is adjusted to a pH of about 6.5, 6.8, 7.0 or 7.5.

The PEGylated rIL-15 reaction product may then generally be purified by any suitable method such as, for example, ion exchange chromatography to obtain the desired product. For example, anion exchange chromatography may be employed. The chromatography product pool may then be concentrated and diafiltered into suitable formulation buffer (for example, sodium acetate buffer with sucrose) using, for example, tangential flow filtration (TFF). Analysis may be conducted by any suitable method, such as for example, SDS-PAGE, reverse phase HPLC or any other suitable analytical method.

As described previously, amino groups on the IL-15 moiety provide a site of attachment between the IL-15 moiety and the polyethylene glycol moiety to provide a long acting IL-15 R agonists such as encompassed by Formula (I). For example, considering the exemplary IL-15 amino acid sequences provided herein, it is evident that there are seven lysine residues each having an ε-amino acid that may be available for conjugation. Further, the N-terminal amine of methionine can also serve as a point of attachment to the PEG moiety. It will be appreciated that the polyethylene glycol moiety may be attached at any one or more of the lysine or the N-terminal amine positions. In some embodiments, a polyethylene glycol moiety attachment site is at one or more of $Lys^{10}$ and $Lys^{11}$ (using the numbering as shown in SEQ ID NO: 2 as an example or $Lys^{11}$ and $Lys^{12}$ (using SEQ ID NO:1). In some embodiments, a polyethylene glycol moiety is attached at the N-terminal amine. It will be appreciated that any of the lysine sites may be suitable as an attachment site (e.g. $Lys^{37}$ or $Lys^{42}$ of SEQ ID NO:1) for the PEG moiety. In some embodiments, the long-acting interleukin-15 receptor agonist comprises a mixture of positional isomers, where covalent attachment of the polyethylene glycol moiety is predominately at the N-terminus (that is to say, of the collection of positional isomers, the isomer having the PEG moiety attached at the N-terminus is present in the highest amount, when compared to the other positional isomers).

If desired, the product pool may be further separated into positional isomers by reverse phase chromatography using a reverse phase-high performance liquid chromatography (RP-HPLC) using a suitable column (e.g., a C18 column or C3 column, available commercially from companies such as Amersham Biosciences or Vydac) or by ion exchange chromatography using an ion exchange column, e.g., a Sepharose™ ion exchange column available from Amersham Biosciences. Either approach can be used to separate PEG-interleukin-15 positional isomers having the same molecular weight (i.e., positional isoforms).

Gel filtration columns suitable for carrying out this type of separation include Superdex™ and Sephadex™ columns available from GE Healthcare (Buckinghamshire, UK). Selection of a particular column will depend upon the desired fractionation range desired. Elution is generally carried out using a suitable buffer, such as phosphate, acetate, or the like. The collected fractions may be analyzed by a number of different methods, for example, (i) absorbance at 280 nm for protein content, (ii) dye-based protein analysis using bovine serum albumin (BSA) as a standard, (iii) iodine testing for PEG content (Sims et al. (1980) *Anal. Biochem,* 107:60-63), (iv) sodium dodecyl sulfate polyacrylamide gel electrophoresis (SDS PAGE), followed by staining with barium iodide, and (v) high performance liquid chromatography (HPLC).

The instant long acting IL-15 R agonists have been discovered to possess certain notable and advantageous features. While the features described below are believed to apply generally to compounds as provided herein and encompassed by Formula (I), the following one or more features may be exhibited particularly by compounds in accordance with Formula (Ib), and by extension, Formula (IIb). The long acting IL-15 R agonist may possess one or more of the following features. For example, in some embodiments, the long-acting IL-15 receptor agonist exhibits no more than about a 7-fold reduction in EC50 value (ng/mL, CTLL-2 pSTAT5) when compared to unmodified IL-15. For example, in one or more related embodiments, the long-acting IL-15 receptor agonist exhibits no more than about a 6.5-fold reduction in EC50 value (ng/mL, CTLL-2 pSTAT5), or no more than about a 6-fold reduction in EC50 value (ng/mL, CTLL-2 pSTAT5), or no more than about a 5.5-fold reduction in EC50 value (ng/mL, CTLL-2 pSTAT5), or no more than about a 5-fold reduction in EC50 value (ng/mL, CTLL-2 pSTAT5), or no more than about a 4.5-fold reduction in EC50 value (ng/mL, CTLL-2 pSTAT5), or no more than about a 4-fold reduction in EC50 value (ng/mL, CTLL-2 pSTAT5), or no more than about a 3.5-fold reduction in EC50 value (ng/mL, CTLL-2 pSTAT5), or even no more than about a 3-fold reduction in EC50 value (ng/mL, CTLL-2 pSTAT5) when compared to IL-15. Exemplary long acting IL-15 R agonists in accordance with the foregoing features are described herein and in the accompanying Examples.

Figure 10A:
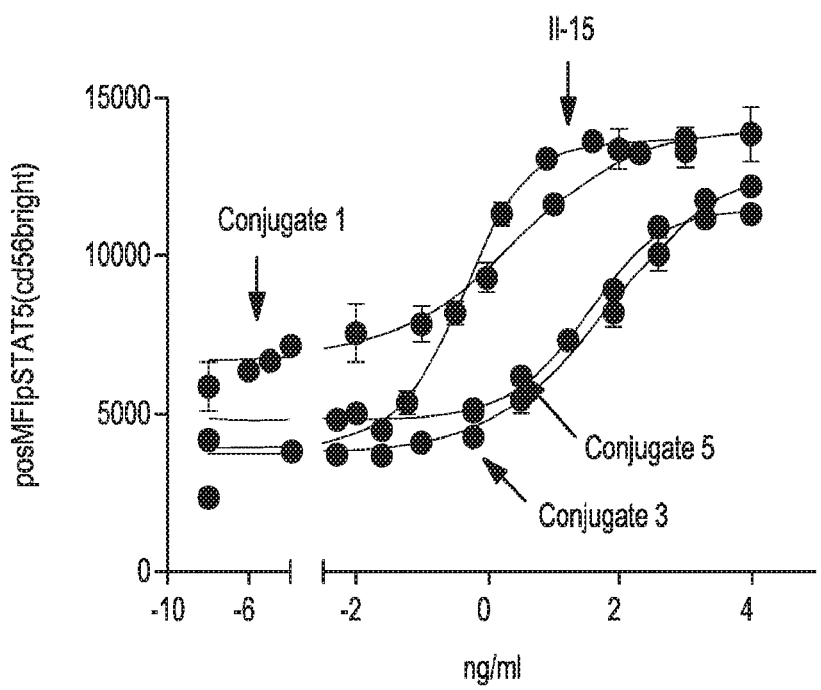
FIGS. 10A and 10B are plots demonstrating in-vitro activity of exemplary long acting IL-15 receptor agonists (Conjugates 1, 3 and 5) as measured by signaling in NK subsets of human PBMCs, CD56bright (FIG. 10A) and CD56dim (FIG. 10B) NK cells, respectively, as described in detail in Example 10.
Figure 10B:
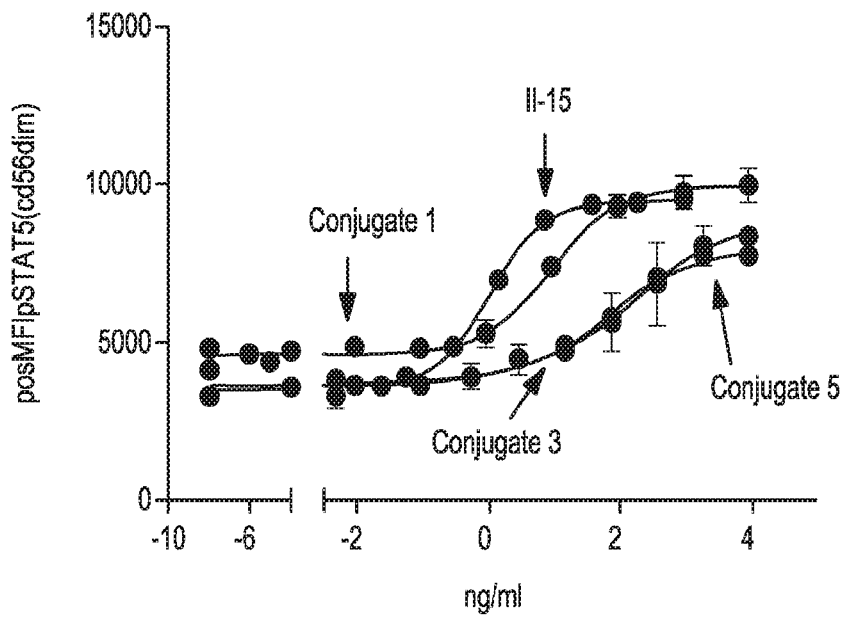

As described in Example 10, the in vitro activity of the illustrative conjugates (1, 3, and 5) induces IL-15 signaling in huPBMCs, with Conjugate 1 potently inducing such signaling. Further experiments were conducted to investigate the in vitro activity of Conjugate 1 on human CD8 T cells, NK cells and CD4 T cells (Examples 16, 22 and 26-27). As shown in FIGS. 10A-10B, at least Conjugate 1 induced similar or increased signaling as compared to IL-15 in CD56bright and CD56low cells. While Conjugate 1 was less potent than IL-15 in engaging CD8 and CD56 bright NK cells (Example 22), it is important to note Conjugate 1 achieved the same maximum response as conventional IL-15 (see FIGS. 38A-38B). As described for the mouse model in Example 16, a single injection of Conjugate 1 at two different doses induced sustained pSTAT signaling in CD8 and NK cells. As described in the mouse model of Example 26, a single injection of Conjugate 1 resulted in an increase in % pSTAT5 as compared to IL-15. In the mouse models, NK cells were the most sensitive to a single dose of Conjugate, followed by CD8 T cells with CD4 T cells being the least sensitive for the cells tested.

Conjugate 1 also induced signaling in NK cells, CD8 T cells and CD4 T cells in a non-human primate model (cynomolgus monkey model in Example 27). As with the murine model, the NK cells were the most sensitive to induction by Conjugate 1.

In some additional embodiments, the long-acting IL-15 receptor agonist exhibits no more than about a 50% reduction in receptor alpha binding ($K_D$, pM) when compared to IL-15. That is to say, in some related embodiments, the long-acting IL-15 receptor agonist exhibits no more than about a 45% reduction in receptor alpha binding ($K_D$, pM), or exhibits no more than about a 40% reduction in receptor alpha binding ($K_D$, pM), or exhibits no more than about a 35% reduction in receptor alpha binding ($K_D$, pM), or even exhibits no more than about a 30% reduction in receptor alpha binding ($K_D$, pM) when compared to IL-15.

Preferably, the long-acting IL-15 receptor agonist exhibits no more than about a 7-fold reduction in EC50 value (ng/mL, CTLL-2 pSTAT5) when compared to unmodified IL-15 and no more than about a 50% reduction in receptor alpha binding ($K_D$, pM) when compared to IL-15, including any one or more particular combinations of reductions in EC50 values or $K_D$ values described above.

Optionally, the long-acting IL-15 receptor agonist is comprised in a composition that comprises one or more pharmaceutically acceptable excipients. Exemplary excipients include, without limitation, those selected from the group consisting of carbohydrates, inorganic salts, antimicrobial agents, antioxidants, surfactants, buffers, acids, bases, amino acids, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, cyclodextrins, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The composition can also include an antimicrobial agent for preventing or deterring microbial growth. Nonlimiting examples of antimicrobial agents suitable for one or more embodiments of the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the conjugate or other components of the preparation. Suitable antioxidants for use in one or more embodiments of the present invention include, for example, ascorbyl palmitate, butylated hydroxyanisole, butylated hydroxytoluene, hypophosphorous acid, monothioglycerol, propyl gallate, sodium bisulfate, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (both of which are available from BASF, Mount Olive, New Jersey); sorbitan esters; lipids, such as phospholipids such as lecithin and other phosphatidylcholines, phosphatidylethanolamines (although preferably not in liposomal form), fatty acids and fatty esters; steroids, such as cholesterol; and IL-15 chelating agents, such as EDTA, zinc and other such suitable cations.

Acids or bases can be present as an excipient in the composition. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

One or more amino acids can be present as an excipient in the compositions described herein. Exemplary amino acids in this regard include arginine, lysine and glycine. Additional suitable pharmaceutically acceptable excipients include those described, for example, in the Handbook of Pharmaceutical Excipients, 7$^{th}$ ed., Rowe, R. C., Ed., Pharmaceutical Press, 2012.

The amount of the long-acting IL-15 R agonist comprised in the composition will vary depending on a number of factors, but will optimally be a therapeutically effective dose when the composition is stored in a unit dose container (e.g., a vial). In addition, a pharmaceutical preparation can be housed in a syringe. A therapeutically effective dose can be determined experimentally by repeated administration of increasing amounts of the long-acting IL-15 R agonist in order to determine an amount that produces a clinically desired endpoint as described herein. The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

The long-acting IL-15 R agonist is suitable for administering to a patient suffering from a condition that is responsive to treatment with interleukin-15. The method comprises administering to a patient, generally parenterally, a therapeutically effective amount of the long-acting IL-15 R agonist (preferably provided as part of a pharmaceutical composition). As previously described, the long-acting IL-15 R agonist may be administered parenterally (e.g., intramuscularly, subcutaneously, intravenously, or intraperitoneally). Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others. In some particular embodiments, the long acting IL-15 receptor agonist is provided in a formulation suitable for intravenous administration, and is administered intravenously. In some other embodiments, the long acting IL-15 receptor agonist is provided in a formulation suitable for subcutaneous administration, and is administered subcutaneously.

The method of administering the long acting IL-15 receptor agonist (e.g., provided as part of a pharmaceutical composition) can optionally be conducted so as to localize the agonist to a specific area. For example, liquid, gel and solid formulations comprising the agonist may also be surgically implanted in a diseased area (such as in a tumor, near a tumor, in an inflamed area, and near an inflamed area). Conveniently, organs and tissue can also be imaged in order to ensure the desired location is better exposed to the conjugate.

The method of administering may be employed to treat any condition that can be remedied or prevented by administration of the long-acting IL-15 R agonist, such as for example, cancer. For example, the long acting agonist can be used either alone or in combination with another pharmacotherapy to treat patients suffering from a condition that may be responsive to IL-15 therapy, such as for example, cancer.

As used herein in reference to treatment of a subject having cancer, the terms "treatment," "treat," and "treating" are meant to include the full spectrum of intervention for the cancer from which the subject is suffering, such as administration of the combination to alleviate, slow, stop, or reverse one or more symptoms of the cancer or to delay the progression of the cancer even if the cancer is not actually eliminated. Treatment can include, for example, a decrease in the severity of a symptom, the number of symptoms, or frequency of relapse, e.g., the inhibition of tumor growth, the arrest of tumor growth, or the regression of already existing tumors.

For example, an improvement in the cancer or a cancer-related disease may be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about a 10%, 20%, 30%, 40%, 50%, 60%, 70%, 80%, or 90% decrease in all measurable tumor burden (i.e., the number of malignant cells present in the subject, or the measured bulk of tumor masses or the quantity of abnormal monoclonal protein) in the absence of new lesions. The term "treatment" contemplates both a complete and a partial response.

The terms "cancer" and "cancerous" refer to or describe the physiological condition in mammals that is typically characterized by unregulated cell growth.

"Tumor" and "solid tumor" as used herein, refer to all lesions and neoplastic cell growth and proliferation, whether malignant or benign, and all pre-cancerous and cancerous cells and tissues.

Exemplary conditions are cancers, such as, for example, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, colon cancer, prostate cancer, squamous cell cancer, basal cell cancer, head and neck cancer, adenocarcinoma, sweat gland cancer, sebaceous gland cancer, papillary cancer, papillary adenocarcinomas, cystadenocarcinoma, medullary cancer, bronchogenic cancer, renal cell cancer, hepatoma, bile duct cancer, choriocarcinoma, seminoma, embryonal cancer, Wilms' tumor, cervical cancer, testicular cancer, lung cancer, small cell lung cancer, non-small cell lung cancer, bladder cancer, epithelial cancer, glioma, astrocytoma, medulloblastoma, craniopharyngioma, ependymoma, pinealoma, hemangioblastoma, acoustic neuroma, oligodendroglioma, meningioma, melanoma (including, for example, uveal melanoma, mucosal melanoma, and leptomeningeal melanoma), neuroblastoma, retinoblastoma, and leukemias.

In one particular method, the long acting IL-15 R agonist is used to treat a hematological malignancy such as leukemias or lymphoma. In yet another method, the long acting IL-15 R agonist is used to treat a solid cancer.

In some embodiments, the long acting IL-15 R agonist or composition is effective when administered at a therapeutically effective dose to a subject to stimulate NK activation and/or proliferation.

Figure 11A:
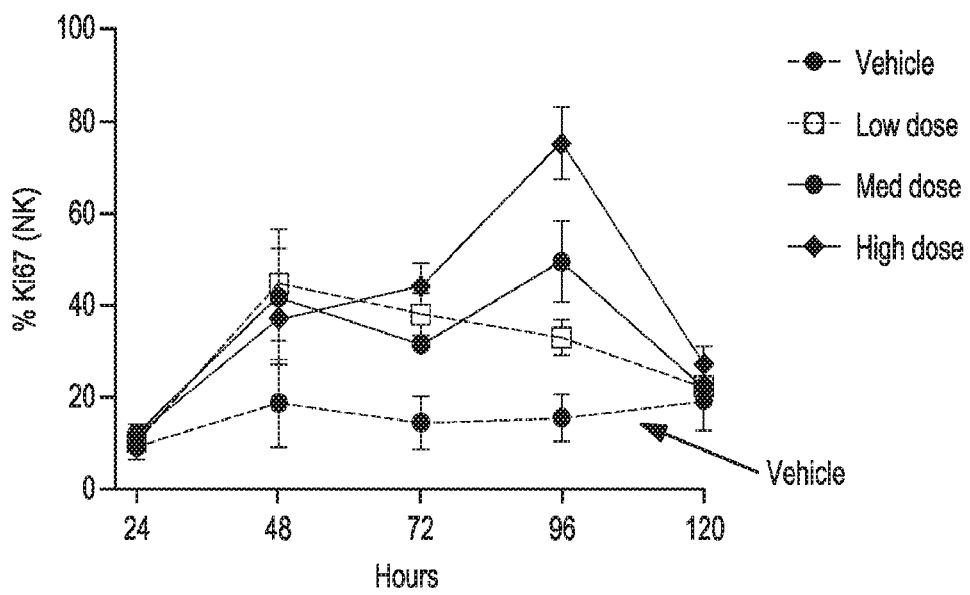
FIGS. 11A and 11B are plots illustrating NK cell proliferation in mice following i.v. administration of mono-mPEG-SBA40K-IL-15 (also referred to herein as Conjugate 1) at doses of 0.03 mg/kg (low dose, open squares), 0.3 mg/kg (medium dose, solid circles, solid line), or 1 mg/kg (high dose, diamonds) when compared to vehicle as described in Example 11.
Figure 12A:
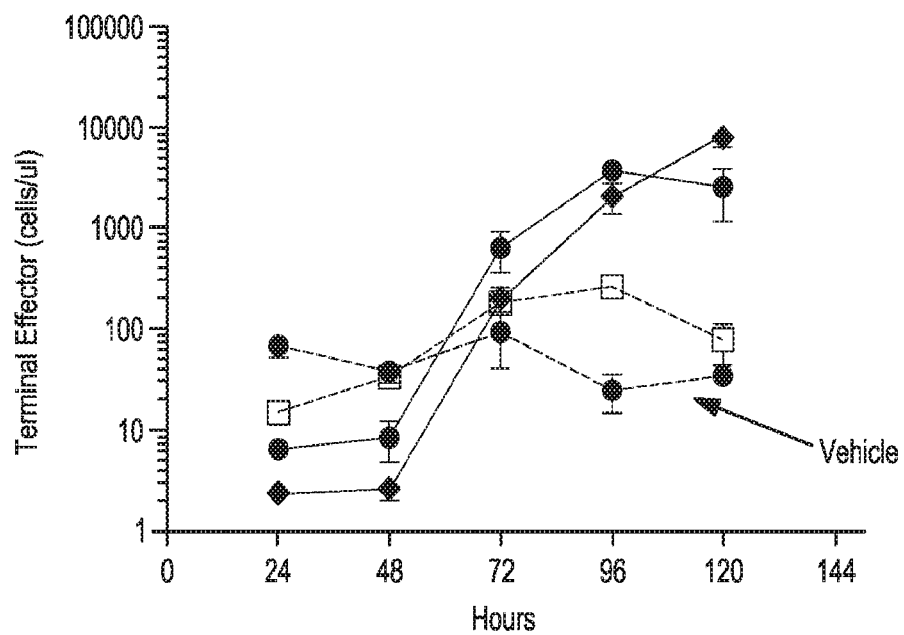
FIGS. 12A-D are plots illustrating increasing numbers of NK cells of all maturation levels in mice following i.v. administration of Conjugate 1 at doses of 0.03 mg/kg (low dose, open squares), 0.3 mg/kg (medium dose, solid circles, solid line), or 1.0 mg/kg (high dose, diamonds) compared to vehicle (solid circles, dashed line) as described in Example 11. Subsets of NK cells were defined by CD11b and CD27 expression.
Figure 12B:
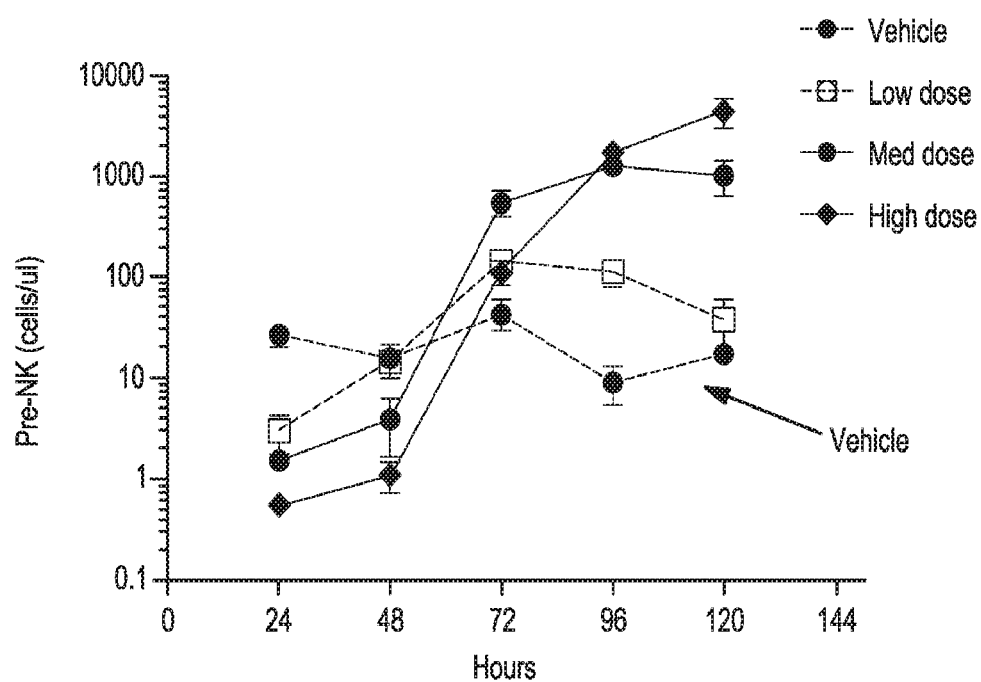
Figure 12C:
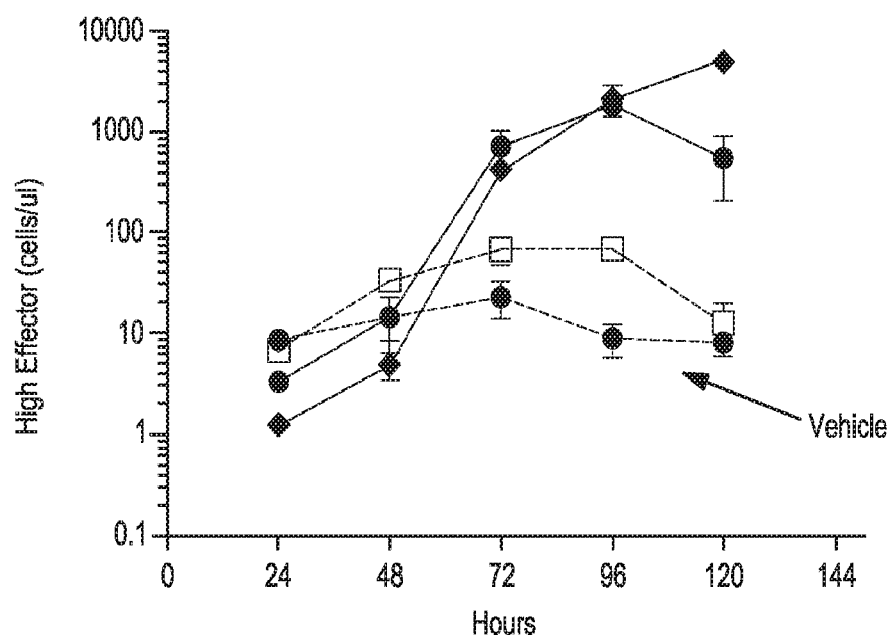
Figure 12D:
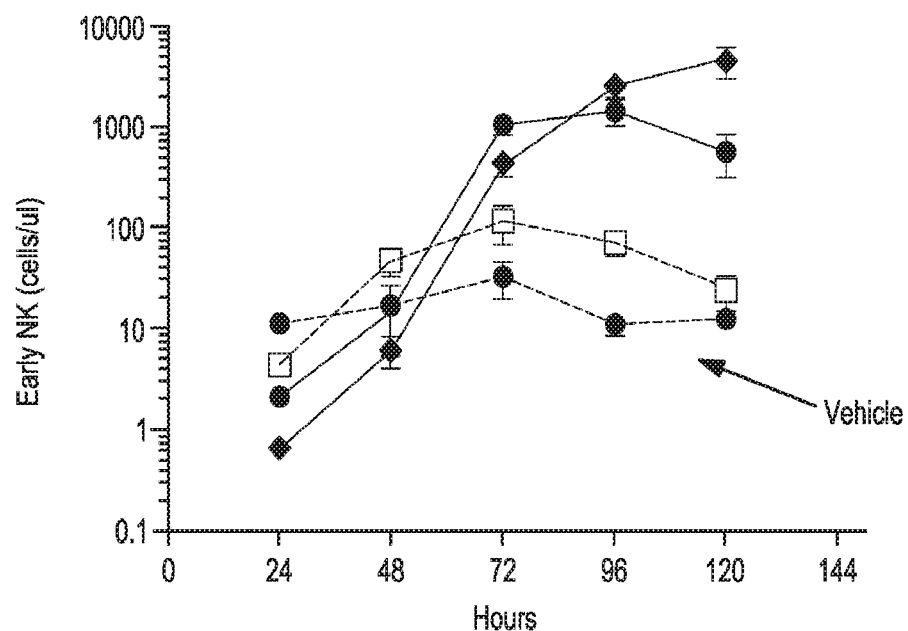

In an exemplary mouse model as described in Example 11, Conjugate 1 was effective to induce proliferation and a sustained increase in numbers of NK cells as shown by an increase in cell number (cells/μ as shown in FIGS. 12B-12C) as well as an increase in % Ki67 (e.g. FIG. 11A). % Ki67 is used as a marker for proliferating cells. As seen in FIGS. 12A-12D, the increase in cell number was seen in NK cells of all maturation levels (terminal effector cells, pre-NK cells, high effector cells and early NK cells). As shown in Example 17, the increase in NK cell number was sustained at all dose levels for at least 96 hours with the medium and high dose levels being sustained for at least 144 hours. Administration of Conjugate 1 in the mouse model induced in increase in % Ki67 at all dose levels, as compared to vehicle, which was sustained for at least 120 hours. % Ki67At least the medium dose ranges (e.g. 0.1 mg/kg and 0.3 mg/kg) induced an increase in % Ki67 that was sustained for at least 144 hours.

Figure 28A:
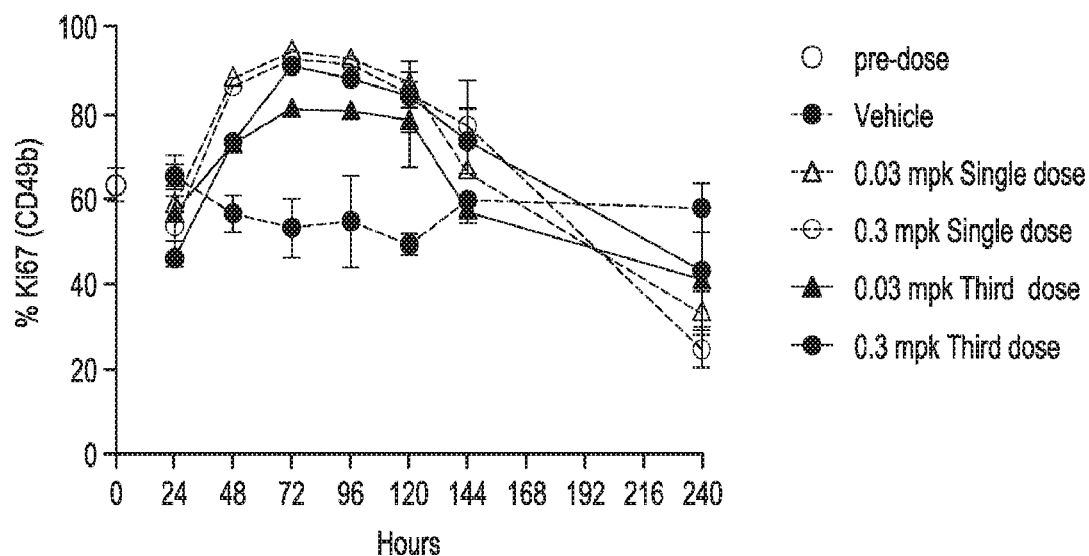
FIGS. 28A-D are plots illustrating increasing numbers of NK cells of all maturation levels in mice following i.v. administration of Conjugate 1 at doses of 0.03 mg/kg and 0.3 mg/kg on a single dose or following the third dose in a q7dx3 schedule, as described in Example 11.
Figure 28B:
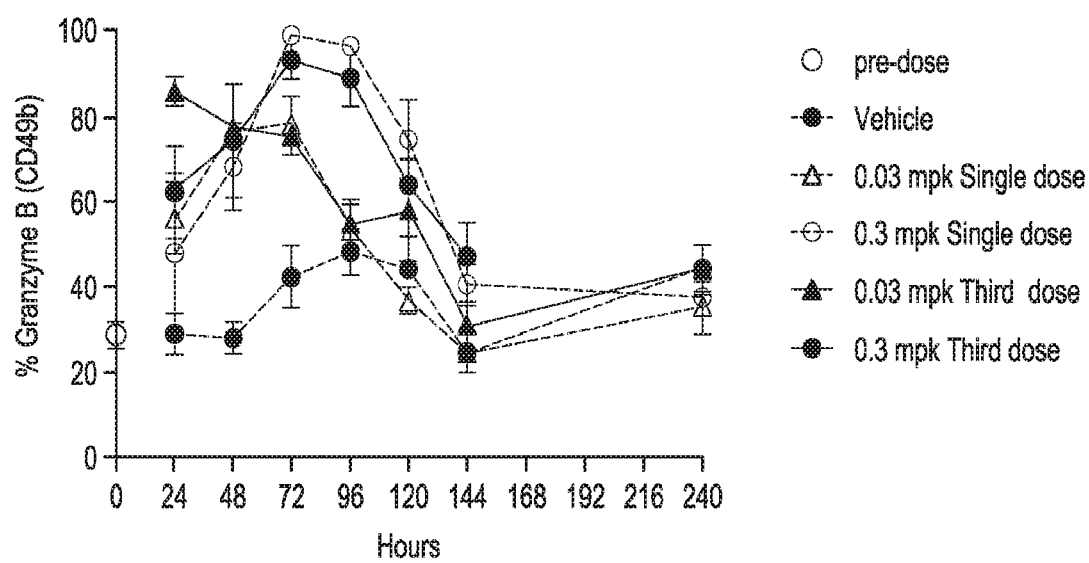
Figure 28C:
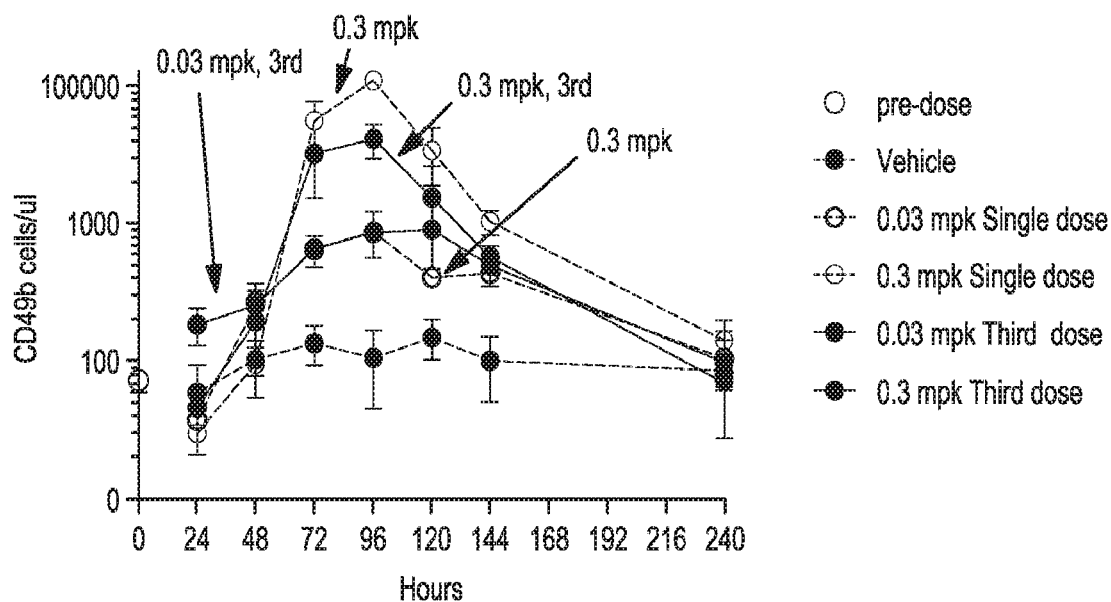
Figure 28D:
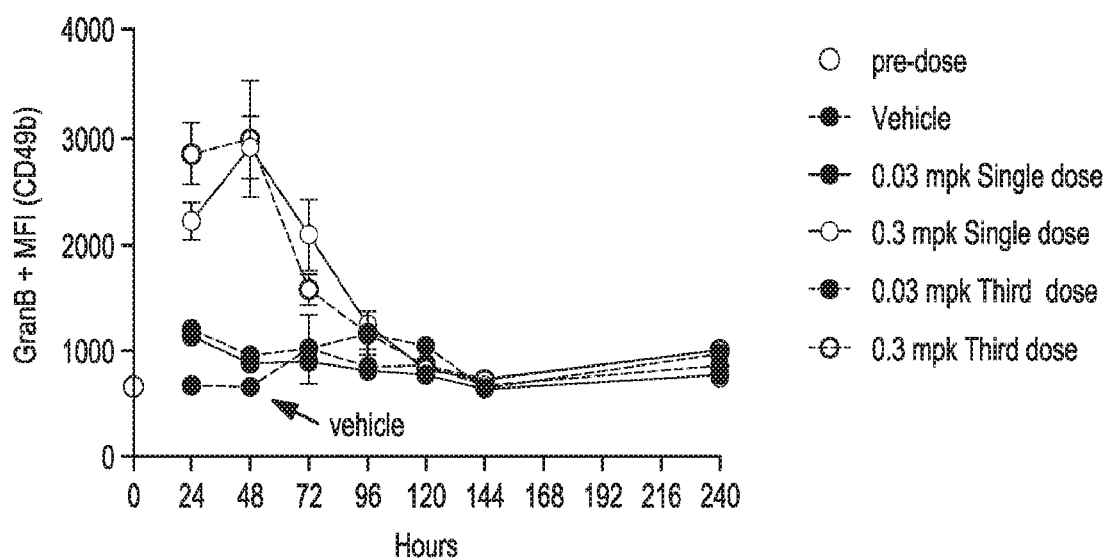

The effects of Conjugate 1 may be induced and sustained with a single dose. In an exemplary murine model as described in Example 11, the increase in cell number was induced and sustained with administration of a single dose of Conjugate 1. A single dose induced and sustained % Ki67 levels in murine CD49b cells comparable to repeated (e.g. Q7dx3) dosing at the same level (see FIG. 28A).

Figure 48A:
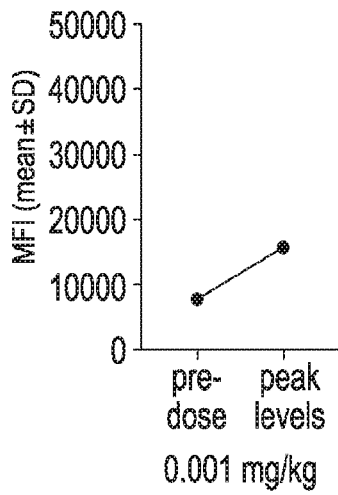
FIGS. 48A, 48B, and 48C are plots illustrating Granzyme B expression as a function of time following treatment with Conjugate 1 at doses of 0.001 mg/kg (FIG. 48A), 0.01 mg/kg (FIG. 48B) and 0.1 mg/kg (FIG. 48C) as described in Example 28. This data indicates that treatment with Conjugate 1 increases levels of Granzyme B in NK cells in non-human primates (NHPs).
Figure 48B:
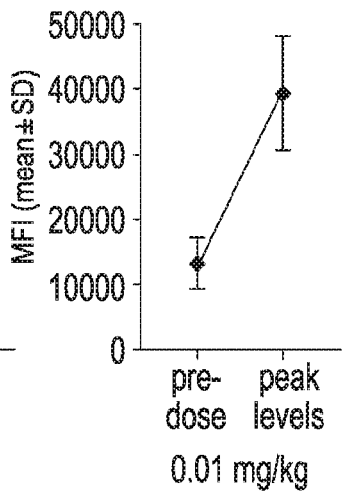
Figure 48C:
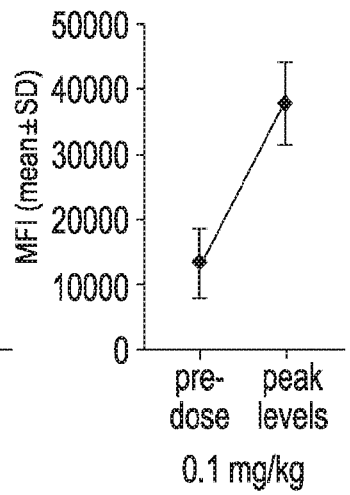
Figure 49A:
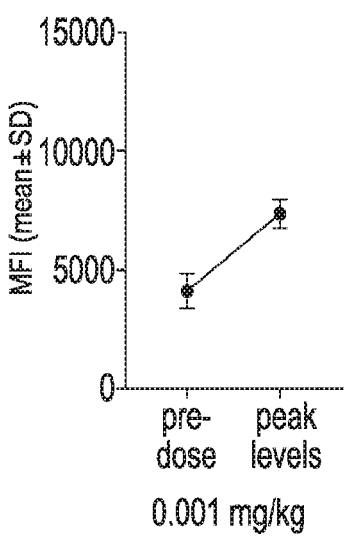
FIGS. 49A, 49B, and 49C are plots illustrating Perforin expression as a function of time following treatment with Conjugate 1 at doses of 0.001 mg/kg (FIG. 49A), 0.01 mg/kg (FIG. 49B) and 0.1 mg/kg (FIG. 49C) as described in Example 28. This data indicates treatment with Conjugate 1 increases levels of Perforin in NK cells in NHPs.
Figure 49B:
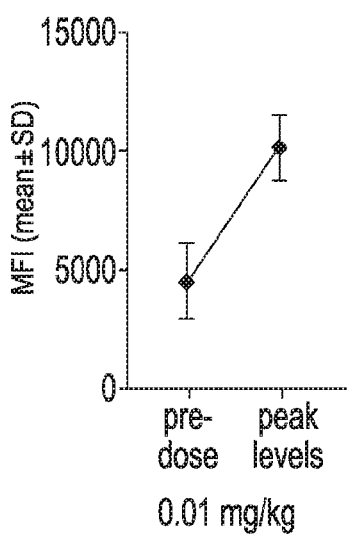
Figure 49C:
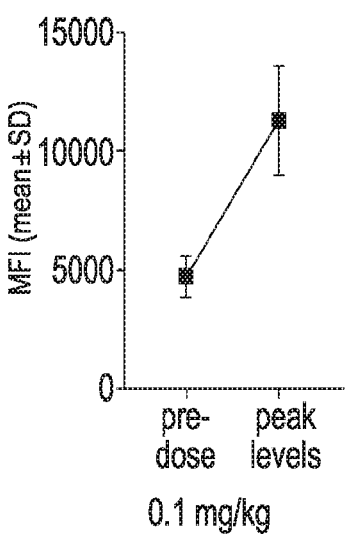

In some further embodiments, the long acting IL-15 R agonist or composition is effective, when administered at a therapeutically effective dose to increase NK cell activation as evidenced by an increase in cytotoxic protease expression by NK cells. In an exemplary non-human primate model as described in Example 28, the expression of the NK cytolytic enzymes Granzyme B and Perforin was induced and enhanced by a single dose of Conjugate 1. As seen in FIGS. 48A-48C, all dose levels increased Granzyme B expression and the mid/higher doses at least tripled the expression (MFI) as compared to pre-dose levels. As seen in FIGS. 49A-49C, all dose levels increased Perforin expression and the mid/higher doses doubled the expression (MFI) as compared to pre-dose levels. Thus, Conjugate 1 is effective to increase the cytotoxicity of NK cells.

In yet some further embodiments, the long acting IL-15 R agonist or composition is effective when administered at a therapeutically effective dose to a subject to support CD8 T-cell survival and memory formation.

Figure 30A:
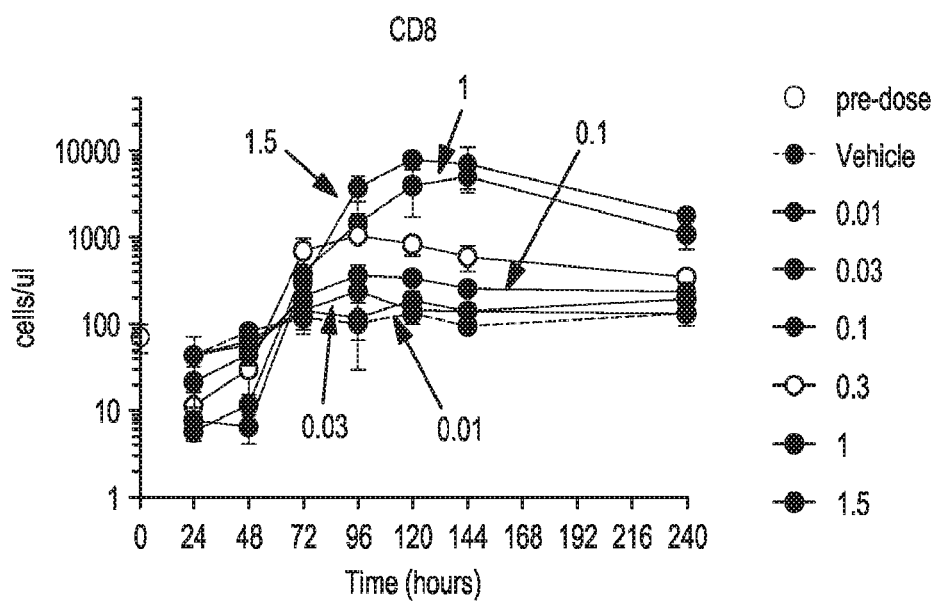
FIGS. 30A-C are plots of total CD8, CD8 central memory (Tcm) and CD8 effector memory (Tem) cell numbers, respectively, after a single administration of Conjugate 1 at 0.01, 0.03, 0.1, 0.3, 1 or 1.5 mg/kg, as described in Example 17. Conjugate 1 at dose levels equal to or greater than 0.03 induce a significant increase in total CD8 T cells in the blood as described in Example 17. The lowest dose of 0.01 mg/kg increased CD8 Tcm and CD8 Tem. At 0.3 mg/kg, Conjugate 1 increased CD8, CD8 Tcm and CD8 Tem by 6.4×, 37.9× and 14.5×, respectively. Notably, CD8 and CD8 memory T cell numbers did not return to baseline at 240 hours post injection when Conjugate 1 was dosed at 0.3-1.5 mg/kg, demonstrating the sustained PD effects of Conjugate 1.
Figure 30B:
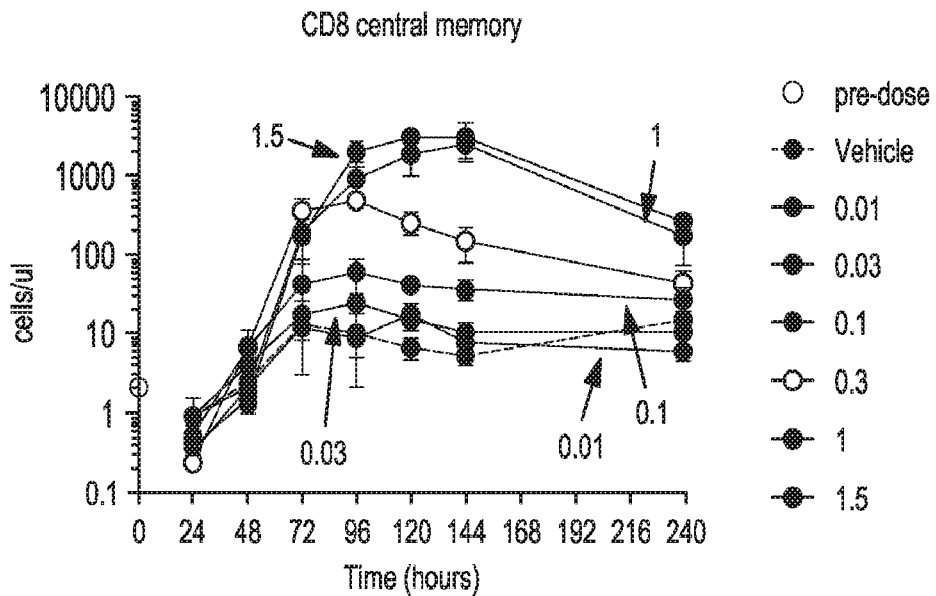
Figure 30C:
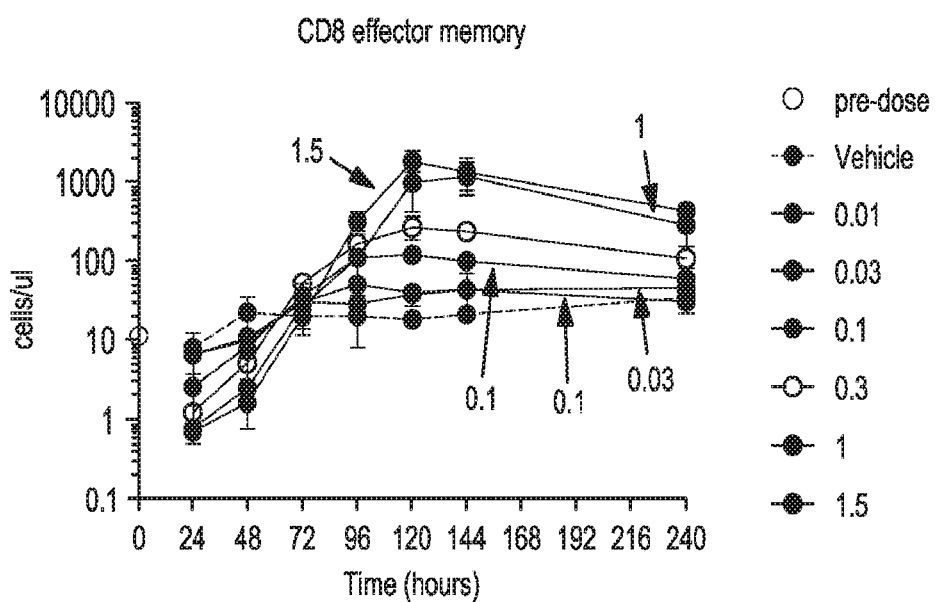
Figure 30D:
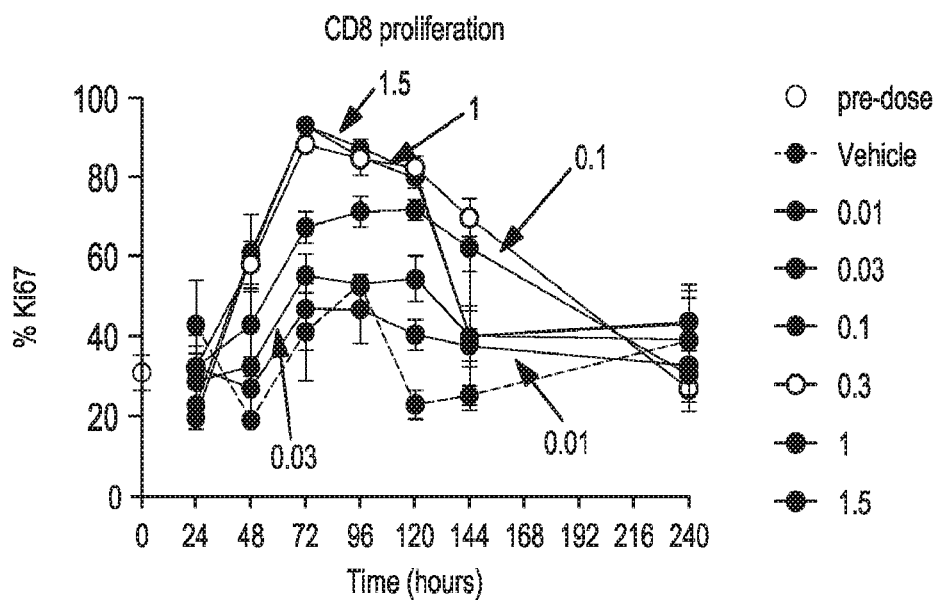
FIGS. 30D, 30E and 30F are plots of Ki-67 percent positivity within total CD8, CD8 Tcm and CD8 Tem populations, respectively, in mice, as described in Example 17. A single dose of Conjugate 1, at all dose levels, increases Ki-67 positivity in all CD8 and CD8 subpopulations.
Figure 30E:
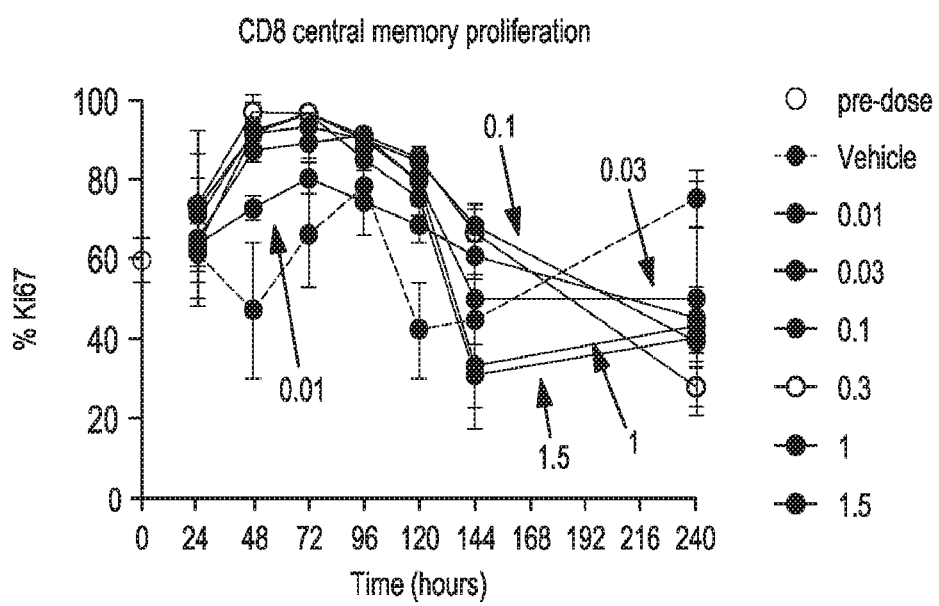
Figure 30F:
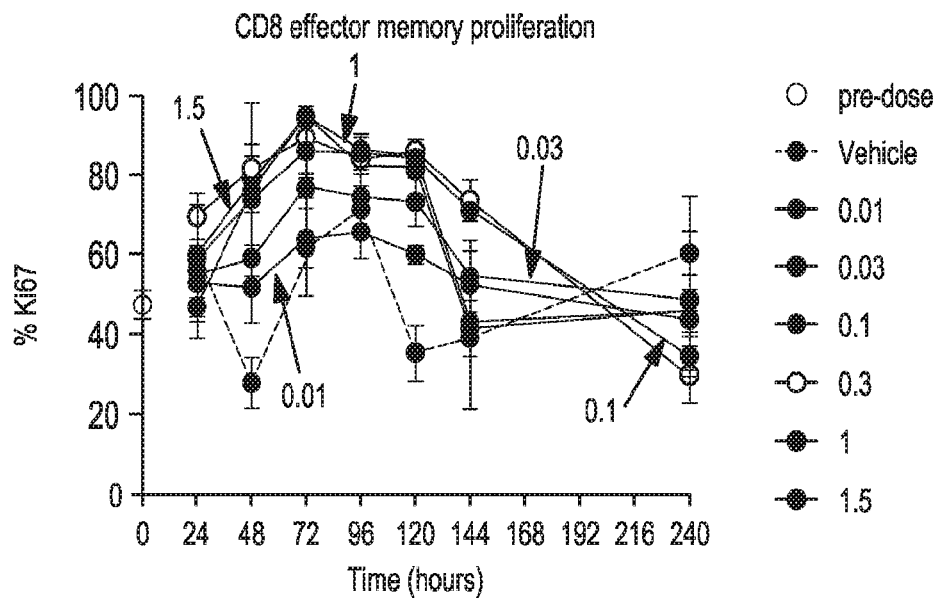

In an exemplary mouse model, a single dose at all dose levels of Conjugate 1 increases cellular proliferation as shown by an increase in % Ki-67 positivity in CD8 cells (FIG. 30D) as well as in central memory and effector memory CD8 subpopulations (FIGS. 30E-30F). As shown in Example 17, administration of Conjugate 1 in a murine model induced a significant increase in total CD8 T cells in the blood (see FIG. 30A). The lowest dose increased CD8 Tcm and CD8 Tem (see FIGS. 30B-30C). In an exemplary murine model, a single iv injection of Conjugate 1 maintained increased cell numbers, as compared to administration of a vehicle, for at least 240 hours (see FIG. 30A for example). Notably, CD8 and CD8 memory T cell numbers did not return to baseline at 240 hours post injection when Conjugate 1 was administered at some dose levels. Thus, Conjugate 1 maintains populations of CD8+ memory T cells for an extended period. A single dose of Conjugate 1, at all dose levels, also increased Ki-67 positivity in all CD8 and CD8 subpopulations indicating increased proliferation of these cells. Repeated dosing with Conjugate 1 resulted in further increases in CD8, CD8 Tcm, and CD8 Tem populations (see FIGS. 31A-31C). The repeated dosing also resulted in long term increases in the cellular proliferation of at least 240 hours for each of the CD8, CD8 Tcm, and CD8 Tem populations in mice.

Conjugate 1 also induced proliferation and a sustained increase in numbers of NK cells and CD8 T cells in a non-human primate model (cynomolgus monkey model in Example 27), as compared to administration of the vehicle. Each dose level of Conjugate 1 induced and sustained the increase in NK cell numbers for at least 14 days (see FIG. 44A). Conjugate 1 induced and sustained an increase in CD8 T cell numbers for at least 10 days at each dose level.

In yet one or more further embodiments, the IL-15 R agonist is administered intravenously. In even further embodiments, the IL-15 R agonist is administered subcutaneously.

In yet some further embodiments, upon administration, the IL-15 R agonist is effective to induce sustained signaling in lymphocytes resulting in proliferation of CD8 T-cells and/or a preferential expansion of the CD8 central memory population.

The actual dose to be administered will vary depending upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day. A given dose can be periodically administered up until, for example, the clinician determines an appropriate endpoint (e.g., cure, regression, partial regression, and so forth) is achieved.

In some embodiments, the therapeutically effective dose ranges from about 0.25-25 mcg/kg. In other embodiments, the therapeutically effective dose ranges from about 0.25 mcg/kg to about 0.1 mg/kg, about 0.01 mg/kg to about 0.1 mg/kg per day or about 0.03 mg/kg to about 0.1 mg/kg per day or. In other embodiments, the therapeutically effective dose ranges from about 1-10 mcg/kg, about 0.03 mg/kg to about 0.1 mg/kg. In some specific, but not limiting embodiments, the therapeutically effective dose is about 0.25 mcg/kg, 0.3 mcg/kg, 0.5 mcg/kg, 1 mcg/kg, 2 mcg/kg, 3 mcg/kg, 5 mcg/kg, 6 mcg/kg, 7 mcg/kg, 10 mcg/kg, 15 mcg/kg, 20 mcg/kg, 25 mcg/kg, 0.01 mg/kg, 0.03 mg/kg, 0.05 mg/kg, or 0.1 mg/kg. With reference to the doses referenced in the examples herein, one of ordinary skill in the art could convert the animal doses (e.g. mouse) to a corresponding dose in humans using conversions as known in the art (e.g. Nair et al., J. Basic and Clin. Pharmacy (2016) 7:27-31).

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration once daily, three times weekly, twice weekly, once weekly, twice monthly (e.g. q/14 days), once monthly (e.g. q/30 or 31 days or q/21 days), and any combination thereof. Once a desired clinical endpoint has been achieved, dosing of the composition is halted or reduced. In some embodiments, the unit dose of any given conjugate may be administered once to provide sustained effect.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of this disclosure will be apparent to those skilled in the art to which the invention pertains.

All articles, books, patents and other publications referenced herein are hereby incorporated by reference in their entireties. In the event of an inconsistency between the teachings of this specification and the art incorporated by reference, the meaning of the teachings and definitions in this specification shall prevail (particularly with respect to terms used in the claims appended herein). For example, where the present application and a publication incorporated by reference defines the same term differently, the definition of the term shall be preserved within the teachings of the document from which the definition is located.

EXAMPLES

It is to be understood that the foregoing description as well as the examples that follow are intended to illustrate and not limit the scope of the invention(s) provided herein. Other aspects, advantages and modifications will be apparent to those skilled in the art to which this disclosure pertains.

In the following examples, efforts have been made to ensure accuracy with respect to numbers used (e.g., amounts, temperatures, etc.) but some experimental error and deviation should be taken into account. Unless indicated otherwise, temperature is in degrees C. and pressure is at or near atmospheric pressure at sea level. Each of the following examples is considered to be instructive to one of ordinary skill in the art for carrying out one or more of the embodiments described herein.

Materials and Methods

Recombinant IL-15 ("rIL-15") SEQ ID NO: 1 (as provided in FIG. 1), prepared using conventional techniques, was used in the following examples, although any suitable IL-15 moiety may be similarly employed. SEQ ID NO:1, a recombinant human IL-15 from *E. coli*, is a single, non-glycosylated polypeptide chain containing 115 amino acids, with a molecular weight of 12.9 kDa.

The reactive polymer reagent, linear mPEG-succinimidyl butanoate, 40 kDa ("mPEG-SBA"), has the following structure,

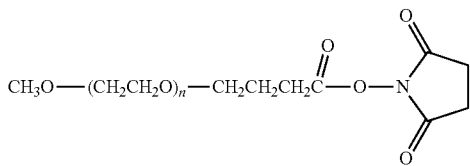

where n corresponds to the number of monomer subunits to provide a polymer having a weight average molecular weight of about 40 kilodaltons, i.e., where n is ~909. Additional mPEG-succinimidyl butanoate reagents suitable for use include those having weight average molecular weights, for example, of about 10 kD, 15 kD, 20 kD, 25 kD, 30 kD, 40 kD, 50 kD or 60 kD. This activated polymer reagent, when reacted with amino groups of IL-15 (e.g., lysines or the N-terminal), is effective to form a stable amide linkage between the IL-15 moiety and the polyethylene glycol moiety.

The reactive fluorenyl-PEG reagent, PEG2-CAC-FMOC-20kD-NHS, has the following structure:

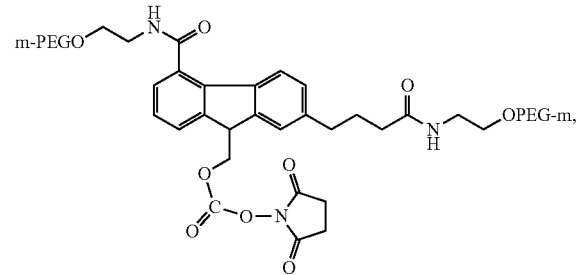

where mPEG is methoxy(polyethylene glycol) and the weight average molecular weight of the polymer reagent is about 20 kilodaltons (i.e., with each mPEG moiety having a weight average molecular weight of about 10 kilodaltons). Additional PEG2-CAC-FMOC reagents having different molecular weights are named accordingly, e.g., PEG2-CAC-FMOC-10kD-NHS, PEG2-CAC-FMOC-15kD-NHS, PEG2-CAC-FMOC-30kD-NHS, PEG2-CAC-FMOC-40kD-NHS, where such reagents have the structure shown above and differ only in the molecular weight of the "mPEG" moieties attached to the FMOC core.

SDS-PAGE Analysis

Samples were analyzed by sodium dodecyl sulfate-polyacrylamide gel electrophoresis (SDS-PAGE) using Invitrogen gel electrophoresis system (XCell SureLock Mini-Cell). Samples were mixed with sample buffer. Then, the prepared samples were loaded onto a NuPAGE Novex precast gel and run for approximately thirty minutes.

RP-HPLC Analysis

Reversed-phase chromatography (RP-HPLC) analysis was performed on an Agilent 1200 HPLC system (Agilent). Samples were analyzed using a Poroshell 300SB-C3 column (2.1×75 mm, Agilent) at 60° C. The mobile phases used were 0.1% TFA/H20 (A) and 0.1% TFA/CH3CN (B). The flow rate for the column was 0.5 ml/min. Eluted protein and PEG-protein conjugates were detected using UV at 280 nm.

Bioassays

Potency Assay (Mouse T Cell) Based on STAT5 Phosphorylation in CTLL-2 Cells

In the phospho-STAT5 assay following receptor binding, downstream cell signaling can then activate Signal Transducer and Activator of Transcription 5 (STAT5) through phosphorylation to promote gene expression to induce cell proliferation. The activation of phosho-STAT5 is measured in CTLL-2 cells, a murine T lymphocyte cell line, using the phospho-STAT5/total STAT5 multiplexed assay (Meso Scale Discovery, MD) in response to sample and reference treatment for ~10 minutes.

One day prior to the assay, CTLL-2 cells were split into fresh growth medium [RPMI 1640 supplemented with 10% FBS, 10% T-cell culture supplement (catalog #354115, Corning, Inc., Tewksbury, MA), 2 mM L-glutamate, and 1 mM sodium pyruvate]. On the day of assay, cells were pre-incubated in assay medium (RPMI 1640 supplemented with 1% FBS, 2 mM L-glutamate, and 1 mM sodium pyruvate) for at least four hours, and then plated in assay medium in a 96-well plate at 50,000 cells/well. Dilutions of the test article were prepared in an appropriate buffer immediately prior to assay. Stimulation of CTLL-2 cells was initiated by the transfer of 25× test article solutions to triplicate wells containing CTLL-2 cells. Plates were incubated at 37° C., 5% $CO_2$ for 10 minutes, and the reaction was stopped by cell lysis. Detection of phospho-STAT5 and total STAT5 protein levels in cell lysates was performed using the MSD Phospho(Tyr694)/Total STATa,b Whole Cell Lysate Kit (Meso Scale Discovery, MD). Following a 10-minute treatment, recombinant human IL-15 obtained from Pepro-Tech demonstrated IL-15 activity by inducing STAT5 phosphorylation in CTLL-2 cells with an average ECso of 0.27 ng/mL, which served as the control.

HuPBMC-pStat5 Assay

The potency of IL-15 or long acting IL-15 R agonists on various human lymphocyte subpopulations was determined by phospho-STAT5(Y694) dose response assay. Frozen human PBMCs from multiple donors were supplied by AllCells. $1 \times 10^6$ cells/100 ul were cultured in complete RPMI media for 2 hours and then incubated with the indicated concentrations (10,000 ng/ml-0.001 ng/ml serial dilutions) of IL-15 or conjugates for 20 minutes at 37 c. The cells were then fixed (using BD Cytofix) and permeabilized (using 100% pre-chilled methanol) and stained with antibodies for CD3, CD4, CD8, CD4-Tregs(CD4+CD25+Foxp3+), CD56 and phosphorylated STAT5(Y694) before analysis by flow cytometry. Concentration-response relationships were used to calculate the $EC_{50}$ values.

Receptor Affinities of Long Acting rIL-15 Receptor Agonists for IL-15Rα

The affinities of IL-15 and exemplary long acting rIL-15 receptor agonists were measured using Surface Plasmon Resonance ("SPR") using a BIAcore™ SPR system. Briefly, the surface of a Biacore CM5 sensor chip was activated using a 1:1 mixture of NHS:EDC to generate active NHS esters. Goat anti-human Fc antibody was covalently attached to the surface by injecting it for five minutes in 10 mM sodium acetate (pH 4). There were approximately 8000 RU of antibodies bound to the surface. Any remaining NHS ester was then quenched with ethanolamine.

At the initiation of each injection cycle, IL-15-Rα-Fc was captured on a sensor chip channel by a five-minute injection step in PB SP. Typically, 150-200 RU of receptors were bound on the surface.

Long acting rIL-15 receptor agonist test articles were diluted to 10 μM in PBS (containing 0.05% Tween 20 and 0.1 mg/ml BSA). A series of 3-fold dilutions were made and injected onto a sensor chip which was coated with IL-15Rα. The affinities were measured by determining the $k_a$ and $k_d$ rates separately, and the ratio between $k_d$ and $k_a$ was used to calculate the $K_d$ values.

Example 1

Preparation of a Long Acting IL-15 Receptor Agonist

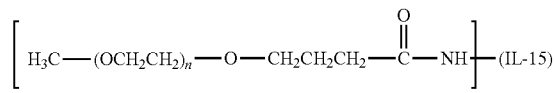

Mono(methoxyPEG-N-butanamide)$_{40kD}$Interleukin-15

Experiment 1: A 2.7 ml solution of IL-15 (1.23 mg/ml in PBS buffer, pH 7.4) was transferred to a small reaction vial. 300 μl of 0.6 M borate buffer at pH 8 was added to adjust the pH to pH 8. mPEG-SBA, 40 kDa, stored at ~20° C. under nitrogen, was warmed to ambient temperature. A ten-fold excess (relative to the molar amount of IL-15) of mPEG-SBA-40K was dissolved in 2 mM HCl to form a 10% PEG reagent solution. The 10% PEG reagent solution was quickly added to the IL-15 solution and mixed well. After the addition of the mPEG-SBA-40K, the pH of the reaction mixture was determined and adjusted to pH 8 using conventional techniques. To allow for coupling of the mPEG-SBA-40K to IL-15 (i.e., via formation of a stable amide linkage), the reaction solution was placed on a Slow Speed Lab Rotator for 1.5 hours to facilitate conjugation at room temperature. The reaction was quenched by addition of a solution of glycine.

FIG. 2 shows the chromatogram following RP-HPLC analysis of the conjugation reaction mixture. The reaction yielded 40% mono-conjugate (i.e., having a single PEG moiety attached to IL-15), 24% di-conjugate (having two PEGs attached to IL-15) and 6% tri-conjugate (having three PEGs attached to IL-15) species. Approximately 30% unreacted IL-15 remained in the reaction mixture although reaction conditions were not optimized.

The desired mono-conjugate was separated/isolated by anion-exchange chromatography using a Q Sepharose High Performance column and sodium phosphate buffers as the eluent phase. The purified mono-mPEG-SBA40K-IL-15 conjugate (also referred to herein as mono-mPEG-butanamide-40K-IL-15 or mono(methoxyPEG-N-butanamide)$_{40KD}$interleukin-15, or mono-mPEG$_{40K}$-C4-amide-IL-15), was characterized by HPLC and SDS-PAGE. For the remainder of the Examples, purified mono-mPEG-SBA40K-IL-15 is referred to as Conjugate 1.

Figure 3:
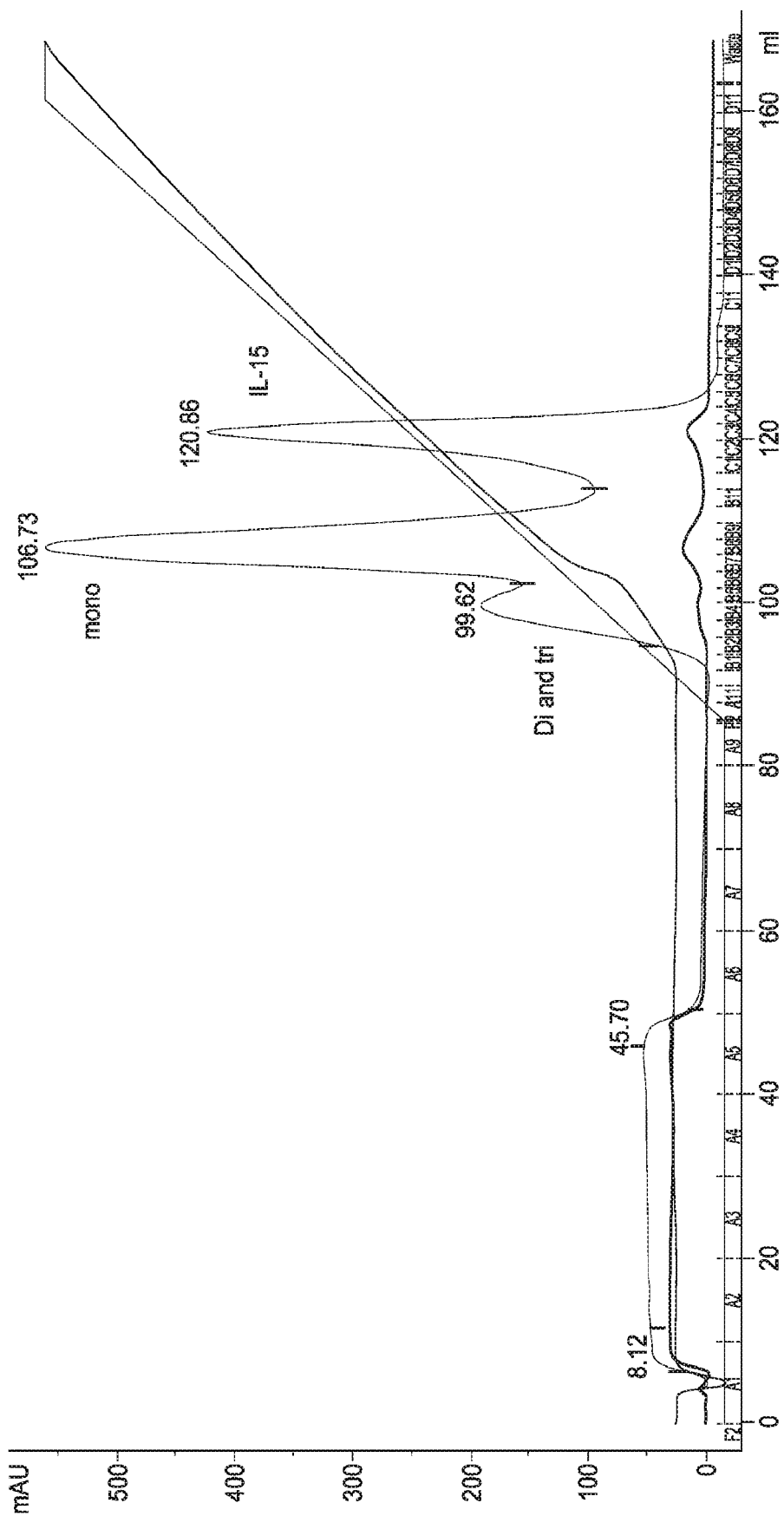
FIG. 3 is an FPLC purification profile from an anion-exchange chromatography column as described in Example 1.
Figure 4:
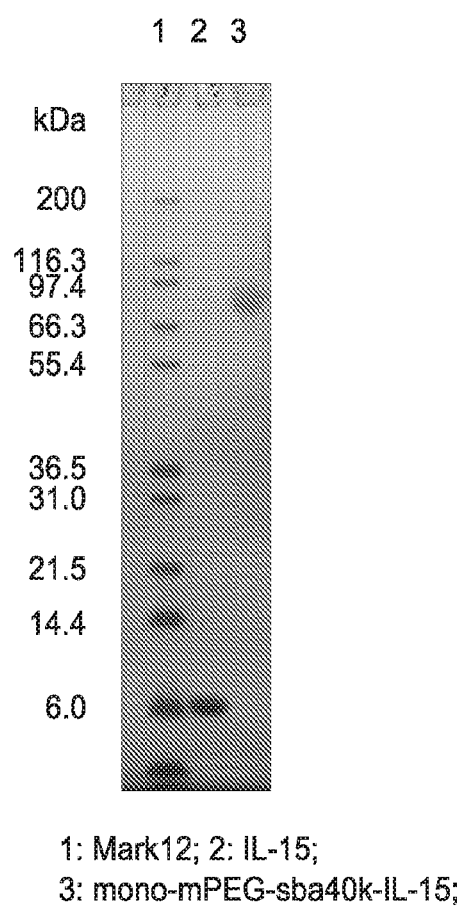
FIG. 4 is an SDS-PAGE of an exemplary purified long-acting IL-15 receptor agonist, mono-mPEG-butanamide-IL-15, as described in Example 1. Lane 1 provides molecular weight markers as indicated; Lane 2 is the unconjugated parent molecule, IL-15, and Lane 3 is mono-mPEG-butanamide-IL-15.
Figure 5:
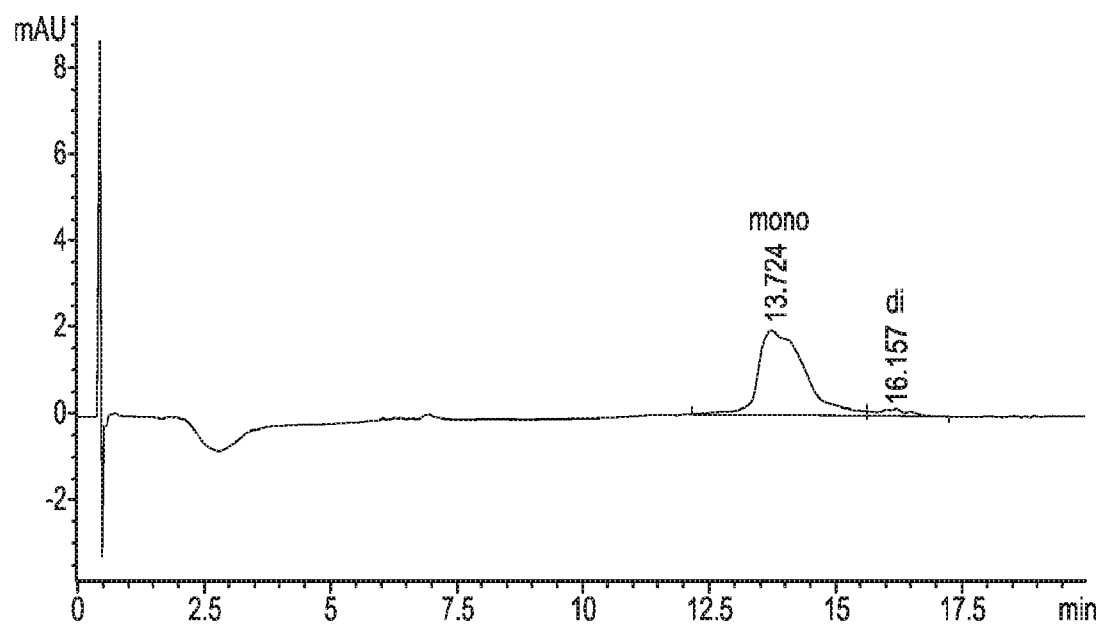
FIG. 5 is a RP-HPLC analysis of purified mono-mPEG-butanamide-IL-15, as described in Example 1.

FIG. 3 provides an FPLC purification profile from an anion-exchange chromatography column. FIG. 4 shows an SDS gel of purified mono-mPEG-SBA-40K-IL-15 conjugate. As indicated by gel, the purified conjugate possesses a high level of purity and is free of unreacted IL-15. FIG. 5 shows the RP-HPLC analysis of purified mono-mPEG-SBA-40K-IL-15. As can be seen from the HPLC result, the purified mono-mPEG-SBA-40K-IL-15 composition contains less than about 10% (molar amount) of di- or higher level conjugates.

Using this same approach, conjugates such as mono-mPEG-SBA-10K-IL-15, mono-mPEG-SBA-15K-IL-15, mono-mPEG-SBA-20K-IL-15, mono-mPEG-SBA-25K-IL-15, mono-mPEG-SBA-30K-IL-15; mono-mPEG-SBA-40K-IL-15; mono-mPEG-SBA-50K-IL-15; and mono-mPEG-SBA-60K-IL-15 are prepared using mPEG-SBA having different weight average molecular weights.

Experiment 2: An approximately 2 mg/ml solution of IL-15 in a buffer (50 mM sodium phosphate, 100 mM sodium chloride, 10% sucrose, pH 7.4) was transferred to each of two different reaction vessels (referred herein as Composition 1 and Composition 2). To adjust the pH to 8.0, a Borate buffer (0.4M or 0.6M) at pH 8 was added. A ten-fold excess (relative to the molar amount of IL-15) of m PEG-SBA-40K (mPEG-SBA, 40 kDa), diluted in 2 mM HCl, was added to each of the IL-15 solutions and mixed well. After the addition of the mPEG-SBA-40K, the pH of the reaction mixture was determined to be pH 8, or adjusted if necessary by use of additional borate buffer. The final concentration of the IL-15 in the reaction was targeted for 1 g/L, if necessary using an additional diluent (a buffer containing 50 mM sodium phosphate, 100 mM sodium chloride, 10% sucrose, pH 7.4 was used for Composition 1 and water was used for Composition 2). To allow for coupling of the m PEG-SBA-40K to IL-15 (i.e., via formation of predominantly stable amide linkages), the reaction solution was mixed for 45 or 60 minutes to facilitate conjugation at room temperature for Composition 1 or Composition 2, respectively. The reaction was quenched by addition of a 71-fold excess of glycine relative to the molar amount of PEG initially added to the reaction at pH 8.0 for 30 minutes. For Composition 1, the pH was adjusted by titrating to pH 7.0 using a 0.2 M phosphoric acid.

The resulting composition was characterized by reverse phase HPLC (RP-HPLC), SDS-PAGE, and ion exchange HPLC (IEX-HPLC). The results of the RP-HPLC analysis are provided in Table 1A below.

TABLE 1A

|  | Component | Average % Area |
|---|---|---|
| Composition 1 | IL-15 | 0.57 |
|  | Mono-PEGylated IL-15 | 82.66 |
|  | RRT1 = Peak T1 (not characterized) | 8.05 |
|  | RRT2 = Peak T2 (not characterized) | 5.17 |
|  | RRT3 = Peak T3 (not characterized) | 3.57 |
| Composition 2 | IL-15 | 0.36 |
|  | Mono-PEGylated IL-15 | 92.17 |
|  | RRT1 = Peak T1 (not characterized) | 2.26 |
|  | RRT2 = Peak T2 (not characterized) | 3.28 |
|  | RRT3 = Peak T3 (not characterized) | 1.93 |

RRT is relative retention time.
The results of the SEC-HPLC analysis are provided in Table 1B, below.

The results of the IEX-HPLC analysis are provided in Table 1B, below.

TABLE 1C

|  |  | Average % Area |
|---|---|---|
| Composition 1 | Basic region | 10.20 |
|  | Main peak | 68.53 |
|  | Acidic region | 21.29 |
| Composition 2 | Basic region | 10.43 |
|  | Main peak | 56.32 |
|  | Acidic region | 33.26 |

The compositions prepared predominantly comprised the mPEG-SBA-40K monoPEGylated species with less than 10% of the PEG dimer (i.e., having 2 PEG moieties attached to IL-15) and even lower amounts of the higher PEG species (i.e. having 3 or more PEG moieties attached to IL-15).

Further, the compositions had a relatively low degree of deamidation (identified as the "Acidic region" in Table 1C). Composition 1 was 21.29% deamidated and Composition 2 was 33.26% deamidated.

Example 2

Preparation of a Long Acting IL-15 Receptor Agonist

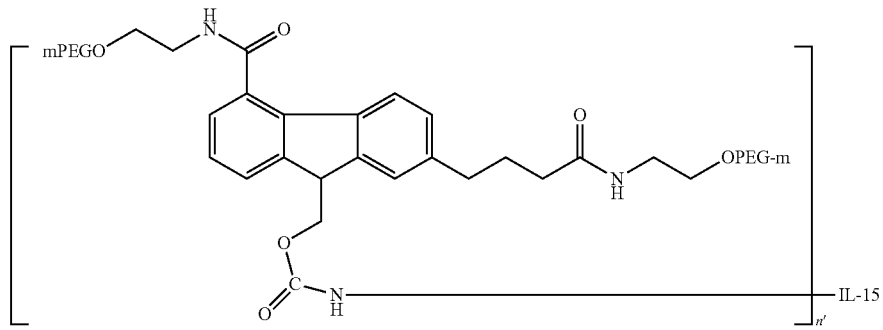

TABLE 1B

|  | Component | Average % Area |
|---|---|---|
| Composition 1 | HMW species | 5.56 |
|  | Di-mPEG IL-15 (dimer) | 15.46 |
|  | Mono-mPEG IL-15 (monomer) | 78.98 |
| Composition 2 | HMW mPEG species | 5.25 |
|  | di-mPEG IL-15 | 6.62 |
|  | Mono-mPEG IL-15 | 88.14 |

HMW = high molecular weight mPEG-IL-15 conjugates having 3 or more PEGs covalently attached to interleukin-15.

mPEG2-CAC-fmoc-20K-NHS, stored at −80° C. under nitrogen, was warmed to ambient temperature under nitrogen purging. A stock solution (200 mg/mL) of mPEG2-CAC-fmoc-20K-NHS was prepared in 2 mM HCl, and mPEG2-CAC-fmoc-20K-NHS was added to the rIL-15 with molar ratios of mPEG2-CAC-fmoc-20K-NHS to rIL-15 ranged from 5:1 of 100:1. The final concentration of rIL-15 in the mixture was 0.5 mg/mL (0.031 mM). Sodium bicarbonate buffer (1 M, pH 8.0) was added to the mixture to reach a final concentration of 100 mM, and conjugation was allowed to proceed for thirty minutes to provide [mPEG2-CAC-fmoc-20K-NHS]-[rIL-15] conjugates (where the informal name of the conjugate reflects the polymer reagent used to prepare the conjugate, with an understanding that for the resulting product(s), the reactive moiety in the polymer reagent has been replaced by a linkage to, in this instance, IL-15). After thirty minutes, quenching was achieved by adding 1 M glycine (pH 6.0) to the reaction mixture to achieve a final concentration of 100 mM. The pH of the quenched reaction mixture was then adjusted to 4.0 using glacial acetic acid prior to column chromatography purification and characterization.

The reaction mixture was analyzed by RP-HPLC analysis. By SDS-PAGE, the reaction mixture contained about 10-20% mono-conjugates, about 50-70% di-conjugates, and about 20-30% tri-conjugate—that is to say, the reaction mixture contained primarily di-conjugated species. The conjugate mixture was separated/isolated by anion-exchange chromatography using a Q Sepharose High Performance column and sodium phosphate buffers as the eluent phase to provide purified [mPEG2-CAC-FMOC-20kD-NHS]L-15 with an average degree of PEGylation of about 2 (with degree of PEGylation ranging from about 1.7-2.5), such that n' in the above structure for the purified composition is about 2.

For the remainder of the Examples, purified [mPEG2-CAC-FMOC-20kD-NHS]-IL-15 will be referred to as Conjugate 2.

Example 3

Preparation of a Long Acting IL-15 Receptor Agonist, [Mono-PEG2-RU-ButryALD-40K]IL15

IL-15 solution and mixed well. and set on RotoMixer for 15 min. 1/100 volume of 1 M NaCNBH3/H2O was then added to the reaction mixture. To allow for the coupling of mPEG2-ru-ButyrALD to IL-15 via a secondary amine linkage, the reaction solution was placed on a RotoMixer at 4° C. for 17 hours and was then quenched with Glycine solution. Because the PEGylation reaction was carried at acidic pH, attachment of the PEG derivative to IL-15 was more selective to the N terminal. An anion-exchange chromatography method using Q Sepharose High Performance column and sodium phosphate buffers was also developed to purify the conjugate. The purified mono-PEG2-ru-ButyrALD-40K-IL-15 conjugate was characterized by HPLC and SDS-PAGE.

For the remainder of the Examples and in the accompanying disclosure, purified [Mono-PEG2-RU-ButryALD-40K]-IL-15, i.e., having a single PEG moiety with the structure shown above covalently attached to IL-15 via an amine linkage will be referred to as Conjugate 3.

Using this same approach, conjugates are prepared using PEG2-RU-ButryALD-having different weight average molecular weights. For example, mono-PEG2-RU-ButryALD-20K]-IL-15 was prepared as described above using a 20 kD polymer reagent (referred to herein as Conjugate 4).

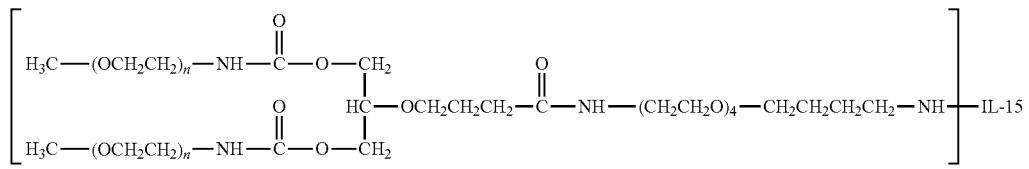

The branched mPEG-Butyraldehyde PEG reagent, Mono-PEG2-RU-ButryALD-40K,

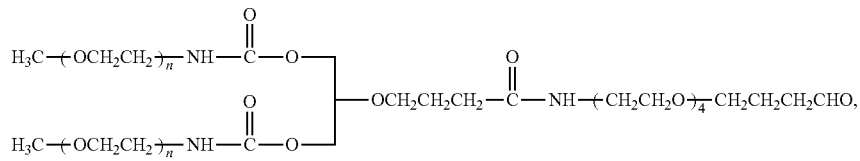

was used to prepare the subject long acting IL-15 R agonist, where the weight average molecular weight of the PEG reagent used to prepare the agonist was about 40,000 daltons.

2.7 ml of IL-15(1.23 mg/ml in PBS buffer, pH7.4) was transferred to a small reaction vial, 0.3 ml of 1M sodium acetate buffer(pH5) was added to adjust pH to pH6. mPEG2-ru-ButyrALD, 40 kDa, stored at −20° C. under nitrogen, was warmed to ambient temperature. A fifteen-fold excess (relative to the amount of IL-15) of the mPEG2-ru-ButyrALD was dissolved in MilliQ H2O to form a 10% reagent solution. The 10% reagent solution was quickly added to the Example 4

Preparation of a Long Acting IL-15 Receptor Agonist, Mono-mPEG-ButyrALD-40K-IL-15

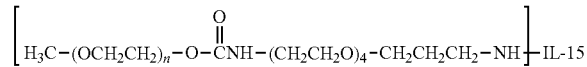

The PEG reagent, linear mPEG-Butyraldehyde, 40 kDa ("mPEG-ButyrALD"), having the structure,

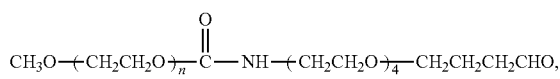

was used to prepare the subject long acting IL-15 R agonist, where the weight average molecular weight of the PEG reagent used to prepare the agonist was about 40,000 daltons.

A 2.7 ml of IL-15(1.23 mg/ml in PBS buffer, pH7.4) was transferred to a small reaction vial, 0.3 ml of 1M sodium acetate buffer (pH5) was added to adjust pH to pH6. mPEG-ButyrALD, 40 kDa, stored at −20° C. under nitrogen, was warmed to ambient temperature. A ten-fold excess (relative to the amount of IL-15) of the mPEG-ButyrALD was dissolved in MilliQ H2O to form a 10% reagent solution. The 10% reagent solution was quickly added to the IL-15 solution and mixed well. and set on RotoMixer for 15 min. 1/100 volume of 1 M NaCNBH3/H2O was then added to the reaction mixture. To allow for the coupling of mPEG-ButyrALD to IL-15 via a secondary amine linkage, the reaction solution was placed on a RotoMixer at 4° C. for 17 hours and was then quenched with Glycine solution. Because the PEGylation reaction was carried at acidic pH, attachment of the PEG derivative to IL-15 was more selective to the N terminal. An anion-exchange chromatography method using Q Sepharose High Performance column and sodium phosphate buffers was also developed to purify the conjugate. The purified mono-mPEG-ButyrALD-40K-IL-15 conjugate was characterized by HPLC and SDS-PAGE.

For the remainder of the Examples, mono-mPEG-ButryALD-40k-IL-15 will be referred to as Conjugate 5.

Example 5

Receptor Bias Evaluation of Long Acting IL-15 Receptor Agonists for IL-15Rα

The affinities of exemplary long-acting IL-15 receptor agonists (test articles) for the IL-15α receptor were measured and compared to IL-15. Affinity was measured by BIAcore using IL-15Rα:Fc captured by immobilized anti-Fc.

The test articles were diluted to 10 μM in PBS (containing 0.05% Tween 20 and 0.1 mg/ml BSA). A series of 3-fold dilutions were made and injected onto a sensor chip which was coated with IL-15Rα. The affinities were measured by determining the $k_a$ and $k_d$ rates separately, and the ratio between $k_d$ and $k_a$ was used to calculate the $K_d$ values.

Preferred conjugates, in general, are those that retain as much of the IL-15 Rα affinity as possible after PEGylation in comparison to unmodified IL-15. Stated in the contrary, preferred conjugates, in general, are those in which affinity for the IL-15 Rα is least diminished from that of unmodified IL-15.

For example, in some embodiments, a preferred conjugate exhibits no more than about a 7-fold reduction in EC50 value (ng/mL, CTLL-2 pSTAT5), and no more than about a 50% reduction in receptor alpha binding ($K_D$, pM) compared to IL-15. For example, Conjugate 1 has about a two-fold reduction in potency when compared to IL-15 and retains about 80% of alpha receptor affinity of IL-15.

TABLE 2A

| Test Article | $k_a$ (M$^{-1}$sec$^{-1}$) | $k_d$ (sec$^{-1}$) | $K_D$ (pM) |
|---|---|---|---|
| IL-15 | 5.78 × 10$^5$ | 1.49 × 10$^{-4}$ | 258 |
| Conjugate 1 | 4.92 × 10$^5$ | 1.03 × 10$^{-4}$ | 209 |

As indicated in the table above, Conjugate 1 retains its high affinity for the IL-15 a receptor (i.e., when compared to IL-15), a feature that is particularly preferred for a long-acting IL-15 receptor agonist. Affinity constants ($K_D$) (in pM) are provided for additional conjugates below.

TABLE 2B

Additional Features of Exemplary Long-acting IL-15 Receptor Agonists

| Test Article | EC50 (ng/mL) CTLL-2 pSTAT5 | IL-15Rα $K_D$ (pM) | PK (MRT), h |
|---|---|---|---|
| IL-15 | 0.27 | 258 | |
| Conjugate 1 | 0.62 | 201/209 | 21 |
| Conjugate 3 | 16.80 | 411 | 30 |
| Conjugate 4 | 6.21 | 215 | |
| Conjugate 5 | 1.45 | 144 | 25 |

Example 6

In Vivo Study: Single Dose PK Study in Mice

C57BL/6 mice (n=3/group) were administered a single intravenous dose of IL-15 (control) at 0.3 mg/kg or of Conjugate 2 at a dose of 0.3 mg/kg. Following administration, blood samples were collected at various time points post administration (24 hours, 48 hours, 78 hours, 96 hours). Samples were pooled and assessed for pharmacodynamic analysis of drug action on lymphocyte cell populations by flow cytometry, expressed as a fold change relative to vehicle control (results described in later examples below). In addition to changes in cell number, functional markers and markers of activity were quantified. Finally, at each time point, plasma concentration of drug was determined. See FIG. 6.

Figure 6:
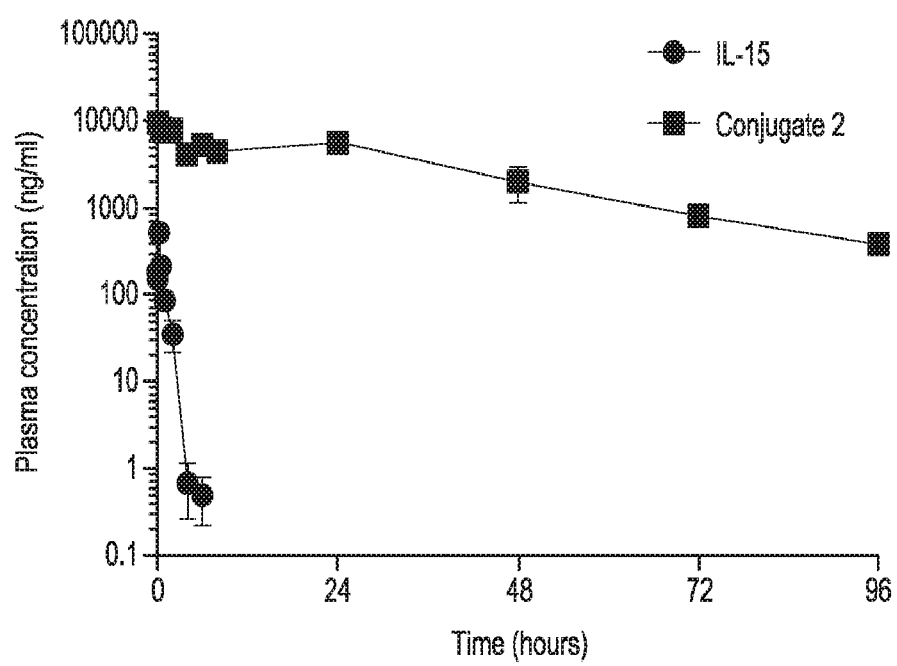
FIG. 6. is a plot of plasma concentration of test article (IL-15, solid circle, or mPEG2-CAC-FM0C-20K-NHS-IL-15, also referred to as N-(2-methoxyPEG-ethyl)-7-(4-((2-methoxyPEG-ethyl)amino)-4-oxobutyl)-9-ethyl-9 H-fluorene-4-carboxamide carbamate-IL-15, or Conjugate 2, solid square) over time following administration of a single intravenous dose of test article in mice as described in Example 6.

As shown in FIG. 6, Conjugate 2 maintained measurable concentrations in plasma over an extended period of time, e.g., for greater than 1 week (solid squares), with a $T_{1/2}$ of from about 20-30 hours, in contrast to the rapid drop in plasma levels observed for non-long acting IL-15 (solid circles) following administration.

Example 7

In Vivo Study: Single Dose PK Study in Rats

Rats (n=3/group) were administered a single intravenous dose of Conjugate 2 at dosages of 0.3, 0.15 and 0.075 mg/kg, or a single subcutaneous dose of Conjugate 2 at 0.15 mg/kg. Following administration, blood was collected at days 1-7 post administration (with multiple samples collected over the first 24 hours following administration). At each time point, plasma concentration of drug was determined. See FIG. 7.

Figure 7:
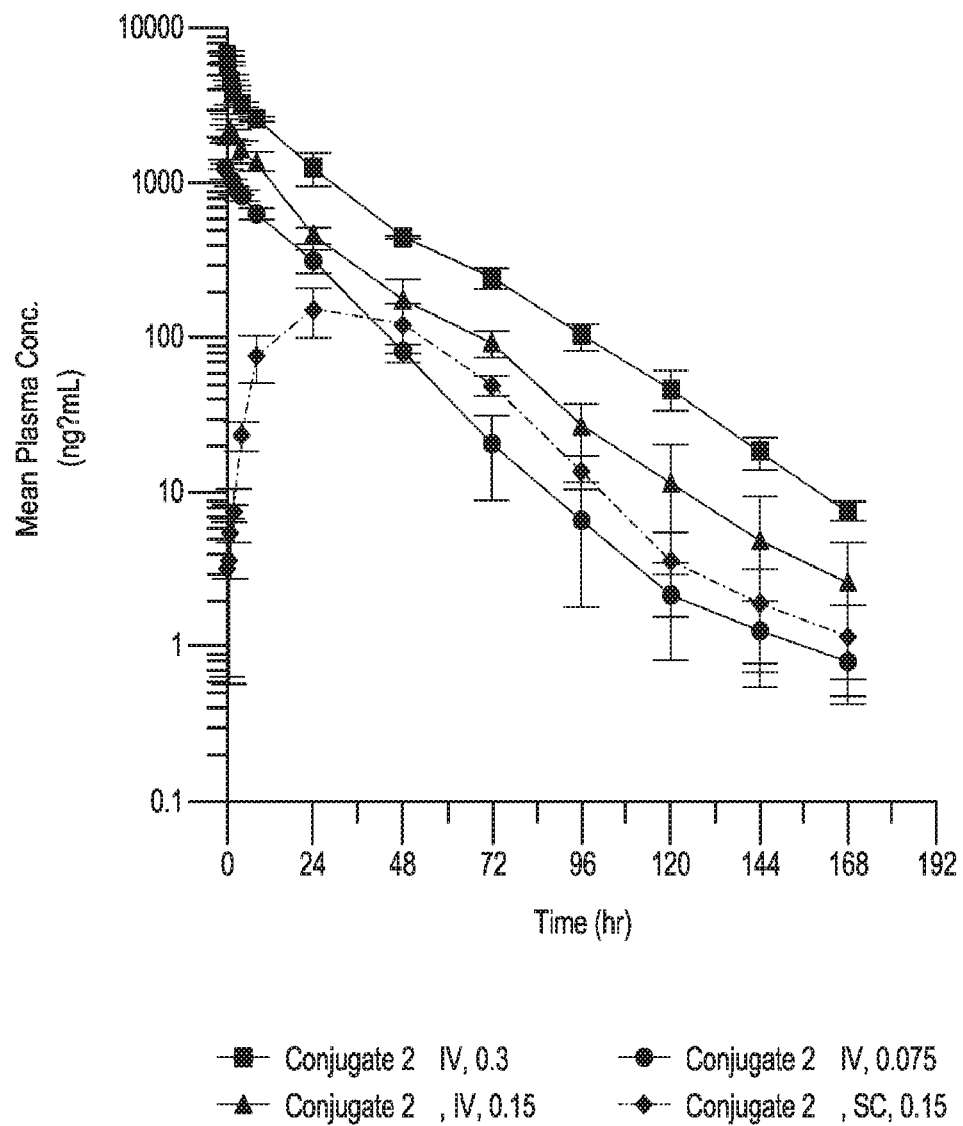
FIG. 7 is a plot of mean plasma concentration of mPEG2-CAC-FMOC-20K-NHS-IL-15, also referred to as N-(2-methoxyPEG-ethyl)-7-(4-((2-methoxyPEG-ethyl)amino)-4-oxobutyl)-9-ethyl-9 H-fluorene-4-carboxamide carbamate-IL-15, or Conjugate 2, over time following administration of a single intravenous dose of Conjugate 2 in rats at dosage amounts of 0.3 (■), 0.15 (▲) and 0.075 mg/kg (●), or a single subcutaneous dose of Conjugate 2 at 0.15 mg/kg (♦) as described in Example 7.

As shown in FIG. 7, and similar to the results shown in FIG. 6 for mice, administration of Conjugate 2 resulted in sustained and dose-proportional exposure to drug.

Example 8

In Vivo IL-15 Signaling Study in Mice

Figure 8A:
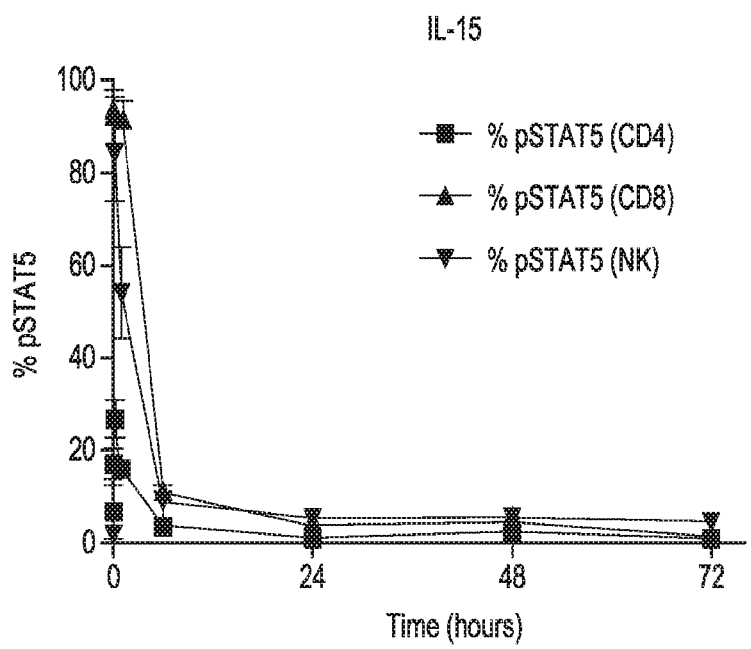
FIGS. 8A and 8B illustrate the degree of STAT5 phosphorylation in various lymphocytes, i.e., CD4 (■), CD8 (▲), and NK cells (▼) following administration of a single i.v. dose of either IL-15 (FIG. 8A) or Conjugate 2 (0.3 mg/kg, FIG. 8B) as described in Example 8.
Figure 8B:
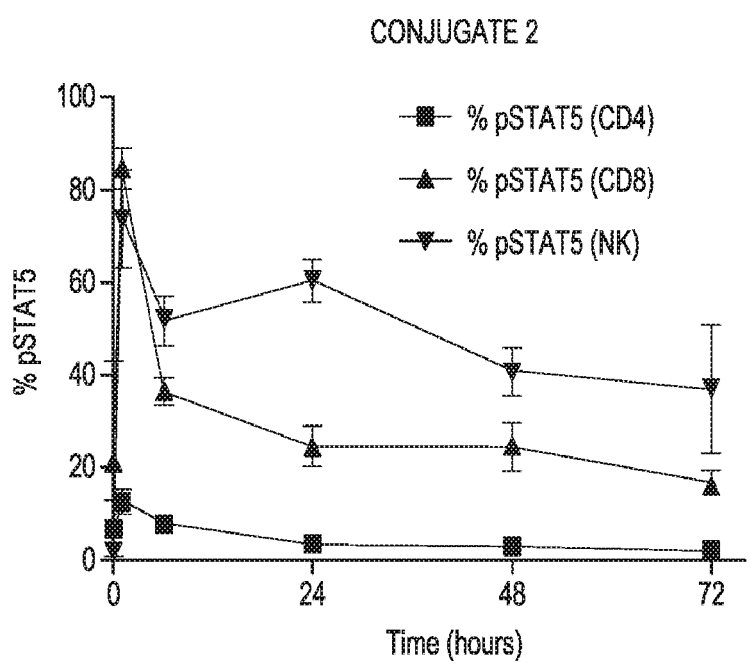

Mice were dosed as described in Example 6 above to assess in-vivo signaling as assessed by degree of STAT5 phosphorylation. Degree of STAT5 phosphorylation in various lymphocytes (CD4, CD8, and NK cells) was assessed by staining whole blood for leukocyte surface markers and pSTAT5, followed by measurement by flow cytometry. Results are shown in FIGS. 8A and 8B for IL-15 and for Conjugate 2, respectively.

STAT5 phosphorylation is an early and transient event in IL-15/IL-2 receptor signaling. As seen in FIG. 8A, while in-vivo signaling activity is extremely short-lived for IL-15, exemplary Conjugate 2 induces lasting STAT5 phosphorylation, most notably in NK cells (upside down solid triangles ▼) and in CD8 cells (normal solid triangles ▲) as well, with measurable STAT5 phosphorylation activity noted in NK and CD8 cells beyond 72 hours. STAT5 phosphorylation activity for CD4 cells is also shown (closed squares ■).

Example 9

In Vivo IL-15 Signaling Study in Non-Human Primates

In the study, cynomolgus monkeys (cyno), one female and one male, were each intravenously administered a single dose of Conjugate 2 (0.5 mg/kg). A series of blood samples were taken from each animal both prior to treatment (day −6 and −1) and at multiple intervals following treatment for assessment by flow cytometry of STAT5 phosphorylation in various types of lymphocytes (CD4, CD8, and NK cells). Results are provided in FIGS. 9A (CD4), 9B (CD8), and 9C (NK).

Figure 9A:
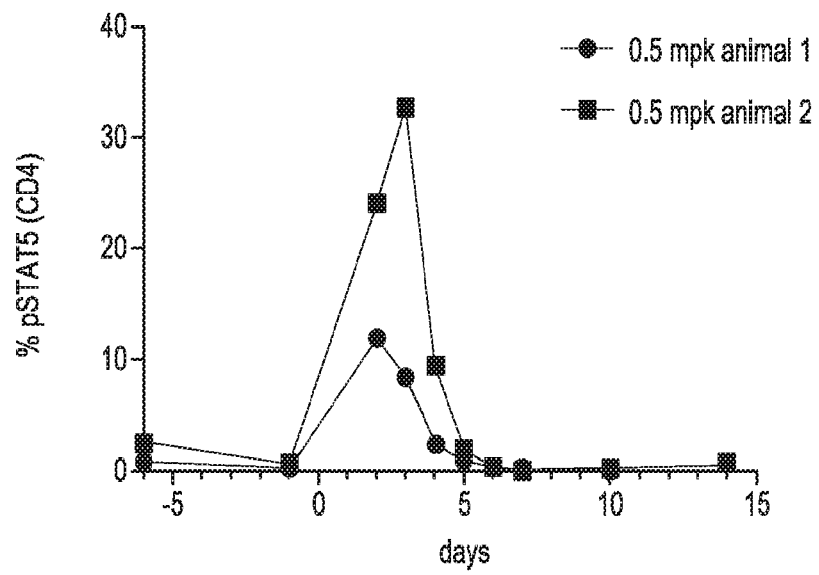
FIGS. 9A, 9B and 9C are plots demonstrating the degree of STAT5 phosphorylation in various lymphocytes, i.e., CD4, CD8, and NK cells, respectively, following administration of a single i.v. dose of Conjugate 2 (0.5 mg/kg) in cynomolgus monkeys, as described in Example 9.
Figure 9B:
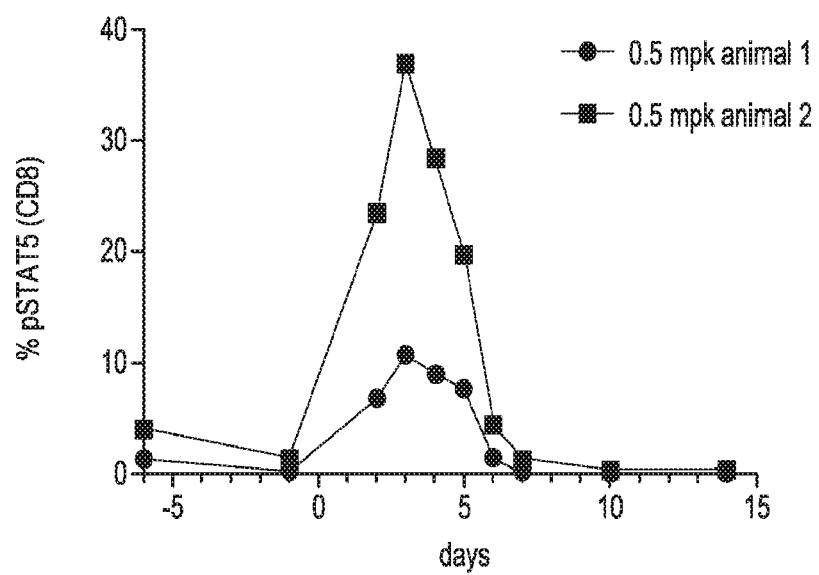
Figure 9C:
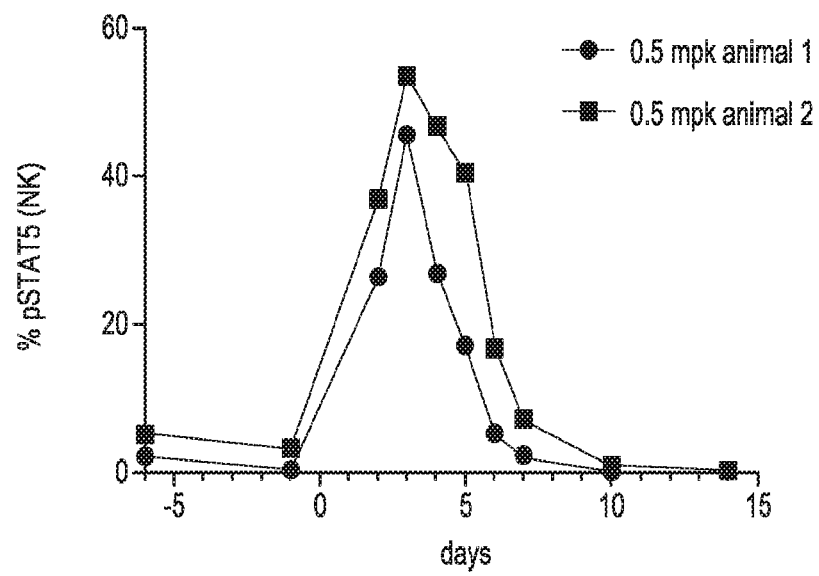

As shown in FIGS. 9A-9C, the results are similar to those observed in mice (Example 7), although in non-human primates, STAT5 phosphorylation was observed in CD4 cells as well (FIG. 9A). STAT5 phosphorylation in each of the three cell types rose substantially following administration, reaching a maximum level between about 3 and 4 days following administration of the illustrating long-acting IL-15 agonist and returning to near d-1 levels (i.e., pre-dose) by about days 5-10. Similar to Example 7, these results indicate a sustained presence of active IL-15 species.

Example 10

In Vitro IL-15 Activity of Exemplary Long Acting IL-15 Receptor Agonists in NK Subsets of Human Peripheral Blood Mononuclear Cells (PBMCS)

Assessment of in-vitro activity of exemplary long-acting IL-15 receptor agonists (e.g., Conjugates 1, 3 and 5) was carried out by investigating signaling in NK cell subsets of human PBMCs as shown in FIGS. 10A (CD56bright cells) and 10B (CD56dim cells). STAT5 phosphorylation was evaluated as previously described for assessing IL-15 signaling activity of the long acting IL-15 receptor agonists.

TABLE 3

| Compound | EC50 (ng/ml) pSTAT5 CD56bright NK |
|---|---|
| IL-15 | 0.4 |
| Conjugate 1 | 2.4 |
| Conjugate 3 | 69.76 |
| Conjugate 5 | 32.26 |

Results are shown in FIGS. 10A (CD56bright) and 10B (CD56dim).

As can be seen, each of the illustrative conjugates induces IL-15 signaling in huPBMCs, while Conjugate 1 potently induces such signaling. Of conjugates tested (not all data shown), Conjugate 1 demonstrated the highest potency/activity on huPBMCs. The data illustrates that even when maintaining the same degree of PEGylation (i.e., the number of PEG moieties) and the same size of PEG moieties per IL-15 protein, different PEG architectures and linkers can elicit very different effects on bioactivity in the resulting conjugates.

A second study was conducted to investigate/compare the pStat5 response of human PBMCs obtained from two donors (CD3, CD4, CD8, CD56 (bright and dim) and CD4-Tregs (CD25+Foxp3+)) to IL-15, Conjugate 1 and Conjugate 5. An 11-point dose response was examined using a 10-fold dilution with a dose range of 0.001-10000 ng/ml and a 20 min stimulation. Each of the test articles was diluted in IL-15 buffer +0.1% BSA. Results are provided in the tables which follow.

TABLE 4

| % pSTAT5 and pSTAT5 MFI in CD3 and CD4 cells | | | | | | | |
|---|---|---|---|---|---|---|---|
| EC50 (ng/ml)-% pSTAT5 | | | | EC50 (ng/ml)-MFI | | | |
| CD3 | | CD4 | | CD3 | | CD4 | |
| Compound | donor1 | donor2 | donor1 | donor2 | donor1 | donor2 | donor1 | donor2 |
| IL-15 | 0.17 | 0.17 | 0.177 | 0.20 | 4.0 | 5.22 | 3.6 | 5.8 |
| Conjugate 1 | 0.75 | 1.1 | 0.75 | 0.83 | 22.1 | 108.8 | 23.54 | 106.5 |
| Conjugate 5 | 1.3 | 1.7 | 1.3 | 1.14 | 84.73 | 154.2 | 84.21 | 98.18 |

Based on the data in Table 3 above, IL-15 appears to be about 4-6-fold more potent than Conjugate 1 for both CD3 and CD4 induction; the potencies of Conjugate 1 and Conjugate 5 appear to be similar for CD3 and CD4 induction.

TABLE 5

% pSTAT5 and pSTAT5 MFI in CD4-Treg and CD8 cells

| | EC50 (ng/ml)-% pSTAT5 | | | | EC50 (ng/ml)-MFI | | | |
|---|---|---|---|---|---|---|---|---|
| | Treg | | CD8 | | Treg | | CD8 | |
| Compound | donor1 | donor2 | donor1 | donor2 | donor1 | donor2 | donor1 | donor2 |
| IL-15 | 0.08 | 0.084 | 0.17 | 0.15 | 0.6 | 0.71 | 3.5 | 5.5 |
| Conjugate 1 | 0.23 | 0.37 | 0.76 | 1.54 | 2.5 | 2.9 | 16.73 | 99.76 |
| Conjugate 5 | 0.44 | 0.45 | 1.4 | 2.5 | 3.5 | 5.4 | 53.7 | 204.6 |

Based upon the data in Table 5 above, it appears that IL-15 is approximately 3-5 fold more potent than Conjugate 1 for Treg and CD8 induction; the potencies of Conjugates 1 and 5 appear to be substantially similar for CD4 and CD8 induction.

TABLE 6

% pSTAT5 and pSTAT5 MFI in CD56bright and CD56dim cells

| | EC50 (ng/ml)-% pSTAT5 | | | | EC50 (ng/ml)-MFI | | | |
|---|---|---|---|---|---|---|---|---|
| | CD56bright | | CD56dim | | CD56bright | | CD56dim | |
| Compound | donor1 | donor2 | donor1 | donor2 | donor1 | donor2 | donor1 | donor2 |
| IL-15 | 0.11 | 0.19 | 0.26 | 0.54 | 0.49 | 0.96 | 1.4 | 3.7 |
| Conjugate 1 | 1.4 | 1.9 | 2.9 | 5.9 | 7.8 | 12.4 | 23.25 | 73.05 |
| Conjugate 5 | 5.1 | 4.5 | 16.48 | 27.12 | 24.86 | 56.9 | 97.51 | 283.4 |

Based upon the data in Table 6, it appears that IL-15 is ~10-fold more potent than Conjugate 1 for CD56 induction. However, Conjugate 1 appears to be more potent than Conjugate 5 in inducing CD56 bright and CD56dim.

Based upon the preceding data, IL-15, Conjugate 1 and Conjugate 5 showed similar pSTAT5 induction for all the cell populations, the maximum response appears to be higher for CD56bright and Treg cells.

TABLE 7

Summary Table

| | EC50 (ng/ml)-% pSTAT5 | | | | | |
|---|---|---|---|---|---|---|
| Compound | CD3 | CD4 | Treg | CD8 | CD56bright | CD56dim |
| IL-15 | 0.17 | 0.177 | 0.08 | 0.17 | 0.11 | 0.26 |
| Conjugate 1 | 0.75 | 0.75 | 0.23 | 0.76 | 1.4 | 2.9 |
| Conjugate 5 | 1.3 | 1.3 | 0.44 | 1.4 | 5.1 | 16.48 |

Based upon the foregoing data, IL-15 is approximately 3-4 fold more potent than Conjugate 1 and is approximately 5-8 fold more potent than Conjugate 5 in inducing CD3, CD4, CD8 and Treg cells, while IL-15 is approximately 12-fold more potent than Conjugate 1 and is approximately 40-60 fold more potent than Conjugate 5 in inducing CD56bright and CD56dim cells—pointing to certain unforeseen and particularly advantageous features of Conjugate 1.

Example 11

In-Vivo Study: Single-Dose PD Study in Mice—Cell Proliferation and Activation

Balb/c mice (n=3/group) were administered a single intravenous dose of vehicle (50 mM sodium phosphate, 100 mM sodium chloride, 10% sucrose, pH7.4) or of Conjugate 1 at doses of 0.03 mg/kg (FIG. 11, low dose), 0.3 mg/kg (FIG. 11, medium dose) or 1 mg/kg (FIG. 11, high dose). Following administration, blood samples were collected at various time points post-administration (24 hours, 48 hours, 78 hours, 96 hours, 120 hours). Samples from each mouse were subject to pharmacodynamic analysis of drug action on lymphocyte cell populations by flow cytometry. In addition to changes in cell number, functional markers and markers of activity were examined.

Additional administrations of Conjugate 1 were performed at doses of 0.01 mg/kg, 0.1 mg/kg, and 1.5 mg/kg.

Figure 11B:
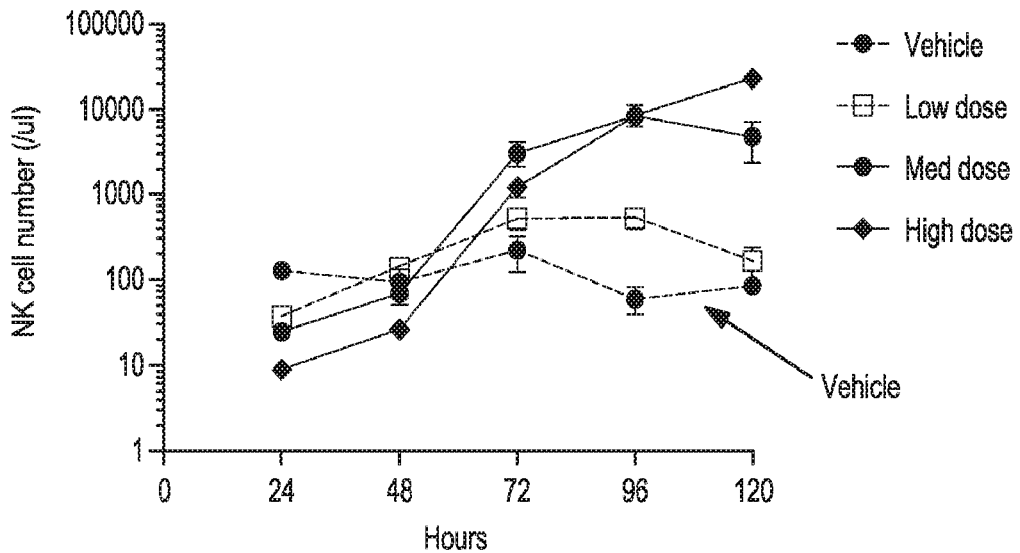

Results illustrating proliferation of NK cells in mice administered each of 0.03 mg/kg (FIG. 11, low dose), 0.3 mg/kg (FIG. 11, medium dose), and 1 mg/kg (FIG. 11, high dose) of Conjugate 1 are provided in FIGS. 11A and 11B.

NK cells and their proliferation were defined using CD45+CD3−CD49b+ and CD45+CD3−CD49b+Ki67+ marker combinations. Following dosing, blood samples were acquired on the Fortessa flow cytometer running FACS DIVA software. Flowjo software was used for analysis and NK cell absolute values and Ki67% positivity within NK cells were plotted using Prism.

FIG. 11A is a plot of Ki67 expression (as a percentage) over time; FIG. 11B provides NK cells numbers over time. The plots illustrate the ability of Conjugate 1 to induce sustained NK cell proliferation in mice.

The effect of exemplary long acting IL-15 receptor agonists was explored on NK cells of all maturation levels. The peripheral NK cell pool can be delineated by expression of CD27, with $CD27^{lo/-}$ NK cells being more cytotoxic and producing more cytokines than $CD27^{high}$ NK cells (Hayakawa Y, et al., *J Immunol.* 2006; 176:1517-1524). Mature peripheral NK cell populations have been further refined into four stages of maturation, defined by sequential upregulation of CD11b expression followed by downregulation of CD27, with the most immature NK cells being $CD27^-$ $CD11b^-$ and the most mature NK cells being $CD27^-CD11b^+$ (Chiossone L., et al., *Blood,* 2009; 113:5488-5496).

In mouse, four different maturation states of NK cells are defined by CD27 and CD11b expression. Once NK marker (CD49b+), natural activating NK receptor (NKp46+) and IL-15/IL-2RB (CD122+) triple positive cells were identified, immature (CD11b−CD27−), early (CD11b−CD27+), high effector (CD11b+CD27+) and terminal effector (CD11b+CD27−)NK cells were quantified by flow cytometry.

NK cells in various maturation states were quantified in mice receiving a single dose, or after the third dose of a q7dx3 schedule, of Conjugate 1 at 0.01, 0.03, 0.1, 0.3, 1.0, and 1.5 mg/kg as described above. Using flow cytometry, the NK population of interest was identified by CD49b, NKp46 and CD122 positivity. CD11b and CD27 were then used to further differentiate the NK population in immature (CD11b−CD27−), early NK (CD11b−CD27+), high effector (CD11b+CD27+) and terminal effector (CD11b+CD27−) subpopulations. Peripheral blood was run on the Fortessa flow cytometer and absolute values for each population were determined using counting beads during sample acquisition using BD FACS DIVA software. Flow cytometric analysis was conducted using Flowjo software and data plotted in Prism.

Results are shown in FIGS. 12A-D. Additional results are shown in FIGS. 22A-D. The q7dx3 results are shown in FIGS. 28A-D. As can be seen from the plots, Conjugate 1 was effective to increase numbers of NK cells of all maturation levels (terminal effector cells, pre-NK cells, high effector cells and early NK cells). A dose-dependent increase of NK cells in all maturation sub-populations was observed, an effect that lasted for at least 120 hours.

Figure 13A:
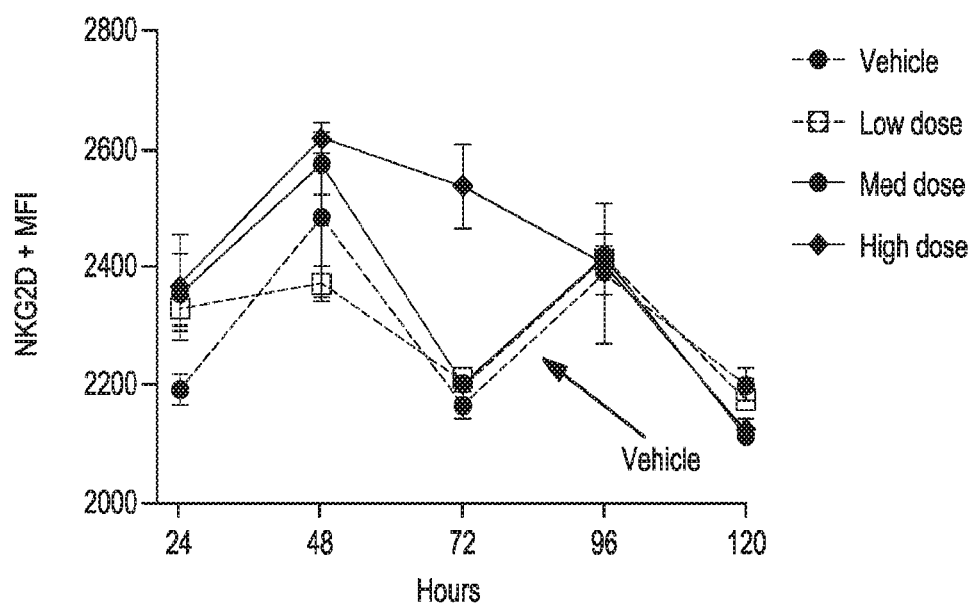
FIGS. 13A and 13B are plots illustrating levels of expression of NKG2D (FIG. 13A) and Granzyme B (FIG. 13B) by NK cells in mice following i.v. administration of Conjugate 1 at doses of 0.03 mg/kg (low dose, open squares), 0.3 mg/kg (medium dose, solid circles, solid line), or 1 mg/kg (high dose, diamonds) compared to vehicle (solid circles, dashed line) as described in Example 11.
Figure 13B:
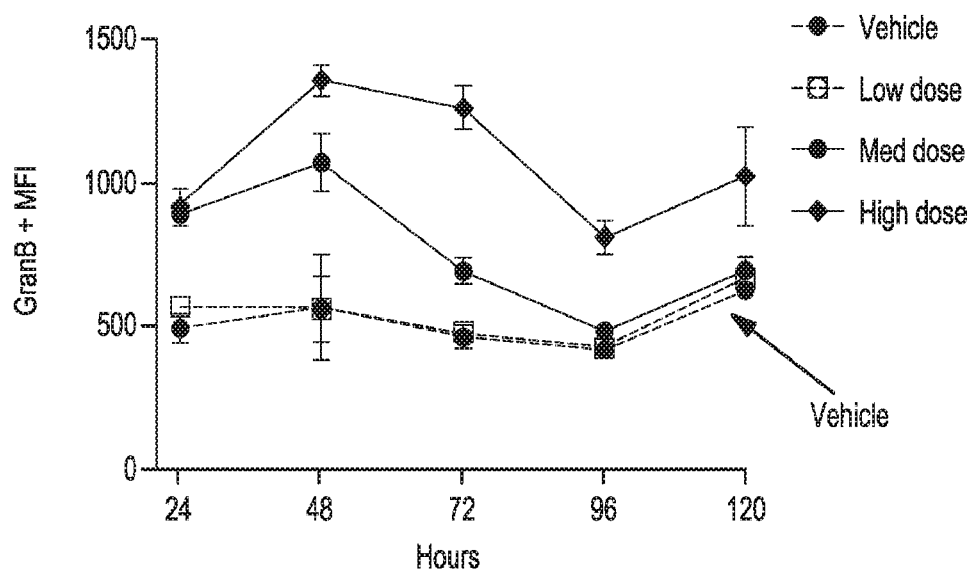

The surface expression of NKG2D was conducted using flow cytometric analysis of anti-NKG2D signal, expressed as mean fluorescence intensity (MFI) in NK cells. Similarly, the level of intracellular granzyme B was conducted using flow cytometry-based detection of anti-Granzyme B signal, also expressed as MFI in NK cells. Following detection of NKG2D and granzyme B signal using the Fortessa flow cytometer and FACS Diva software, analysis was conducted using Flowjo software. MFI values were plotted using Prism. Results are shown in FIGS. 13A and 13B, which further illustrate the ability of Conjugate 1 to increase NK cell activation as evidenced by its ability to effect a sustained increase in both NKG2D and Granzyme B (a pro-apoptotic serine protease) expression by NK cells in comparison to vehicle, most notably for the medium and high dosage amounts. Dose-dependent increases in both NK activation markers was observed following a single dose of Conjugate 1.

Figure 14:
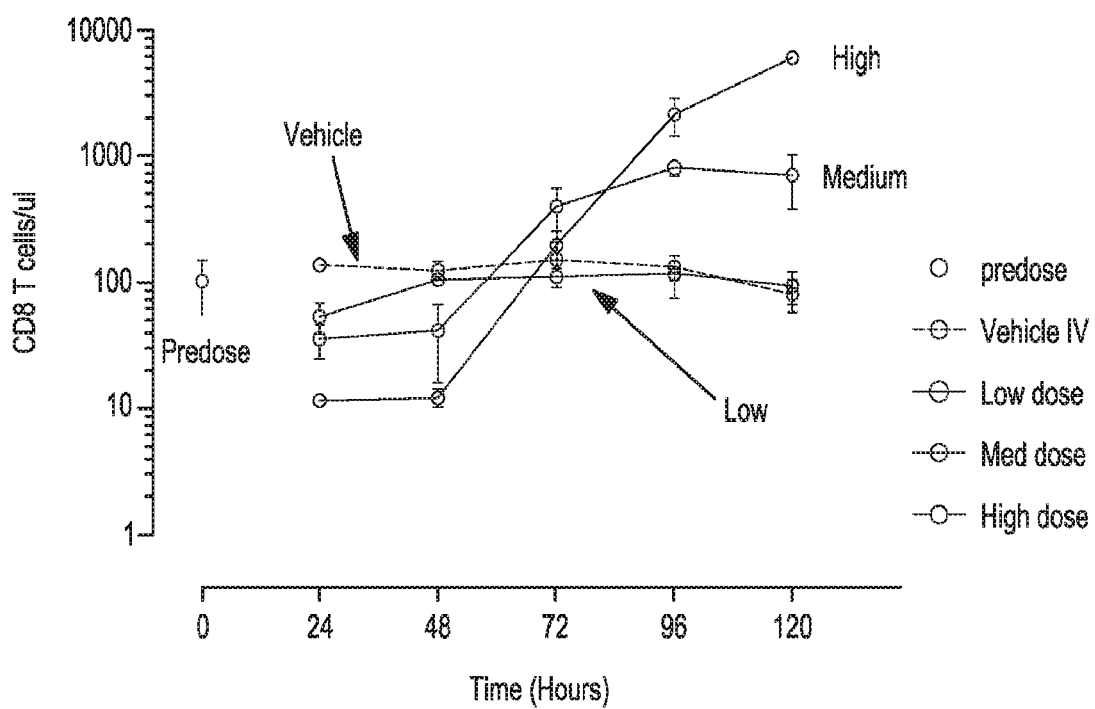
FIG. 14 is a plot illustrating numbers of CD8 T cells, expressed in cells/µl, both pre-dose and from 24 hours to 120 hours post administration following i.v. administration of Conjugate 1 in mice at doses of 0.03 mg/kg (low dose), 0.3 mg/kg (medium dose), or 1 mg/kg (high dose) as described in Example 11.
Figure 24:
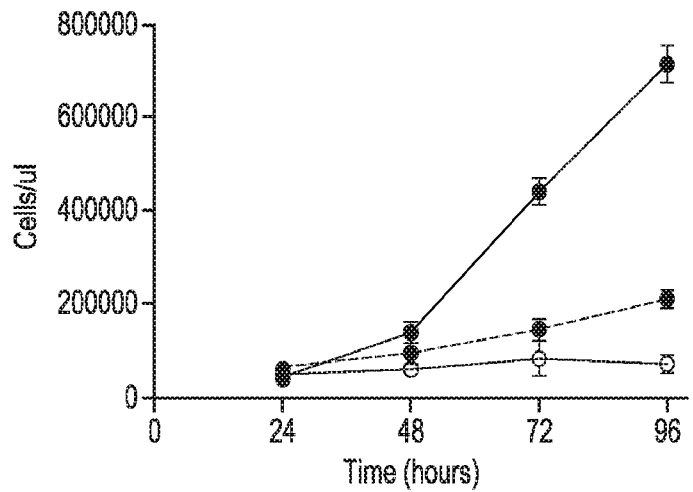
FIG. 24 is a plot illustrating numbers of CD8 T cells isolated from mouse spleen, expressed in cells/µl, both pre-dose and from 24 hours to 96 hours post administration following i.v. administration of Conjugate 1 in mice at doses of 0.03 mg/kg (filled circles, dashed line) and 0.3 mg/kg (filled circles, solid line), with vehicle IL-15 buffer (open circles, dashed line) as described in Example 11.

In mouse, CD8 T cells were defined as CD45+CD3+ CD4−CD8+. Blood and spleen from mice were subject to immunophenotyping using the Fortessa flow cytometer and with analysis using Flowjo software. Absolute CD8 cell counts were plotted in Prism as shown in FIG. 14 (blood) and FIG. 24 (spleen). FIG. 14 and FIG. 24 illustrate the ability of Conjugate 1 to induce proliferation and a sustained increase in numbers of CD8 T-cells following a single i.v. administration in mice at each of the dosage amounts described above. The impact is most notable for the medium (0.1 mg/kg, 0.3 mg/kg) and high (1.0 mg/kg, 1.5 mg/kg) dosage amounts.

Figure 15A:
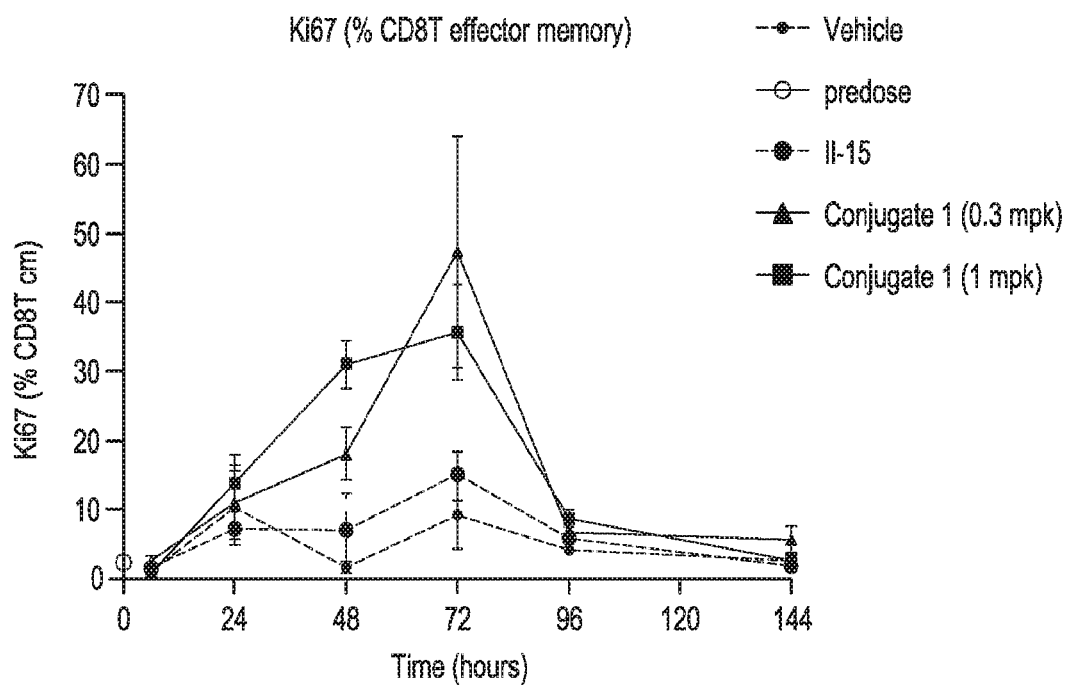
FIGS. 15A and 15B are plots illustrating illustrates levels of Ki67 expression (expressed as a percentage) over time for T effector memory cells and T central memory cells, respectively, versus time post administration following i.v. administration of Conjugate 1 in mice at doses of 0.3 mg/kg or 1.0 mg/kg in comparison to vehicle and IL-15 as described in Example 11.
Figure 15B:
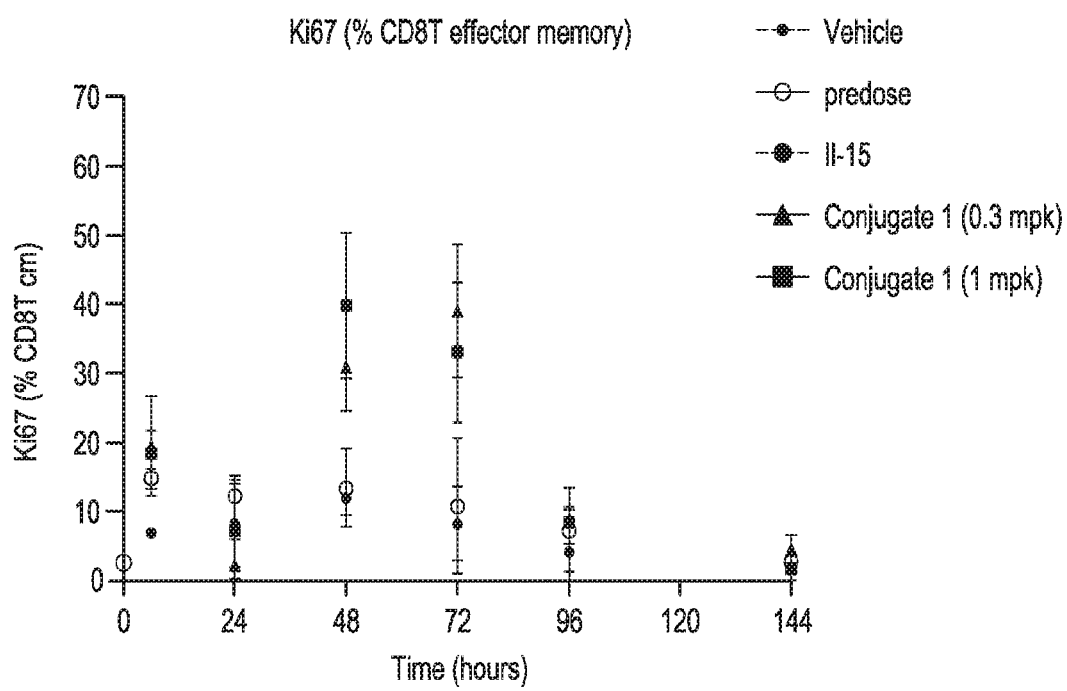
Figure 25:
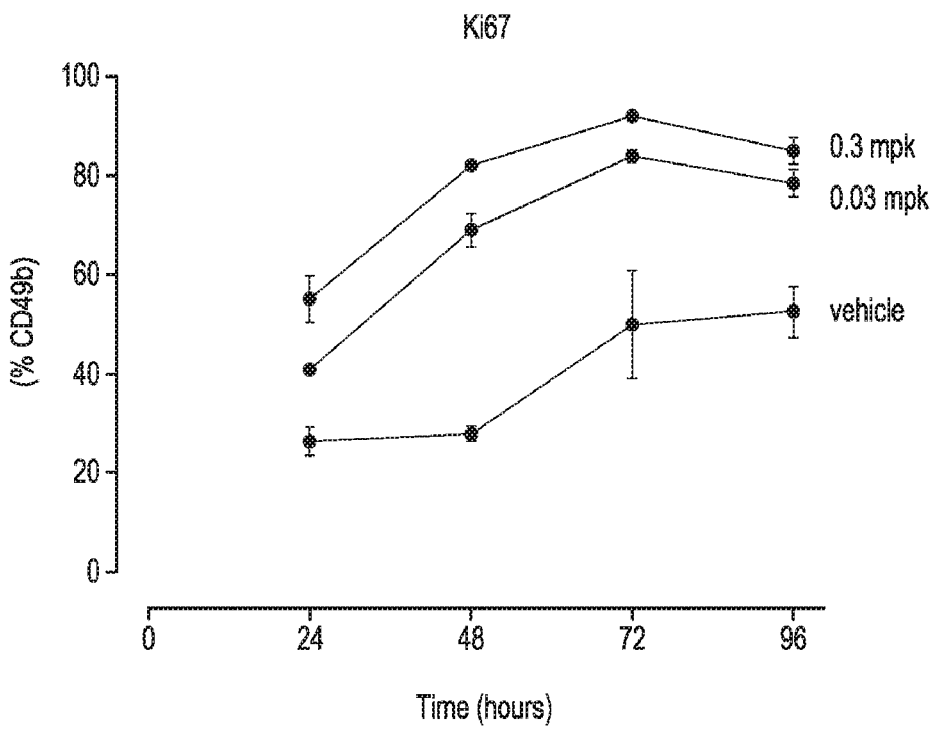
FIG. 25 is a plot illustrating levels of Ki67 expression (expressed as a percentage) for CD49b cells versus time post administration following i.v. administration of Conjugate 1 in mice at doses of 0.03 mg/kg or 0.3 mg/kg in comparison to vehicle IL-15 buffer, as described in Example 11.
Figure 26:
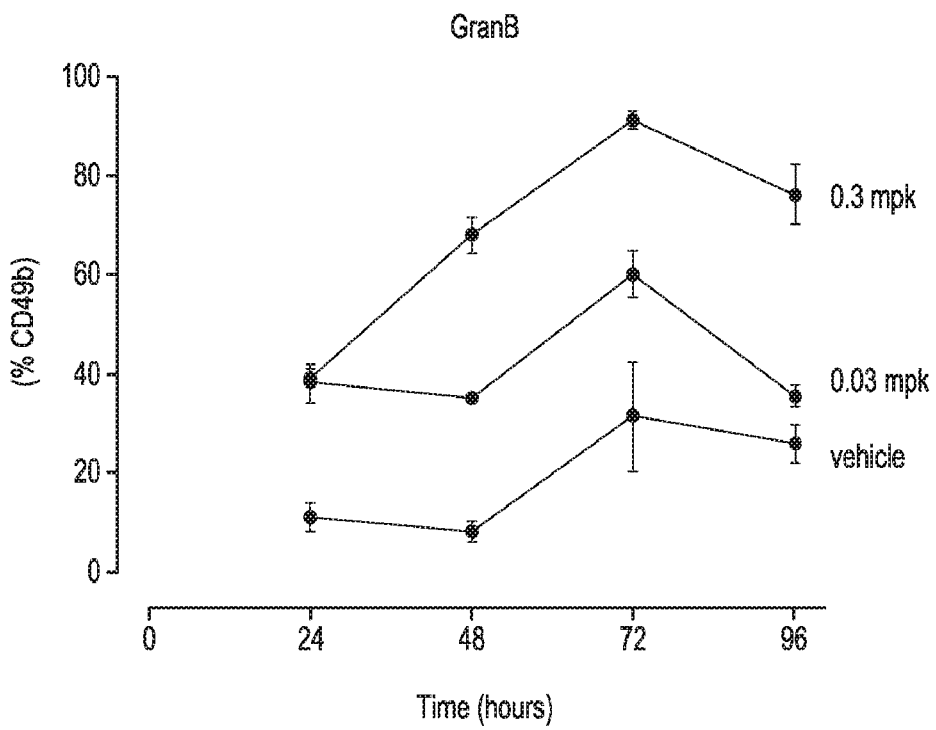
FIG. 26 is a plot illustrating levels of Granzyme B expression (expressed as a percentage) over time for CD49b cells versus time post administration following i.v. administration of Conjugate 1 in mice at doses of 0.03 mg/kg or 0.3 mg/kg in comparison to vehicle IL-15 buffer, as described in Example 11.

In mouse, CD8 effector memory (Tem) and CD8 central memory (Tcm) T cells were identified as CD45+CD3+CD4− CD8+CD44+CD62− and CD45+CD3+CD4−CD8+CD44+ CD62L+. Proliferation of these memory populations was conducted using Ki-67 positivity. Following a single dose of Conjugate 1 or IL-15, blood and spleen were subject to immunophenotyping using the Fortessa flow cytometer, DIVA acquisition software and Flowjo analysis software. Graphs were plotted in Prism. Conjugate 1 induces a dose-dependent increase in both effector and central memory CD8 T cells whereas single dose IL-15 does not, as shown in FIGS. 15A and 15B for blood. Conjugate 1 induces a dose-dependent increase in both Ki67 and Granzyme B, whereas single dose IL-15 does not, as shown in FIGS. 25 and 26 for spleen. Both effector and central memory populations proliferate in response to administration of Conjugate 1, an exemplary long acting IL-15 agonist.

Example 12

In-Vivo Study: Single-Dose PD Study in Non-Human Primates

In the study, cynomolgus monkeys, one female and one male, were administered 500 μg/kg of Conjugate 2 intravenously. A series of blood samples were taken from each animal before treatment (day −6 and −1) and at multiple intervals following single dose treatment for assessment by flow cytometry of lymphocyte cell numbers (NK cells, CD8 T-cells, etc.) and activation.

Figure 16A:
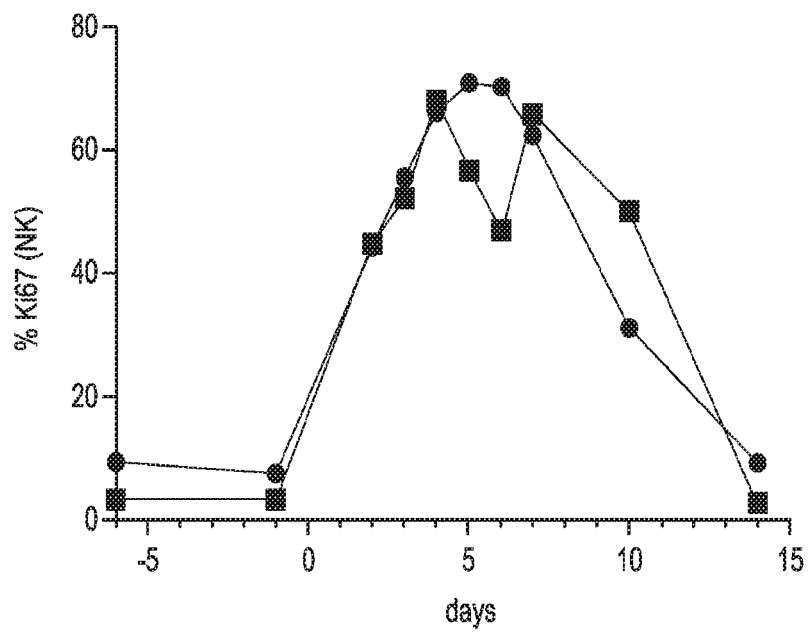
FIGS. 16A and 16B are plots illustrating NK cell proliferation in cynomolgus monkeys following i.v. administration of Conjugate 2 at a dose of 500 µg/kg as described in Example 12.
Figure 16B:
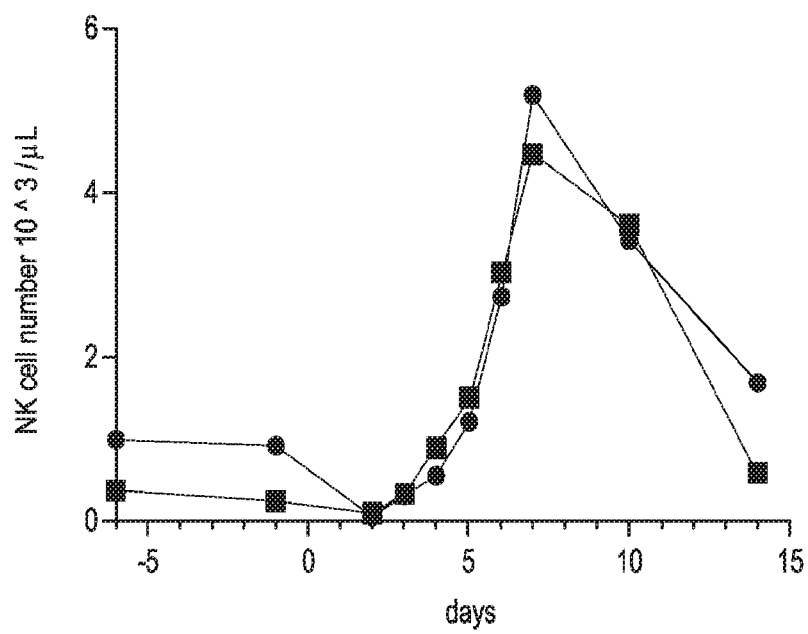

NK cell counts were determined to assess the ability of exemplary Conjugate 2 to induce sustained NK cell proliferation in non-human primates; results are shown in FIGS. 16A and 16B. NK cells and their proliferation in blood from cynomolgus monkey were identified by flow cytometry. Acquisition and analysis of NK cells (CD45+CD3−CD16+) and their proliferation status (CD45+CD3−CD16+Ki67+) were conducted using BD FACS DIVA software. Absolute values for NK cells and proliferating NK cells were used to calculate % Ki67 positivity within the NK population. Pre and post-treatment values were plotted using Prism.

As shown therein, single dose administration of Conjugate 2 was effective to induce sustained NK cell proliferation in non-human primates.

Figure 17:
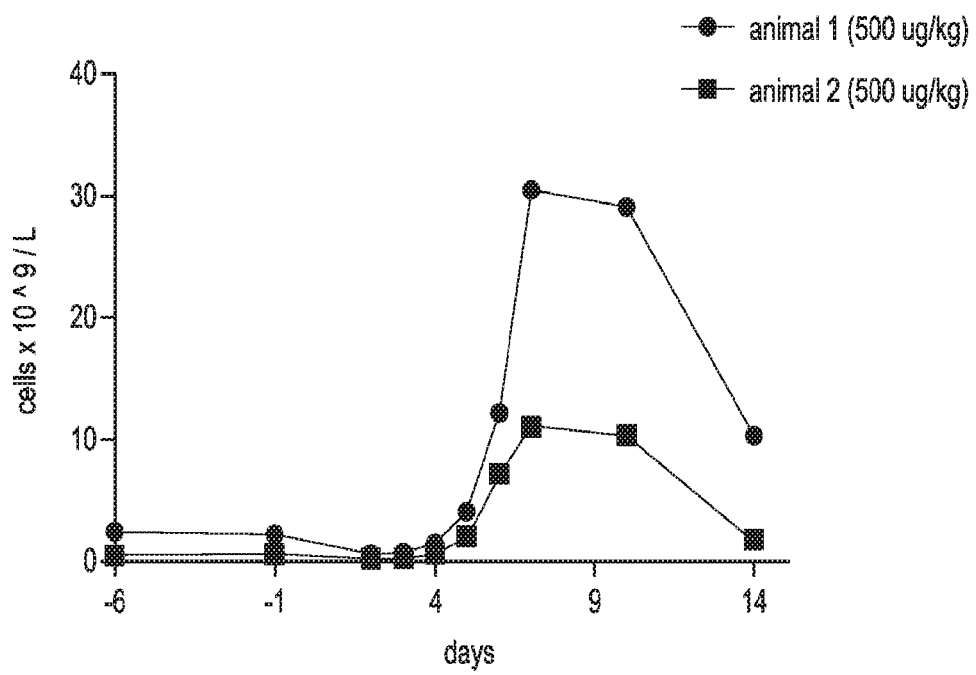
FIG. 17 is a plot illustrating CD8 T-cell counts in cynomolgus monkeys (shown for each animal) following i.v. administration of Conjugate 2 at a dose of 500 µg/kg as described in Example 12 from pre-dose to 14 days post-administration.

CD8 T cell counts were also determined as illustrated in FIG. 17 for each animal from pre-dose to 14 days post-administration. Specifically, CD8 T cells were defined as CD45+CD3+CD4−CD8+. Blood from the monkeys was also subject to immunophenotyping as previously described. In monkey, CD8 T cells increased in a sustained manner, an effect lasting for at least 10 days. This plot further exemplifies the ability of an exemplary long acting IL-15 receptor agonist, Conjugate 2, to induce proliferation and sustained increases in numbers of CD8 T-cells post-administration.

Figure 18A:
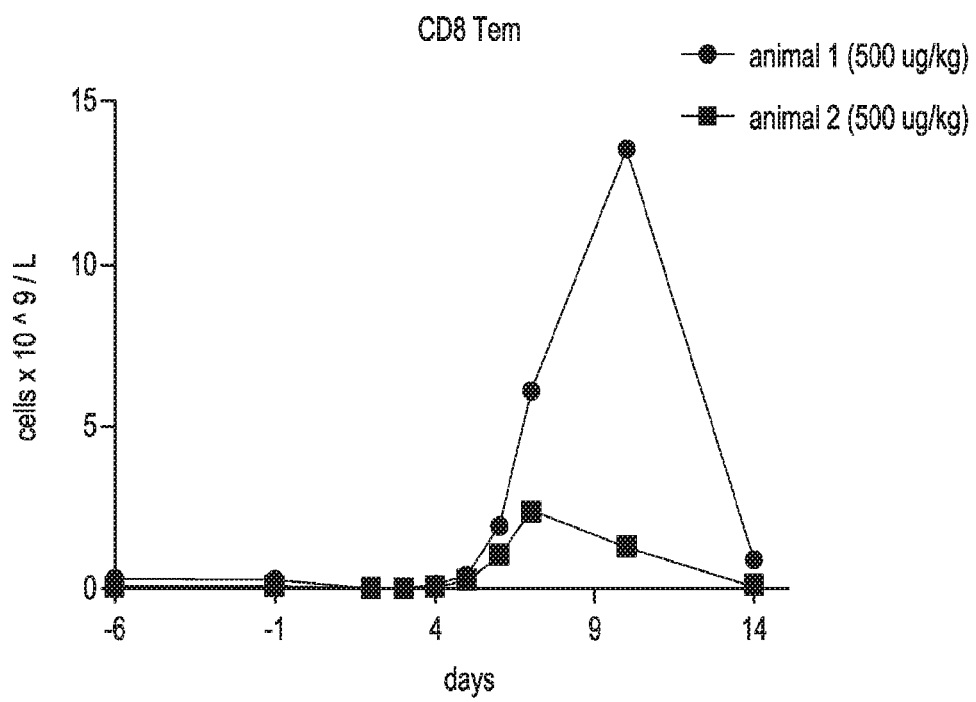
FIGS. 18A and 18B are plots illustrating numbers of CD8 T effector memory cells (TEM cells) and CD8 T central memory cells ($T_{CM}$), respectively, in cynomolgus monkeys versus time post administration (from pre-dose to 14 days post-administration) following i.v. administration of Conjugate 2 at a dose of 500 µg/kg as described in Example 12.
Figure 18B:
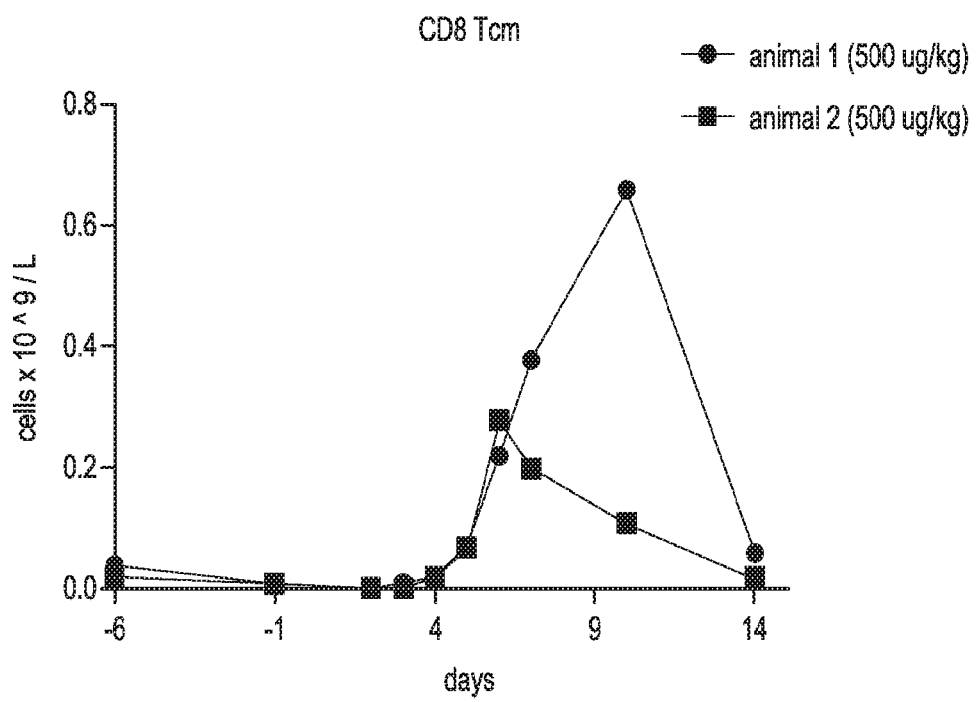

In monkey, CD8 TEM cells were defined as CD45+CD3+ CD4−CD8+CD45Ra−CD197− and CD8 $T_{CM}$ were defined as CD45+CD3+CD4−CD8+CD45Ra−CD197+. Immunophenotyping was conducted by flow cytometry with sample acquisition on DIVA software and data analysis on Flowjo software. Graphs were plotted using Prism. CD8 T effector memory cell ($T_{EM}$ cells) and CD8 T central memory cell (TCM) counts were determined for each animal from pre-dose to 14 days post-administration as illustrated in FIGS. 18A and B, respectively. Conjugate 2 induces a significant and sustained increase in CD8 effector and central memory T cell populations in cynomolgus monkeys. The figures indicate that both CD8 effector and central memory T cell populations proliferate in response to exemplary Conjugate 2.

Example 13

Evaluation of Antitumor Activity in CT26-Induced Subcutaneous Lung Metastasistumor Model in Balb/C Mice At day 0, 6-8 week-old female Balb/c mice were inoculated with 1×10⁵ mouse CT-26 cells by tail vein injection. On day 1, post 24 h of CT-26 cells being administered, mice were divided into ten groups. Each group consisted of 6-9 animals (for Conjugate 2) or 9-12 animals (for Conjugate 1). (Two separate studies were conducted for administration of Conjugate 1 and Conjugate 2, although the study protocol was essentially the same in both studies). Each group was assigned one intervention as follows: vehicle, phosphate buffered saline (Group A); native IL-15 alone (Group B); Conjugate 2 at a dose of 0.03 mg/kg (Group C); Conjugate 2 at a dose of 0.1 mg/kg (Group D); Conjugate 2 at a dose of 0.3 mg/kg (Group E); Conjugate 2 at a dose of 1.0 mg/kg (Group F); Conjugate 2 at a dose of 3.0 mg/kg (Group G); for Conjugate 1: vehicle, phosphate buffered saline (Group H); Conjugate 1 at a dose of 0.03 mg/kg (Group I) and Conjugate 1 at a dose of 0.3 mg/kg (Group J). Animals were dosed at days 1, 5, and 10.

Post 13 days from the date of CT-26 tumor cells administration, mice were anesthetized, and blood and spleen cells were collected for further analysis of immunophenotype markers, while lungs were fixed for 24-48 h in Bouins solution containing picric acid and formaldehyde.

The number of lung tumor nodules were counted under a dissection per each lung and mean of lung nodules for each group was determined. The statistical significance was also obtained between the vehicle group vs intervention groups using unpaired students t test.

Figure 19:
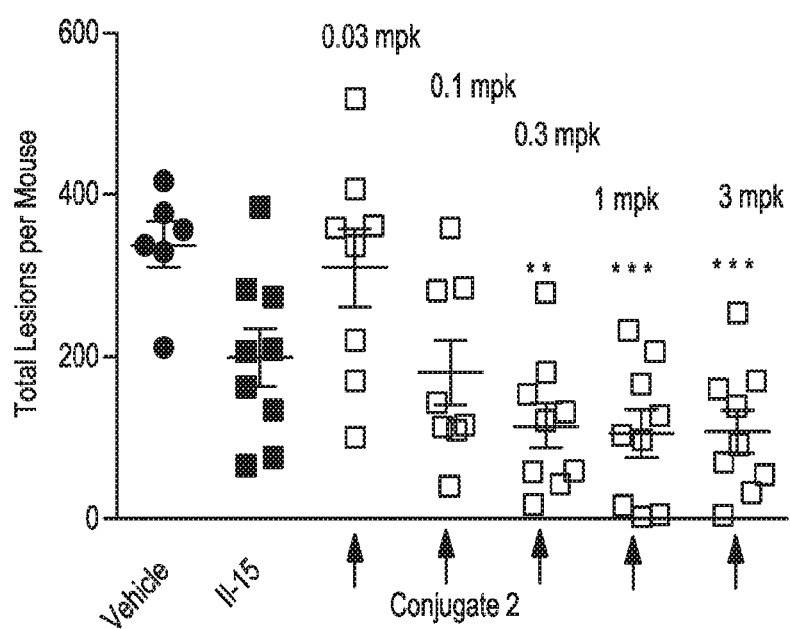
FIG. 19 illustrates total lesions per mouse in the lungs of female Balb/c mice inoculated with mouse CT-26 colon cancer cells, followed by treatment with one of the following test articles: vehicle, phosphate buffered saline (Group A); native IL-15 alone (Group B); Conjugate 2 at a dose of 0.03 mg/kg (Group C); Conjugate 2 at a dose of 0.1 mg/kg (Group D); Conjugate 2 at a dose of 0.3 mg/kg (Group E); Conjugate 2 at a dose of 1.0 mg/kg (Group F); Conjugate 2 at a dose of 3.0 mg/kg (Group G) as described in detail in Example 13.
Figure 20:
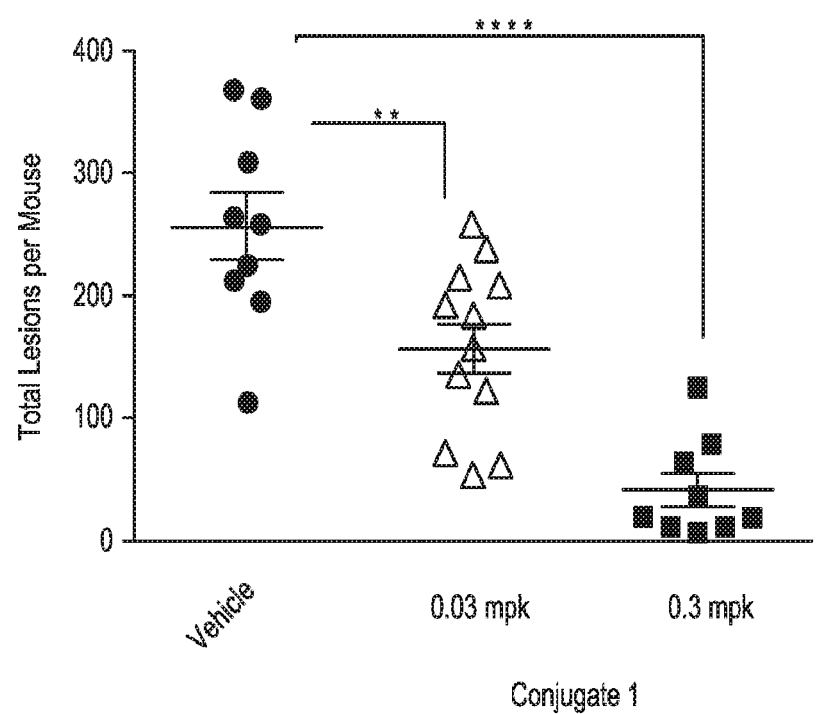
FIG. 20 illustrates total lesions per mouse in the lungs of female Balb/c mice inoculated with mouse CT-26 colon cancer cells, followed by treatment with one of the following test articles: vehicle, phosphate buffered saline (Group A); Conjugate 1 at a dose of 0.03 mg/kg (Group H); and Conjugate 1 at a dose of 0.3 mg/kg, as described in detail in Example 13.

Lung metastasis results are shown in FIGS. 19 and 20 for treatment groups corresponding to Conjugate 2 and Conjugate 1, respectively. While both illustrative long-acting IL-15 receptor agonists were effective in promoting reduction of lung metastases, Conjugate 2 provided a 65% reduction in metastases in comparison to vehicle, while Conjugate 1 provided an 85% reduction of metastases.

Blood and spleenocytes were analyzed on Day 13 for the changes in the immunophenotypic markers using flow cytometry and marker antibodies conjugated with various fluorochromes. Conjugate 2 administered at 0.3, 1, and 3 mg/kg induced a dose-dependent increase of CD8 T cells 1.5, 2.5, and 3.3-fold versus vehicle in blood, respectively. Similar observations were made in spleen with increases of 1.3, 1.7, and 2.2-fold at 0.3, 1, and 3 mg/kg dose levels versus vehicle. Ki-67 immunophenotyping revealed significant dose-dependent increases in CD8 T cell proliferation in blood with 1.7,4.6, and 5.3-fold changes and spleen with 2.5, 5.7, and 6.9-fold changes at the same low, mid, and high dose levels compared to vehicle. In addition, Conjugate 2 treatment increased pro-survival Bcl-2+ MFI in CD8 as much as 1.5-fold in both blood and spleen.

TABLE 8

| Group | Test Article | Dose (mg/kg) | Schedule | Route | Number of animals |
|---|---|---|---|---|---|
| A | Vehicle Control | | once | i.v. | 6 |
| B | IL-15 | 0.3 | days 1, 5 and 10 | i.v. | 9 |
| C | Conjugate 2 | 0.03 | days 1, 5 and 10 | i.v. | 8 |
| D | Conjugate 2 | 0.1 | days 1, 5 and 10 | i.v. | 8 |
| E | Conjugate 2 | 0.3 | days 1, 5 and 10 | i.v. | 9 |
| F | Conjugate 2 | 1.0 | days 1, 5 and 10 | i.v. | 9 |
| G | Conjugate 2 | 3.0 | days 1, 5 and 10 | i.v. | 9 |
| H | Vehicle Control | | once | i.v. | 9 |
| I | Conjugate 1 | 0.03 | days 1, 5 and 10 | i.v. | 12 |
| J | Conjugate 1 | 0.3 | Days 1 and 5 (two doses only) | i.v. | 9 |

Example 14

In Vitro and in Vivo Cytotoxicity of NK Cells Following Treatment with Conjugate 1

NK cell-mediated cytotoxicity against target tumor cells was evaluated in vitro using a flow cytometry-based assay. NK cells were isolated from spleens of Balb/c mice using negative-selection magnetic cell isolation (Mouse NK cell enrichment kit, Stemcell Technologies) and used as effector cells. For in vitro studies, isolated NK cells were stimulated with Conjugate 1 at concentrations of 3000, 1000, 300, 30, 3, or 0 (unstimulated) ng/mL overnight in a humidified incubator at 37° C., 5% $CO_2$ prior to use in the cytotoxicity assay. For in vivo studies, mice were dosed with 0.3 mg/kg Conjugate 1, and splenic NK cells were isolated 24, 48, and 72 h post-dose and used directly in the cytotoxicity assay.

YAC-1 T-cells labeled with PKH26 were used as target cells. To monitor NK cell cytotoxicity, NK and YAC-1 cells were co-cultured at various effector:target ratios (50:1, 25:1, and 12.5:1) for 4 hours at 37° C., 5° $ACO_2$, then stained with 7-AAD for 10 min to label dead cells. Cells were immediately analyzed using flow cytometry. Lysed target cells were identified as PKH26⁺7-AAD⁺.

Figure 21:
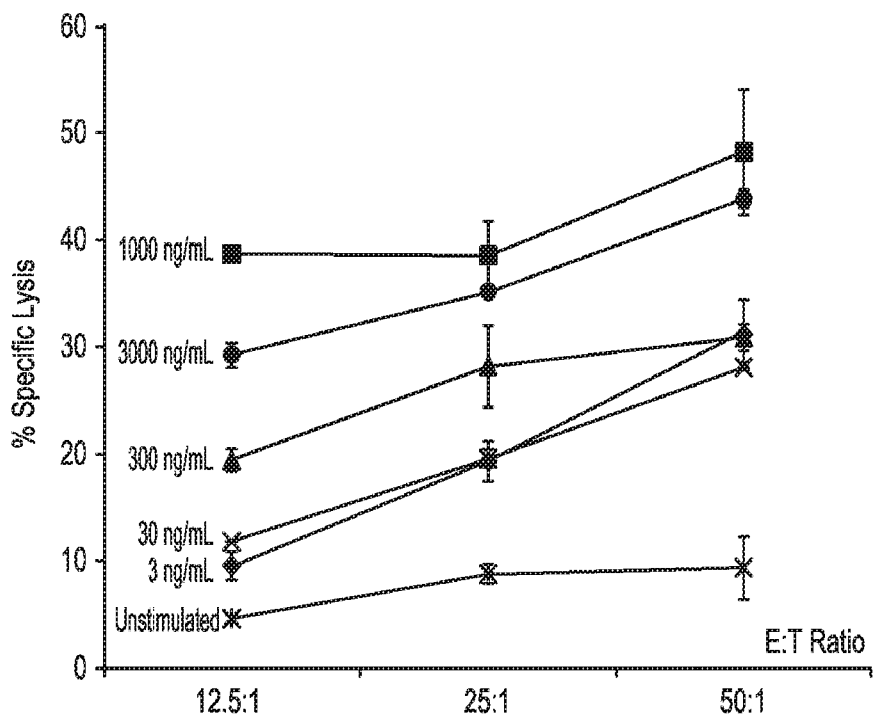
FIG. 21 illustrates the percent specific lysis as a function of E:T (effector:target) ratio at 1000 ng/mL (squares), 3000 ng/mL (circles), 300 ng/mL (triangles), 30 ng/mL (upper Xs), 3 ng/mL (diamonds), and unstimulated (lower Xs), as described in Example 14. This data illustrates dose-dependent increased cytotoxicity of NK cells in vitro following culturing with Conjugate 1.
Figure 22A:
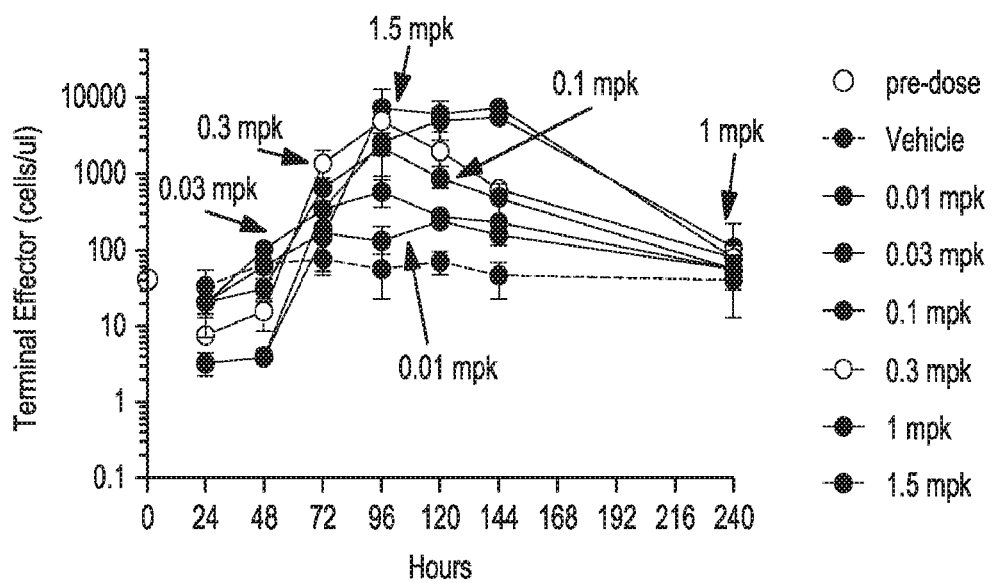
FIGS. 22A-D are plots illustrating increasing numbers of NK cells of all maturation levels in mice following i.v. administration of Conjugate 1 at doses of 0.01 mg/kg, 0.03 mg/kg, 0.1 mg/kg, 0.3 mg/kg, 1 mg/kg, and 1.5 mg/kg, as described in Example 11.
Figure 22B:
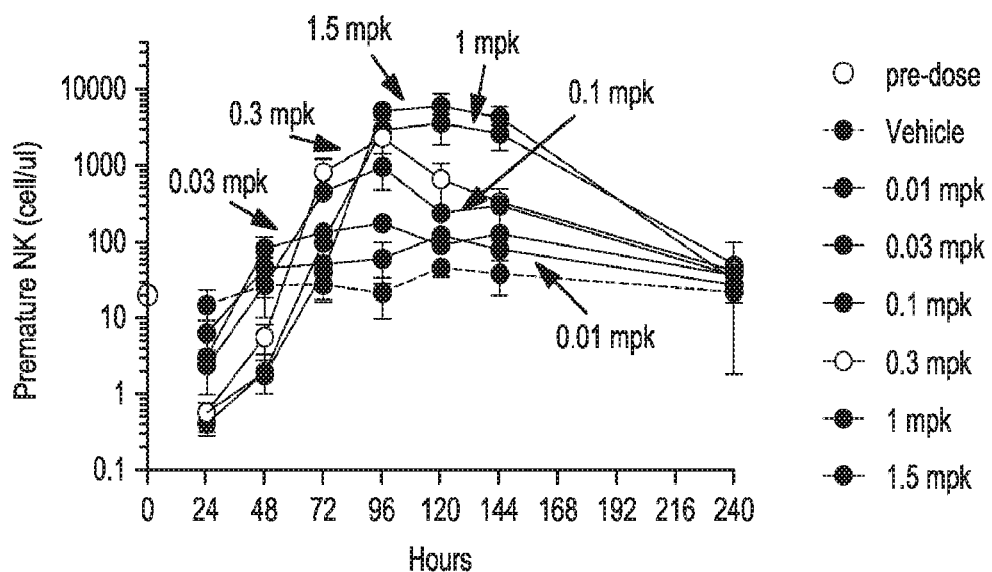
Figure 22C:
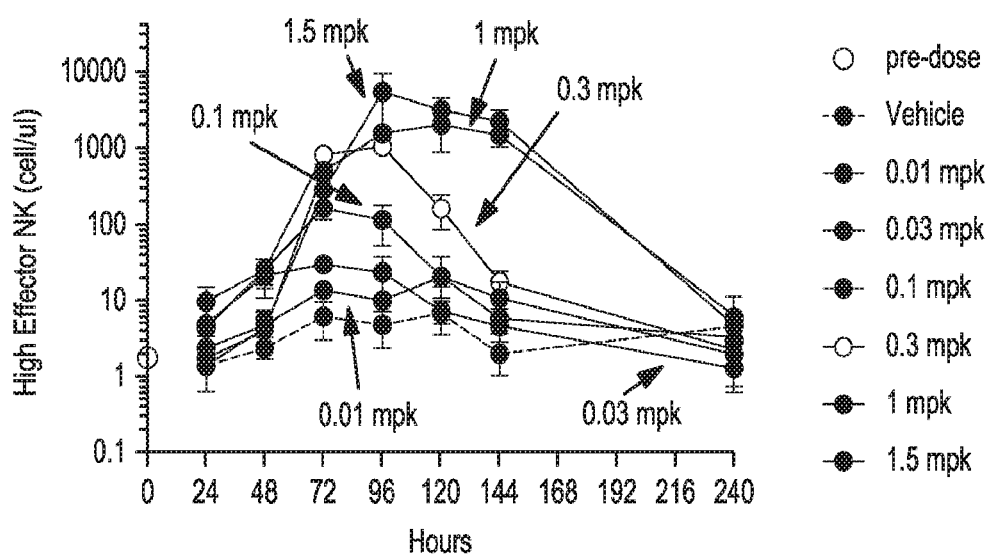
Figure 22D:
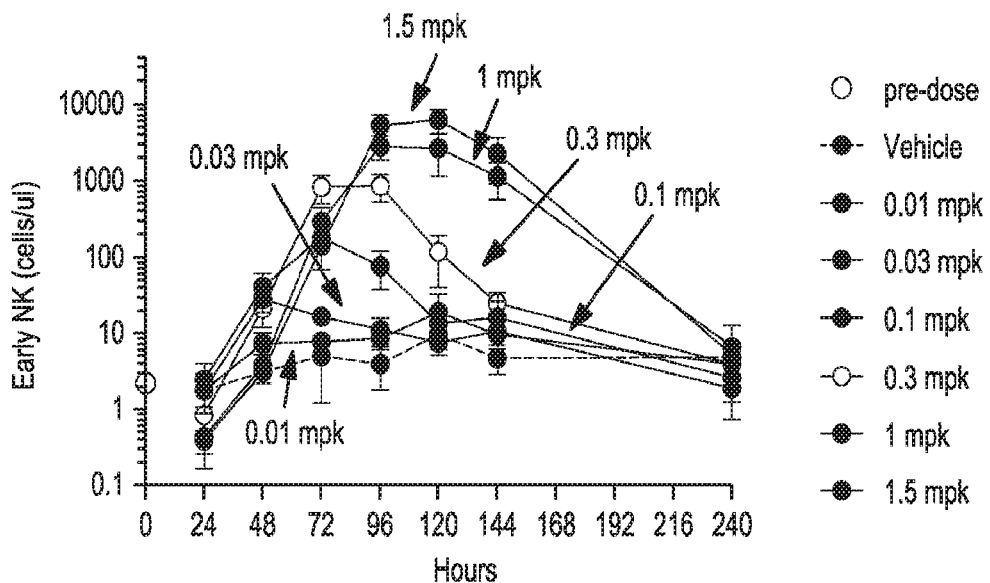

In Vitro Results: After co-culturing for 4 hours, cytotoxicity was assessed by flow cytometry. The results are provided in FIG. 21.

Figure 27:
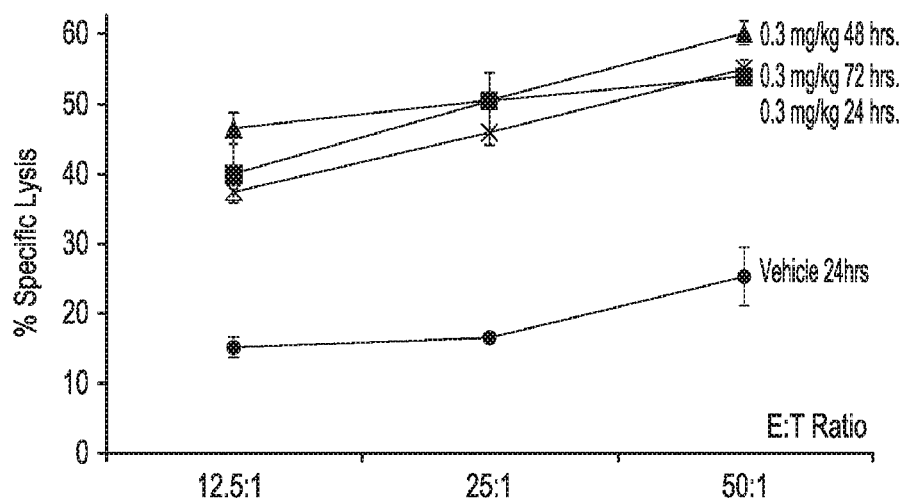
FIG. 27 is a plot illustrating in vivo cytotoxicity results after treatment with Conjugate 1 at 0.3 mg/kg, as described in Example 14. Cytotoxicity was assessed at 24 hours, 48 hours, and 72 hours following treatment.

In Vivo Results: After treatment at 0.3 mg/kg, cytotoxicity was assessed following 24 hours, 48 hours, and 72 hours. The results are provided in FIG. 27.

This data illustrates dose-dependent increased cytotoxicity of NK cells in vitro and in vivo following treatment with Conjugate 1.

Example 15

Induction of Granzyme B by Conjugate 1

NK-cell Granzyme B expression as a function of time was measured following treatment with Conjugate 1 at doses of 0.01 mg/kg, 0.03 mg/kg, 0.1 mg/kg, 0.3 mg/kg, 1 mg/kg, and 1.5 mg/kg. Whole blood was collected from 24 to 240 hours post-dose for immunophenotyping. Once red blood cells were lysed, white blood cells were labeled with viability dye and markers specific for CD45, CD3 and CD49b to identify live NK cells. Cells were then simultaneously fixed and permeabilized for intracellular Granzyme B staining. Stained blood was run on a Fortessa flow cytometer, acquired by DIVA software and analyzed using Flowjo software. Data is represented as percent of NK cells that were positive for Granzyme B expression.

Figure 23:
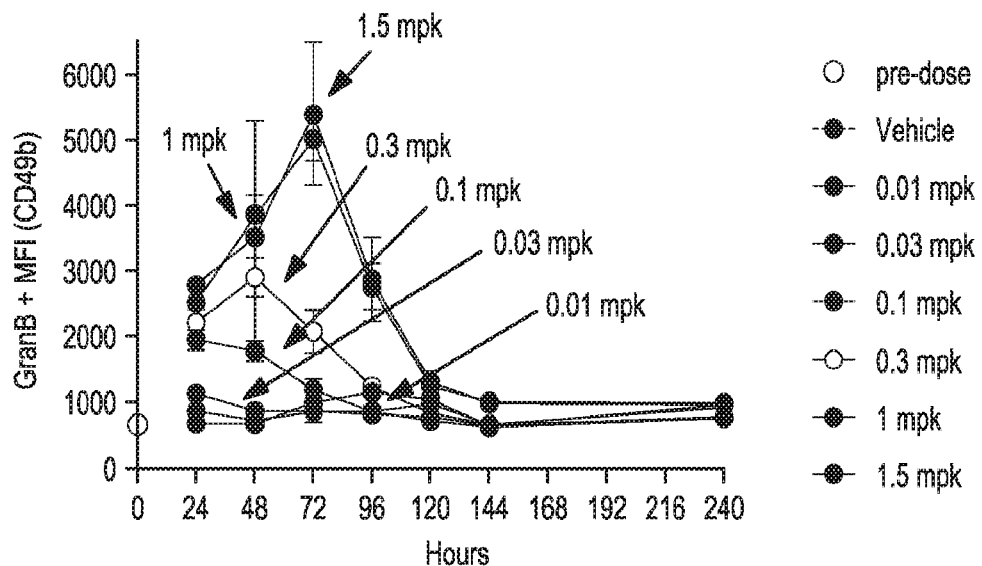
FIG. 23 is a plot illustrating Granzyme B expression as a function of time following treatment with Conjugate 1 at doses of 0.01 mg/kg, 0.03 mg/kg, 0.1 mg/kg, 0.3 mg/kg, 1 mg/kg, and 1.5 mg/kg, as described in Example 15. This data indicates treatment with Conjugate 1 increases NK-cell Granzyme B expression.

Results are provided in FIG. 23. This data indicates treatment with Conjugate 1 increases NK-cell Granzyme B expression.

Example 16

In Vivo Study: Single Dose IL-15 and Conjugate 1 PK and JAK/STAT Signaling Study in Mice For PK analysis, Conjugate 1 was administered as a single intravenous dose at 0.3 mg/kg in balb/c mice (n=3). Following administration, mice were humanely sacrificed and plasma was collected 24, 48, 72, 96, 120 and 144 hours post treatment. From a separate study, mice were administered a single intravenous dose of IL-15 (0.5 mg/kg). Samples from these mice were collected at the indicated time points within 6 hours of treatment. [PK methods previously described herein]. For pharmacodynamic examination, balb/c mice (n=/group) received i.v. injection of Conjugate 1 at 0.03 or 0.3 mg/kg or vehicle (50 mM sodium phosphate, 100 mM sodium chloride, 10% sucrose, pH7.4) and blood was collected pre-dose and 15 min, 1, 24, 48, 72, 96 and 120 hours after treatment. Samples were analyzed individually by flow cytometry and expressed as pSTAT5 percent positivity within CD8 and NK cells.

Figure 29A:
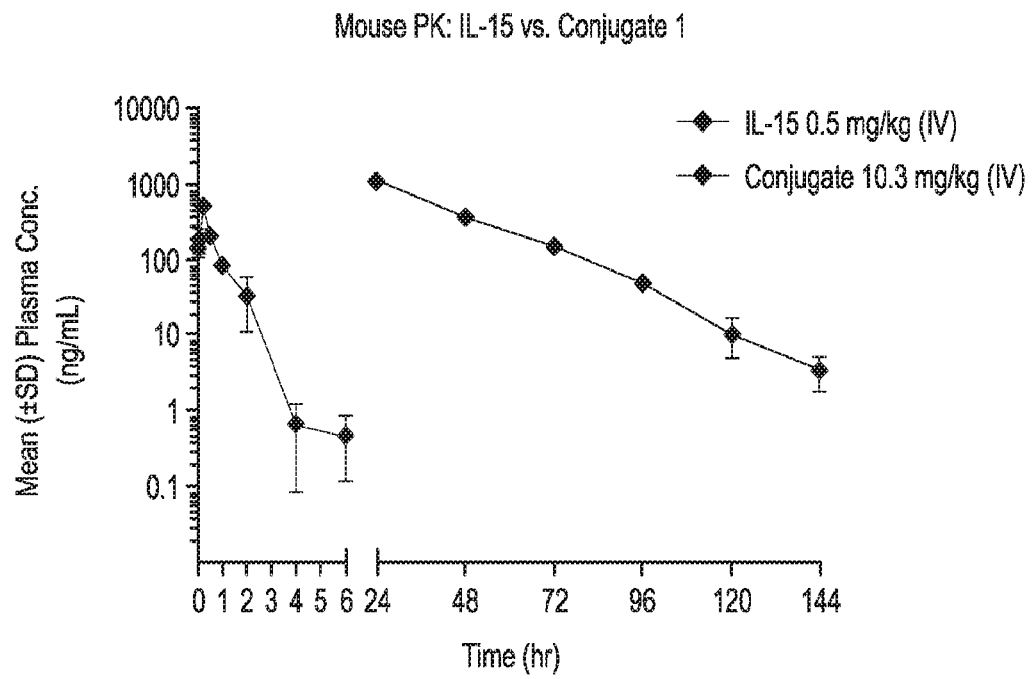
FIGS. 29A-C are plots related to the study described in Example 16.

FIG. 29A is a plot of plasma concentration of test article (IL-15 or Conjugate 1) during a 144 hour time course following administration of a single intravenous dose of test articles in balb/c mice at 0.5 and 0.3 mg/kg, respectively.

Results: Conjugate 1 exhibits a half-life of approximately 12 hours, whereas IL-15 is quickly cleared from the plasma with a half-life of less than 1 hour.

Figure 29B:
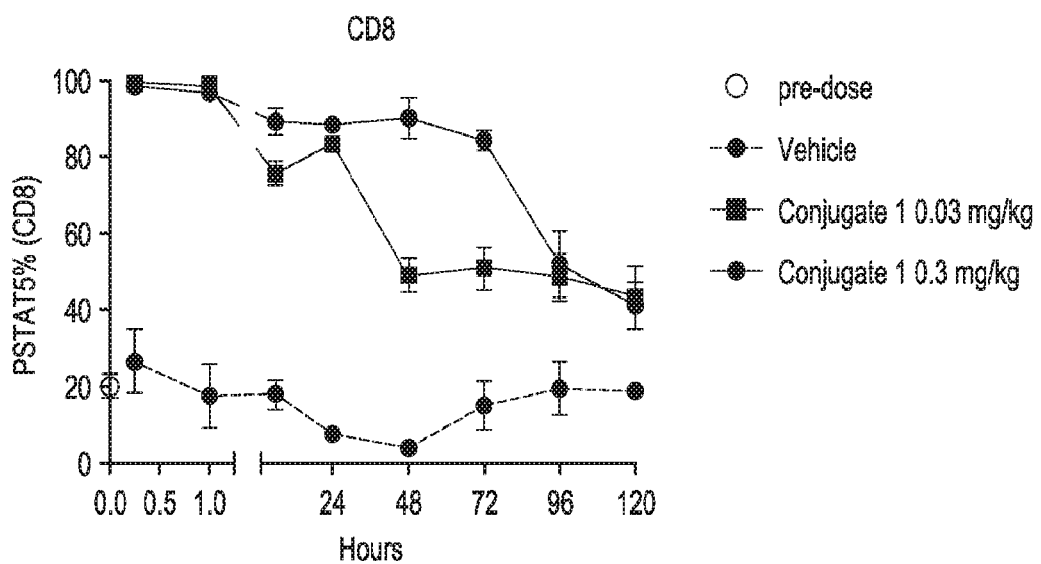

FIG. 29B is a graph of pSTAT5 percent positivity within CD8 T cells in mice after a single injection of Conjugate 1 at 0.03 and 0.3 mg/kg.

Results: Conjugate 1 at both dose levels induces sustained pSTAT5 signaling in CD8 T cells. A 120-hour time course, including pre-dose, is shown.

Figure 29C:
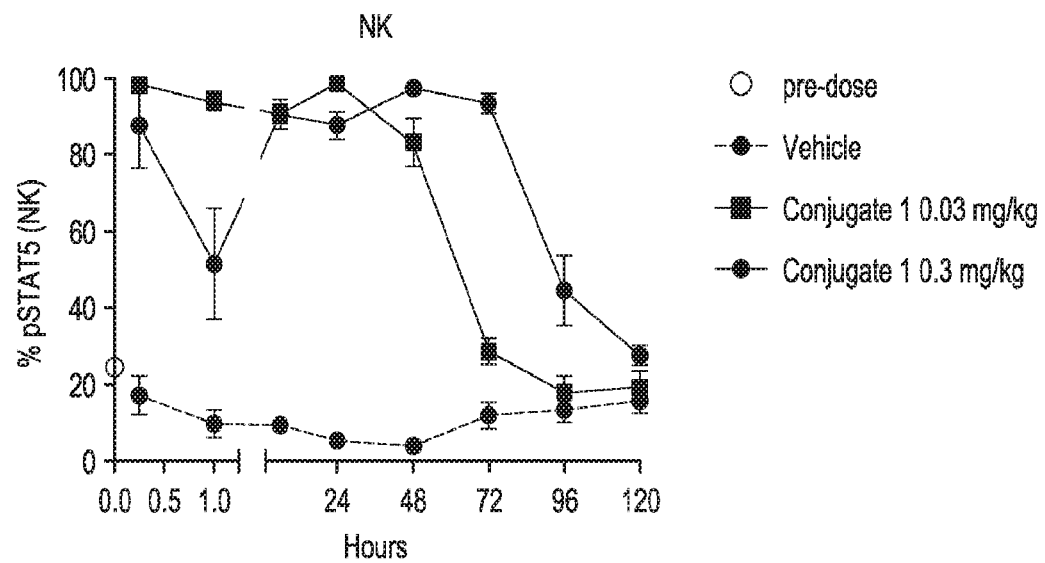

FIG. 29C is a graph of pSTAT5 percent positivity within murine NK cells after a single injection of Conjugate 1 at 0.03 and 0.3 mg/kg.

Results: Conjugate 1 at both dose levels induces robust and sustained pSTAT5 signaling in NK cells.

Example 17

In Vivo Single and Q7DX3 Pharmacodynamic Study in Mice—Cell Numbers and Proliferation Balb/c mice (n=3/group) were administered a single dose or weekly doses, thrice, of Conjugate 1 at 0.01, 0.03, 0.1, 0.3, 1 or 1.5 mg/kg or vehicle. Mice were sacrificed and blood was collected at various time points post-administration (24, 48, 72, 96, 120, 144, 240 hours). Samples from each mouse were subject to flow cytometric analysis to examine pharmacodynamic effects within lymphocyte populations and functional marker of interest (cell counts of CD8 T cells, CD8 memory T cells and NK cells and percent positivity of Ki-67 within each population). Results are shown in FIGS. 30A-F, 31A-C, and 32A-C.

FIGS. 30A-C are plots of total CD8, CD8 central memory (Tcm) and CD8 effector memory (Tem) cell numbers, respectively, after a single administration of Conjugate 1 at 0.01, 0.03, 0.1, 0.3, 1 or 1.5 mg/kg, as described in Example 17. Conjugate 1 at dose levels equal to or greater than 0.03 induce a significant increase in total CD8 T cells in the blood as described in Example 17. The lowest dose of 0.01 mg/kg increased CD8 Tcm and CD8 Tem. At 0.3 mg/kg, Conjugate 1 increased CD8, CD8 Tcm and CD8 Tem by 6.4×, 37.9× and 14.5×. Notably, CD8 and CD8 memory T cell numbers did not return to baseline at 240 hours post injection when Conjugate 1 was dosed at 0.3-1.5 mg/kg, demonstrating the sustained PD effects of Conjugate 1.

FIGS. 30D, 30E and 30F are plots of Ki-67 percent positivity within total CD8, CD8 Tcm and CD8 Tem populations, respectively, in mice, as described in Example 17. A single dose of Conjugate 1, at all dose levels, increases Ki-67 positivity in all CD8 and CD8 subpopulations.

Figure 31A:
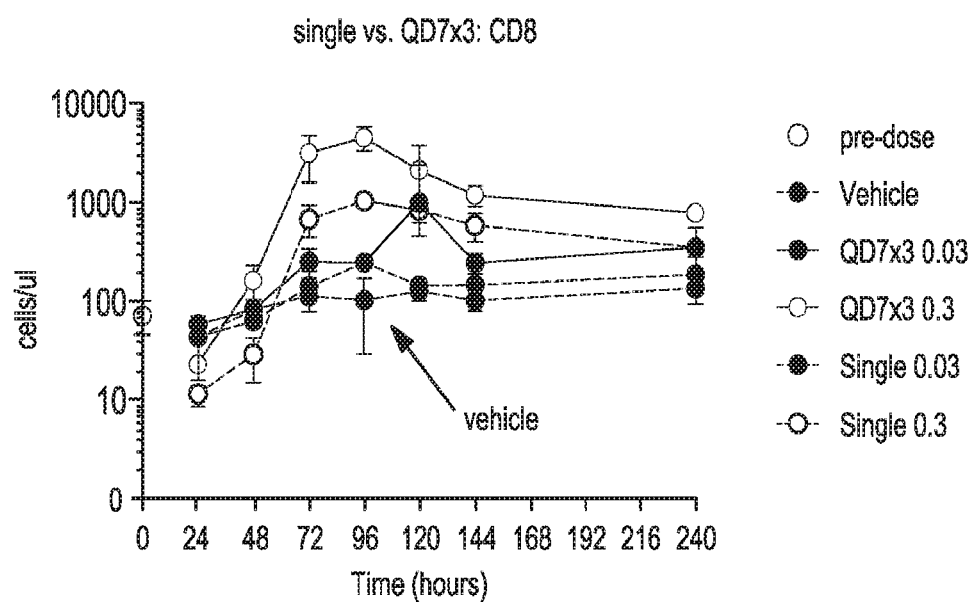
FIGS. 31A, 31B and 31C are plots of CD8 and CD8 memory subpopulation T cell numbers after Conjugate 1 was dosed singly (dotted lines) or Q7dx3 (solid lines) at 0.03 and 0.3 mg/kg as described in Example 17. Repeated dosing increased these populations further with CD8, CD8 Tcm, CD8 Tem increases of 35.3×, 183× and 73.8×, respectively. At the end of the time course (240 hours after first or last dose at 0.3 mg/kg), cell numbers had not returned to baseline in mice.
Figure 31B:
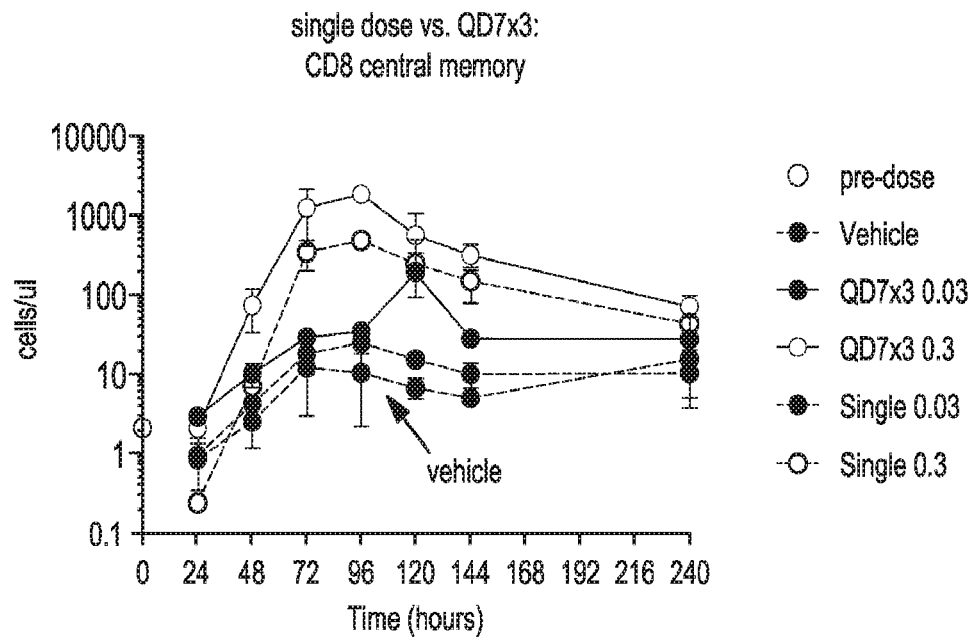
Figure 31C:
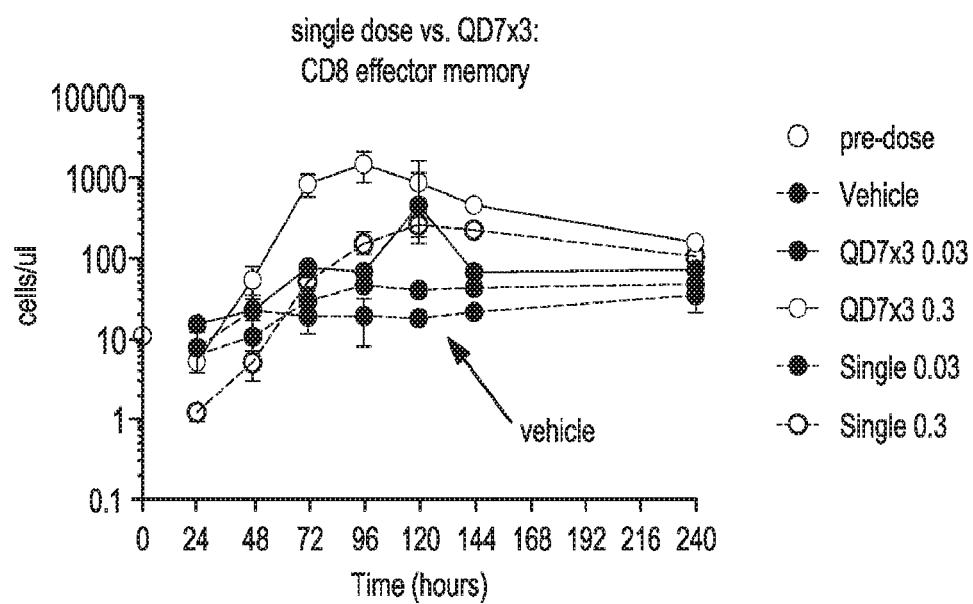

FIGS. 31A, 31B and 31C are plots of CD8 and CD8 memory subpopulation T cell numbers after Conjugate 1 was dosed singly (dotted lines) or Q7dx3 (solid lines) at 0.03 and 0.3 mg/kg as described in Example 17. Repeated dosing increased these populations further with CD8, CD8 Tcm, CD8 Tem increases of 35.3×, 183× and 73.8×, respectively. At the end of the time course (240 hours after first or last dose at 0.3 mg/kg), cell numbers had not returned to baseline in mice.

Figure 32A:
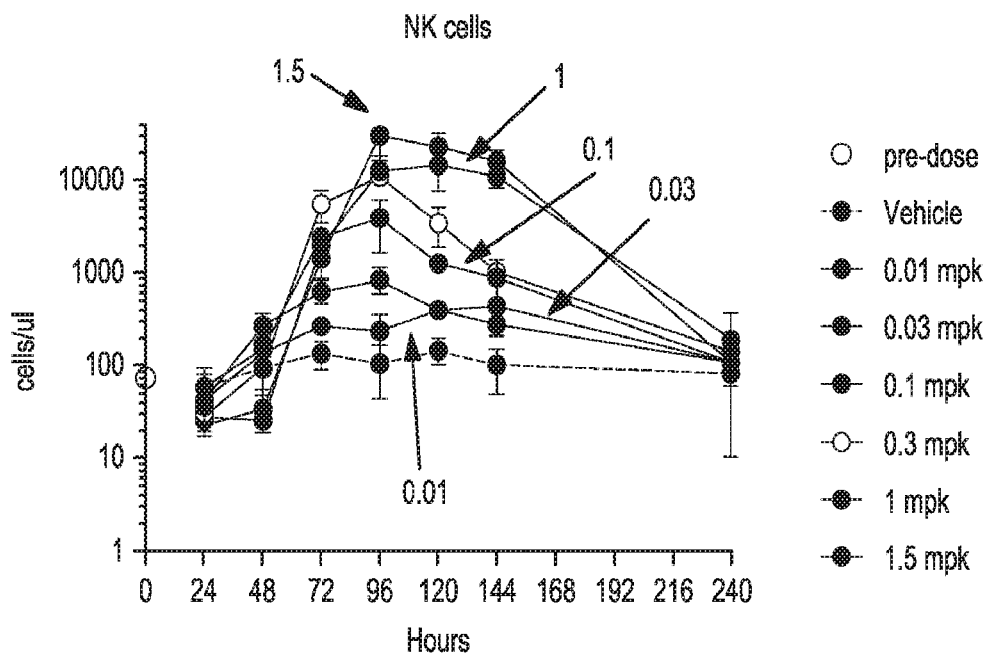
FIGS. 32A and 32B are plots of NK cell numbers and Ki-67 percent positivity after a single dose of Conjugate 1 from 0.01 to 1.5 mg/kg in mice as described in Example 17. NK cell numbers increase significantly above vehicle control at all dose levels and return back to baseline by 240 hours post dose. All dose levels induce a robust increase of Ki-67 percent positivity in NK cells.
Figure 32B:
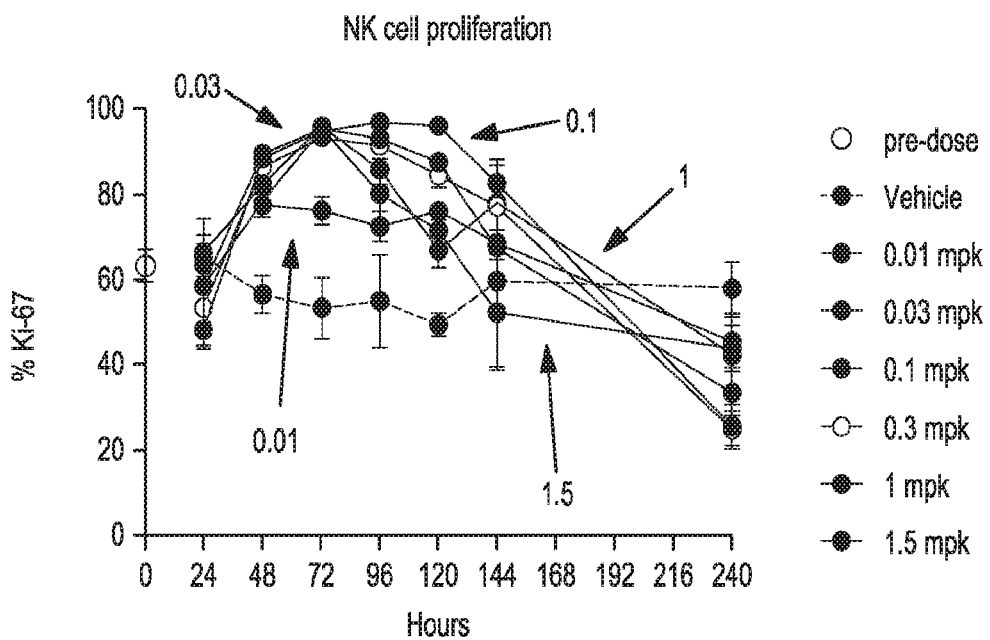

FIGS. 32A and 32B are plots of NK cell numbers and Ki-67 percent positivity after a single dose of Conjugate 1 from 0.01 to 1.5 mg/kg in mice as described in Example 17. NK cell numbers increase significantly above vehicle control at all dose levels and return back to baseline by 240 hours post dose. All dose levels induce a robust increase of Ki-67 percent positivity in NK cells.

Figure 32C:
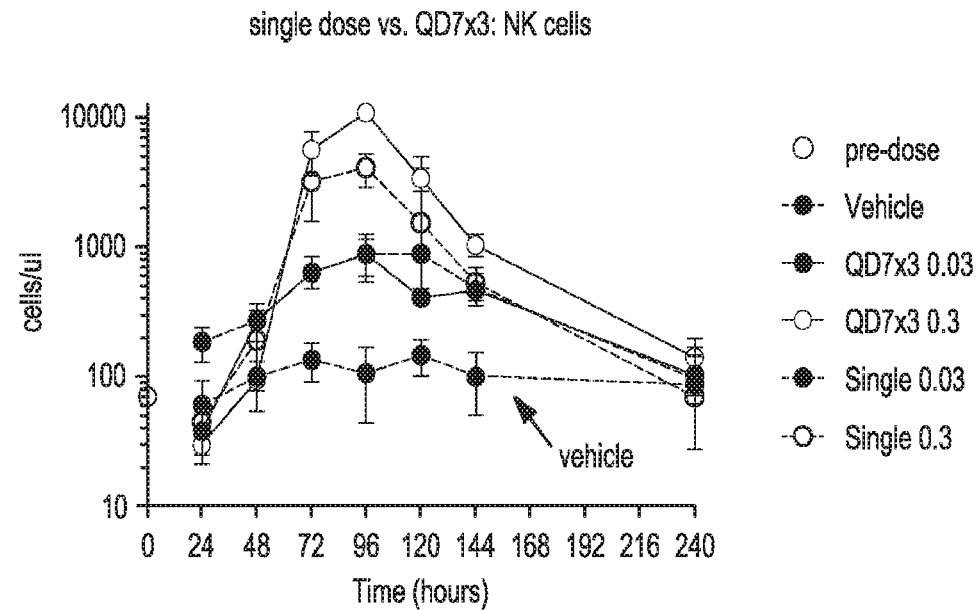
FIG. 32C is a plot of murine NK cell numbers after single (solid lines) or Q7dx3 (dashed lines) dosing of Conjugate 1 at 0.03 and 0.3 mg/kg as described in Example 17. Repeated dosing of Conjugate 1 at 0.3 mg/kg induced slightly less, although still significant, numbers of NK cells compared to a single dose. Similar NK numbers were achieved with single versus repeat dosing at 0.03 mg/kg.

FIG. 32C is a plot of murine NK cell numbers after single (solid lines) or Q7dx3 (dashed lines) dosing of Conjugate 1 at 0.03 and 0.3 mg/kg as described in Example 17. Repeated dosing of Conjugate 1 at 0.3 mg/kg induced slightly less, although still significant, numbers of NK cells compared to a single dose. Similar NK numbers were achieved with single versus repeat dosing at 0.03 mg/kg.

Results: Conjugate 1 at dose levels equal to or greater than 0.03 induces a significant increase in total CD8 T cells in the blood. The lowest dose of 0.01 mg/kg increased CD8 Tcm (central memory) and CD8 Tem (effector memory). At 0.3 mg/kg, Conjugate 1 increased CD8, CD8 Tcm and CD8 Tem by 6.4×, 37.9× and 14.5×, respectively. Notably, CD8 and CD8 memory T cell numbers did not return to baseline at 240 hours post injection when Conjugate 1 was dosed at 0.3-1.5 mg/kg, demonstrating the beneficial sustained PD effects of Conjugate 1.

Example 18

Measurement of in Vitro NK Cytotoxicity in Mice Treated with Conjugate 1 and Blood NK Cell Granzyme B Analysis Balb/c mice (n=2/group) were treated with Conjugate 1 (0.006, 0.03 or 0.3 mg/kg), IL-15 (1 mg/kg) or vehicle control. After treatment, spleens were isolated 24, 72, and 96 hours for NK cell isolation. NK cells were isolated by a magnet-based negative-selection method and incubated at 12.5:1, 25:1 and 50:1 NK (effector) to YAC-1 (target cell) ratios (E:T) for 4 hours at 37 C., 5% $CO_2$. YAC-1 target cells were pre-labeled and then stained with 7AAD after NK cell incubation. Detection of lysed (7AAD+) target cells (PKH26+) was conducted by flow cytometry. Blood from these mice was also collected at the same time points and subjected to flow cytometric measurement of NK cells' expression of Granzyme B. Results are shown in FIGS. 33A and 33B.

Figure 33A:
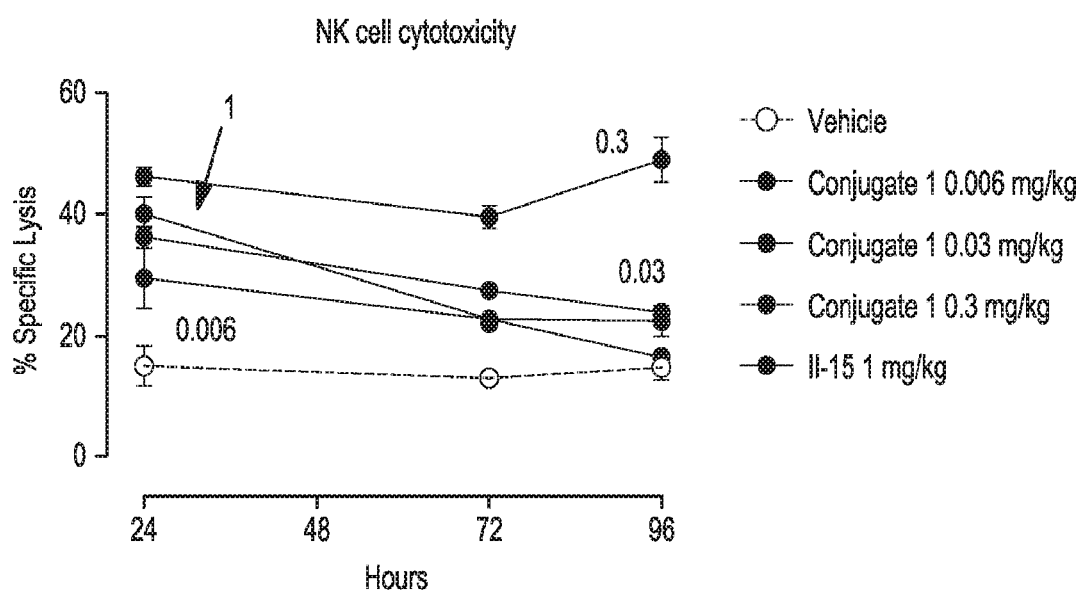
FIG. 33A illustrates an in vitro NK cytotoxicity assay that measures changes in NK-mediated target cell lysis after test article treatment in mice as described in Example 18. A time course at the indicated hours of percent specific lysis of YAC-1 cells by splenic NK cells isolated from balb/c mice treated with 0.006, 0.03 or 0.3 mg/kg Conjugate 1 or 1 mg/kg of IL-15 is shown. Splenic NK cells from mice dosed with vehicle served as a control. Conjugate 1 dosed at 0.3 mg/kg induced an elevation of NK cytotoxicity superior in magnitude and duration compared to NK cells from mice receiving a single injection of IL-15 at 1 mg/kg.

FIG. 33A illustrates an in vitro NK cytotoxicity assay that measures changes in NK-mediated target cell lysis after test article treatment in mice. A time course at the indicated hours of percent specific lysis of YAC-1 cells by splenic NK cells isolated from balb/c mice treated with 0.006, 0.03 or 0.3 mg/kg Conjugate 1 or 1 mg/kg of IL-15 is shown. Splenic NK cells from mice dosed with vehicle served as a control.

Results: Conjugate 1 dosed at 0.3 mg/kg induced an elevation of NK cytotoxicity superior in magnitude and duration compared to NK cells from mice receiving a single injection of IL-15 at 1 mg/kg.

Figure 33B:
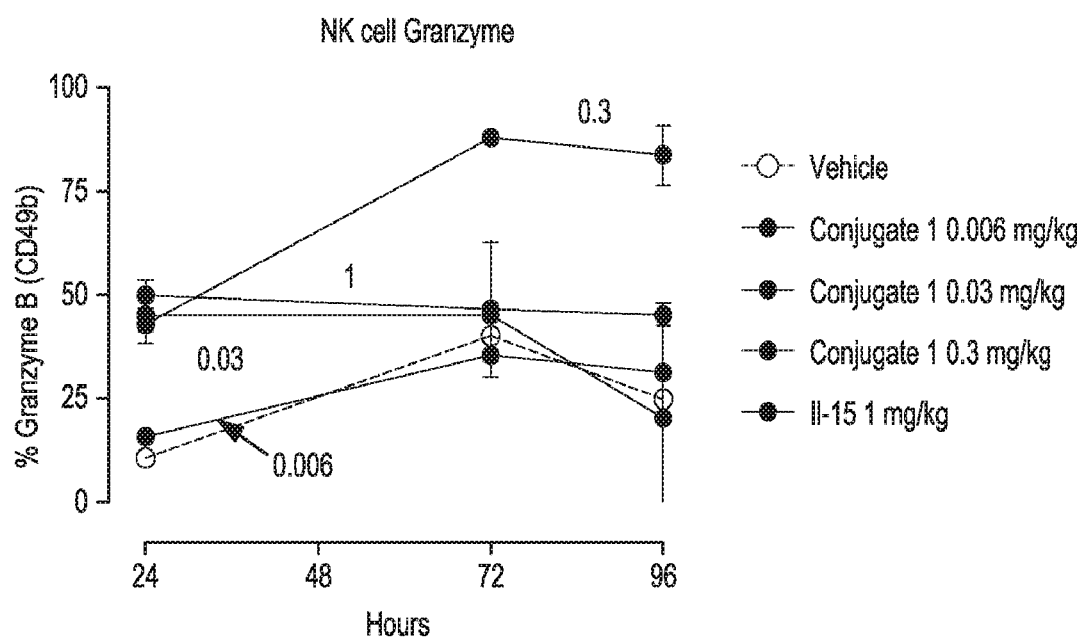
FIG. 33B is a graph of Granzyme B percent positivity in blood NK cells from the same mice devoted to the NK in vitro cytotoxicity assay in FIG. 33A. See Example 18. Conjugate 1 dosed at 0.03 and 0.3 mg/kg induced significant increases in NK Granzyme B expression, with a robust and sustained elevation seen at 0.3 mg/kg.

FIG. 33B is a graph of Granzyme B percent positivity in blood NK cells from the same mice devoted to the NK in vitro cytotoxicity assay in FIG. 33A.

Results: Conjugate 1 dosed at 0.03 and 0.3 mg/kg induced significant increases in NK Granzyme B expression, with a robust and sustained elevation seen at 0.3 mg/kg.

Example 19

Conjugate 1 Single Agent Efficacy in a Ct-26 Lung Metastasis Model

Balb/c mice received tail vein injection of $1\times10^5$ CT-26 colorectal carcinoma cells. The following day, mice (n=9/group) were treated weekly, twice, with Conjugate 1 (0.03 or 0.3 mg/kg) or vehicle control. Five days after the second injection, mice were humanely sacrificed and lung nodules were counted. Results are provided in FIGS. 34A and 34B.

Figure 34A:
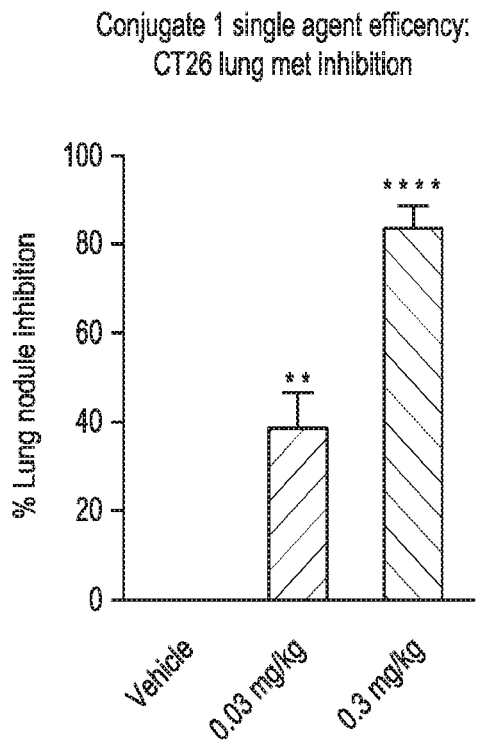
FIGS. 34A and 34B illustrate the percent lung nodule inhibition in balb/c mice receiving intravenous CT-26 tumor cell injection followed by Conjugate 1 treatment dosed twice, one week apart, at 0.03 or 0.3 mg/kg as described in Example 19. Conjugate 1 injection at 0.03 and 0.3 mg/kg inhibited lung nodule formation by 40 and 80%, respectively. The same mice dosed at 0.3 mg/kg were followed for 32 days post tumor cell injection to assess survival. Treatment with Conjugate 1 increased survival significantly compared to tumor-injected mice receiving vehicle control.
Figure 34B:
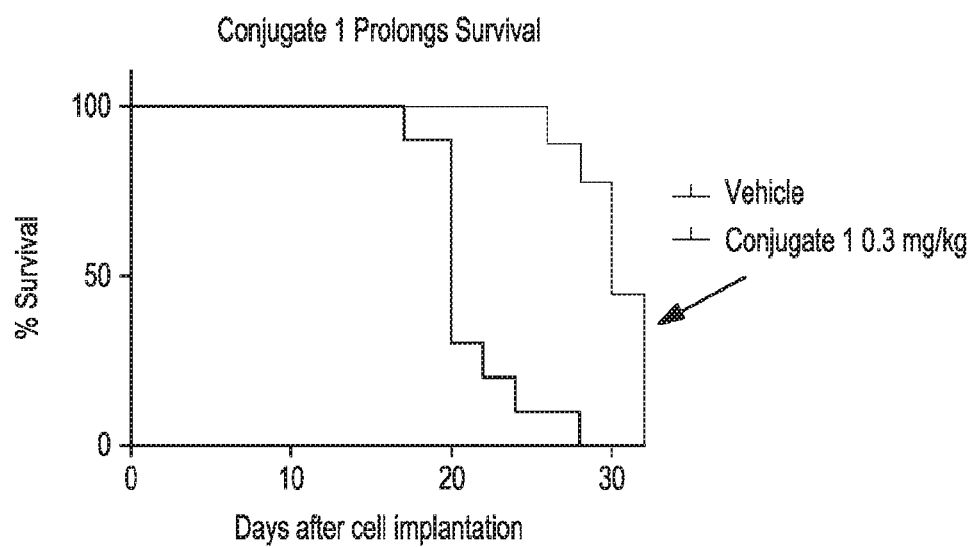

FIGS. 34A and 34B illustrate the percent lung nodule inhibition in balb/c mice receiving intravenous CT-26 tumor cell injection followed by Conjugate 1 treatment dosed twice, one week apart, at 0.03 or 0.3 mg/kg.

Results: Conjugate 1 injection at 0.03 and 0.3 mg/kg inhibited lung nodule formation by 40 and 80%, respectively. The same mice dosed at 0.3 mg/kg were followed for 32 days post tumor cell injection to assess survival. Treatment with Conjugate 1 increased survival significantly compared to tumor-injected mice receiving vehicle control.

Example 20

Assessment of NK Cell—Dependency of Conjugate 2 Efficacy in a Ct-26 Lung Metastasis Model CT-26 mice (n=7-11/group) were injected with anti-asialo GM1 to deplete NK cells or two different controls (IgG or PBS), then injected with $1\times10^5$ CT-26 tumor cells. Mice were then treated with Conjugate 2 at 0.3 mg/kg dosed on days 1, 5 and 10 post tumor cell injection or vehicle control. Mice were sacrificed and lung nodules were counted three days after the last day of treatment. Results are shown in FIG. 35.

Figure 35:
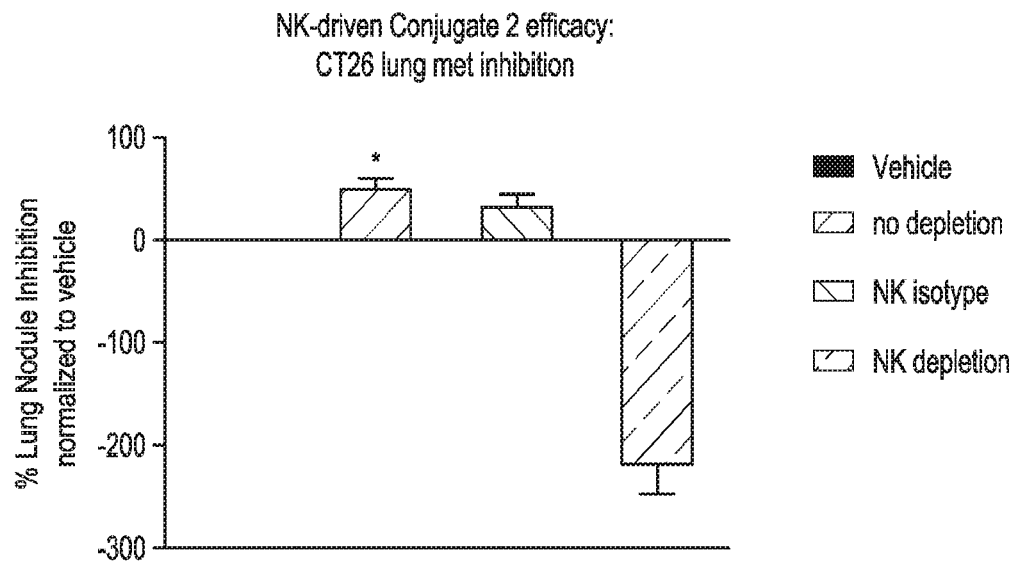
FIG. 35 is a graph of percent lung nodule inhibition in CT-26-injected mice treated with Conjugate 2, that received antibody-mediated depletion of NK cells (olive green), IgG control (blue), or PBS (Orange) as described in Example 20. Data is represented as percent lung nodule inhibition relative to CT-26-injected mice that were not NK cell depleted and treated with a vehicle control (black). Conjugate 2 efficacy in this tumor model was abolished when mice lacked NK cells.

FIG. 35 is a graph showing percent lung nodule inhibition in CT-26-injected mice treated with Conjugate 2, that received antibody-mediated depletion of NK cells (olive green), IgG control (blue), or PBS (Orange). Data is represented as percent lung nodule inhibition relative to CT-26-injected mice that were not NK cell depleted and treated with a vehicle control (black). Conjugate 2 efficacy in this tumor model was abolished when mice lacked NK cells.

Example 21

In Vivo Pharmacodynamic Study of Conjugate 1 Single Dose in Non-Human Primates

In this study, cynomolgus monkeys (cyno), one female and one male, were each intravenously administered a single dose of Conjugate 1 (0.1 mg/kg). A series of blood samples were taken from each animal over a 14-day time course and subjected to flow cytometry analysis of various lymphocytes (CD8 T cells, Ki-67 percent positivity within total CD8, CD8 central memory T cells (Tcm) and CD8 effector memory T cells (Tem), NK cells and Ki-67 percent positivity of NK cells). Results are provided in FIGS. 36A-D and 37A-B.

Figure 36A:
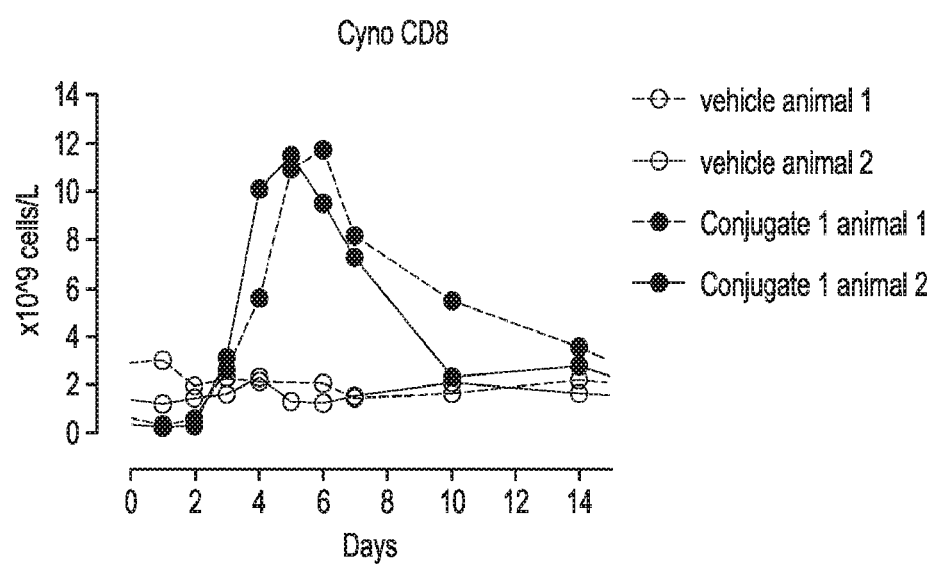
FIGS. 36A and 36B are plots illustrating a two week time course for CD8 cell numbers and Ki-67 percent positivity as a measure of proliferation of one male (dotted line) and one female (solid line) cynomolgus monkey ("cyno") following intravenous administration of Conjugate 1 at a dose of 0.1 mg/kg as described in Example 21. Conjugate 1 induces significant CD8 T cell increase in cyno with a 7-10X increase in cell numbers after a single dose.
Figure 36B:
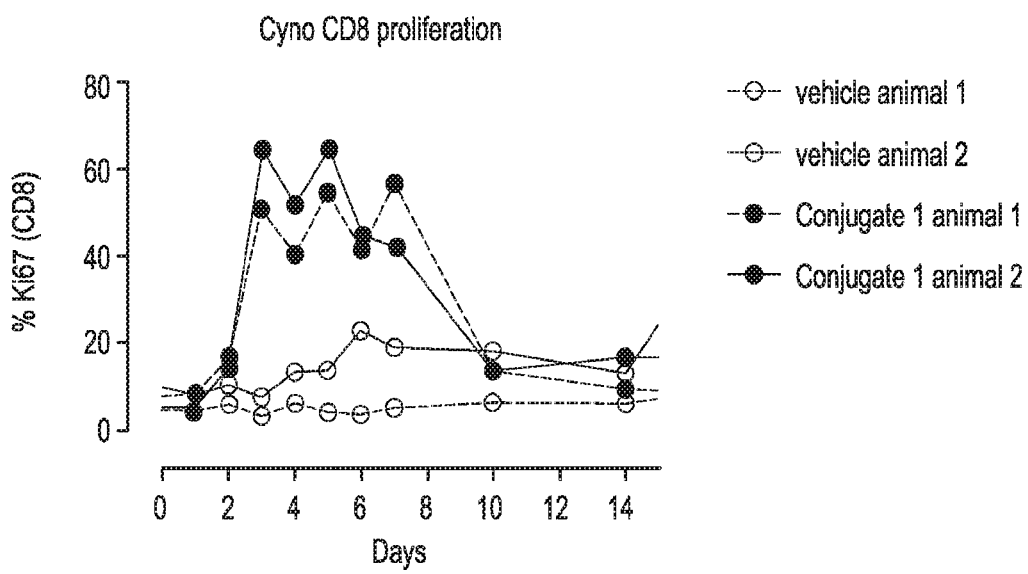

FIGS. 36A and 36B are plots illustrating a two week time course for CD8 cell numbers and Ki-67 percent positivity as a measure of proliferation of one male (dotted line) and one female (solid line) cyno following intravenous administration of Conjugate 1 at a dose of 0.1 mg/kg. As can be seen, Conjugate 1 induces significant CD8 T cell increase in cyno with a 7-10× increase in cell numbers after a single dose.

Figure 36C:
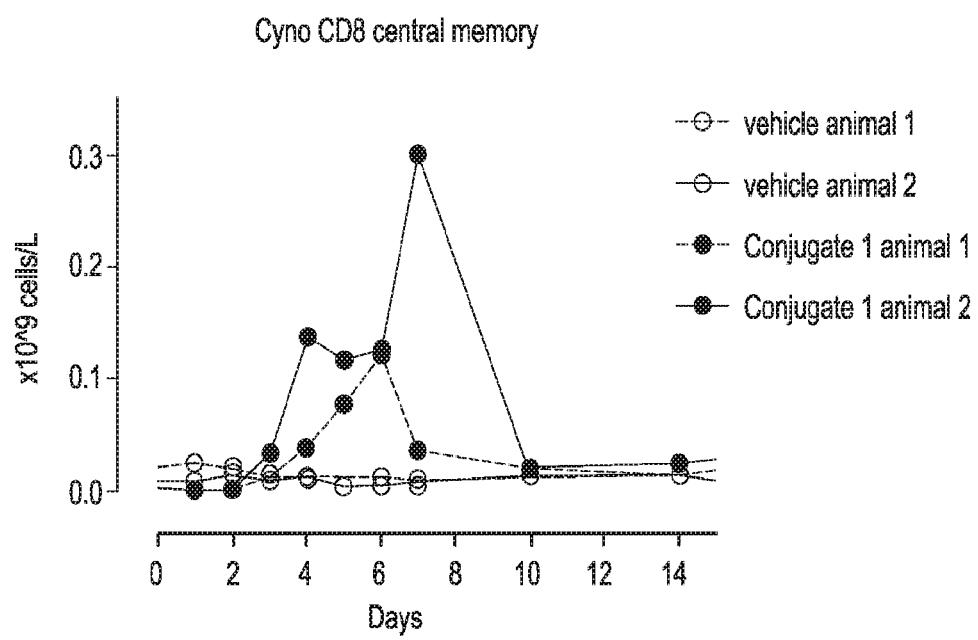
FIGS. 36C and 36D illustrate the increases in cyno CD8 Tcm and CD8 Tem cell numbers after a single injection of Conjugate 1 as described in Example 21. CD8 Tcm and Tem numbers increased 27-30× and 21-33×, respectively.
Figure 36D:
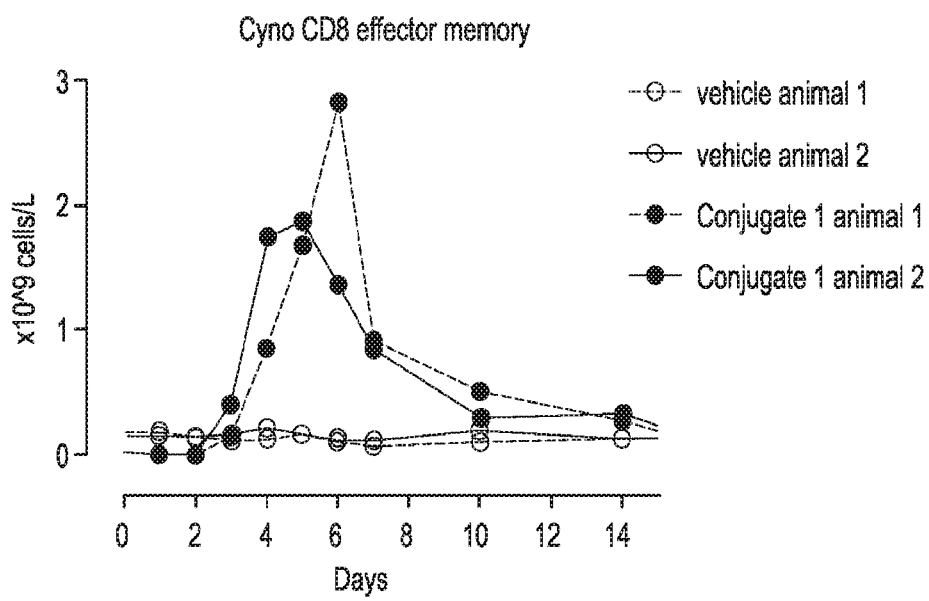

FIGS. 36C and 36D illustrate the increases in cyno CD8 Tcm and CD8 Tem cell numbers after a single injection of Conjugate 1. CD8 Tcm and Tem numbers increased 27-30× and 21-33×, respectively.

Figure 37A:
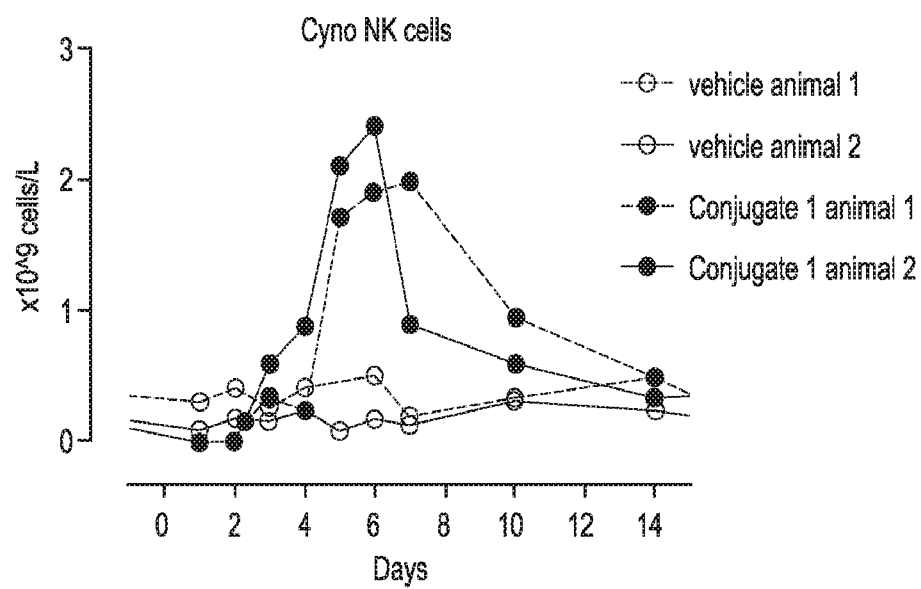
FIGS. 37A and 37B are graphs of NK cell numbers and Ki-67 percent positivity in cyno after a single dose of Conjugate 1 at 0.1 mg/kg. See Example 21. NK cells increased 9-10× after treatment with Conjugate 1.
Figure 37B:
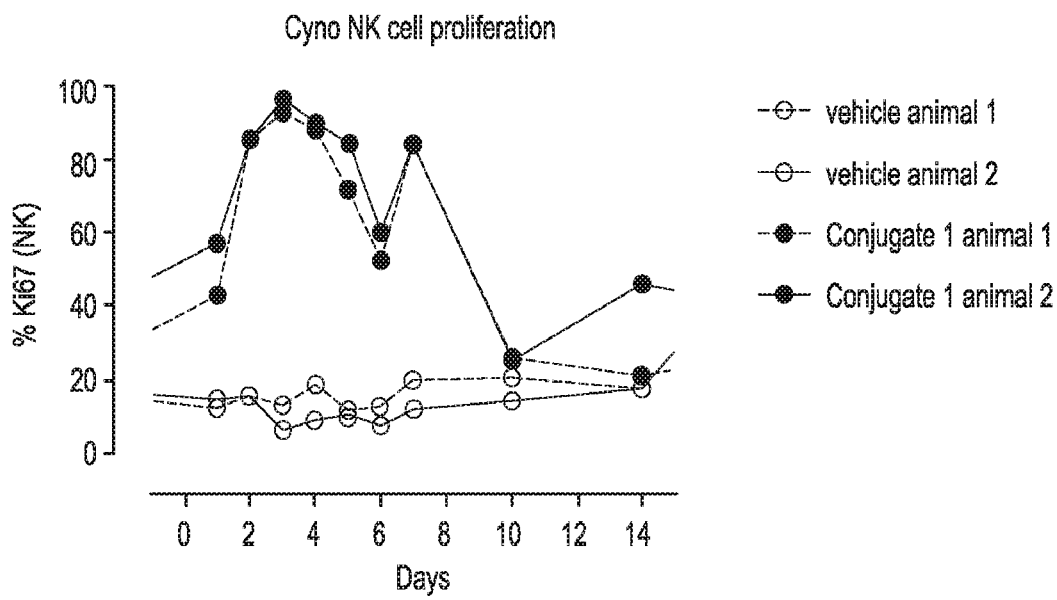

FIGS. 37A and 37B are graphs of NK cell numbers and Ki-67 percent positivity in cyno after a single dose of Conjugate 1 at 0.1 mg/kg. NK cells increased 9-10× after treatment with Conjugate 1.

Example 22

Comparison of in Vitro Activity of IL-15 and Conjugate 1 in CD8 and CD56 Bright NK Cells in Human PBMCS Assessment of in vitro activity of Conjugate 1 was carried out by investigating NK and CD8 JAK/STAT signaling after treatment of human PBMCs with IL-15 or Conjugate 1 at a dose range of 0.001-10000 ng/ml. STAT5 phosphorylation was assessed as previously described.

TABLE 9

| | EC50 (mg/ml) - % pSTAT5 | |
|---|---|---|
| Compound | CD8 | CD56 bright |
| IL-15 | 0.16 | 0.11 |
| Compound 1 | 0.87 | 1.7 |

Figure 38A:
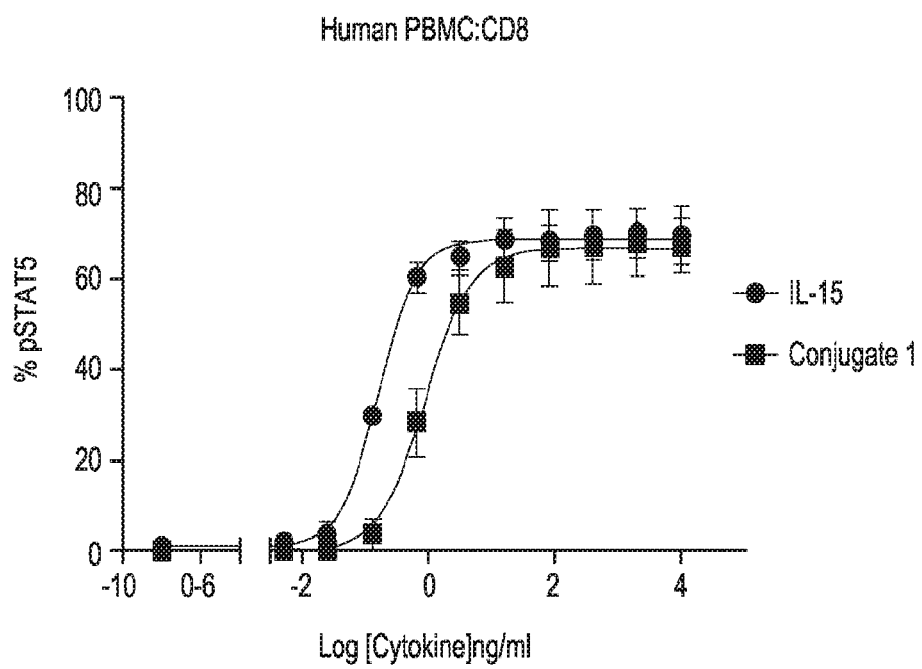
FIGS. 38A and 38B are EC50 curves for IL-15 (red, solid circle) versus Conjugate 1 (green, solid square) treatment of human PBMCs and subsequent measurement of pSTAT5 percent positivity in CD8 and CD56 bright NK cells as described in Example 22. Conjugate 1 is 5.5 and 15× less potent than IL-15 in engaging CD8 and CD56 bright NK cells, respectively. However, Conjugate 1 achieves the same maximum response as conventional IL-15.
Figure 38B:
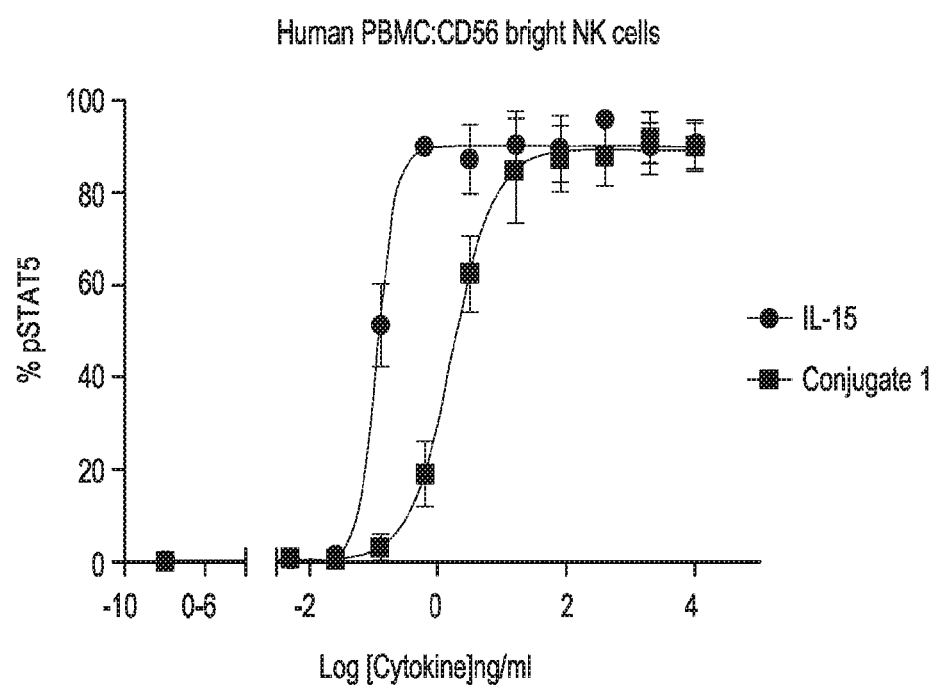

Results are provided in FIGS. 38A and 38B; these figures are EC50 curves for IL-15 (●) versus Conjugate 1 (■) treatment of human PBMCs and subsequent measurement of pSTAT5 percent positivity in CD8 and CD56 bright NK cells.

Results: Conjugate 1 is 5.5 and 15× less potent than IL-15 in engaging CD8 and CD56 bright NK cells, respectively. Importantly, however, Conjugate 1 achieves the same maximum response as conventional IL-15.

Example 23

In Vivo Study: Single Dose PK Study in Mice

Balb/c mice (n=3/group) were administered a single intravenous dose of IL-15 (500 ug/kg) or Conjugate 1 at 10, 30, 100, 300 and 1000 µg/kg. Blood samples were collected at the indicated time points post administration (conjugate 1: 24, 48, 72, 96, 120, 144, 240 hours; IL-15 control: 0.03, 0.08, 0.25, 0.5, 1, 2, 4, 6, 8, hours) and plasma concentration of drug was determined. See FIG. 39.

Figure 39:
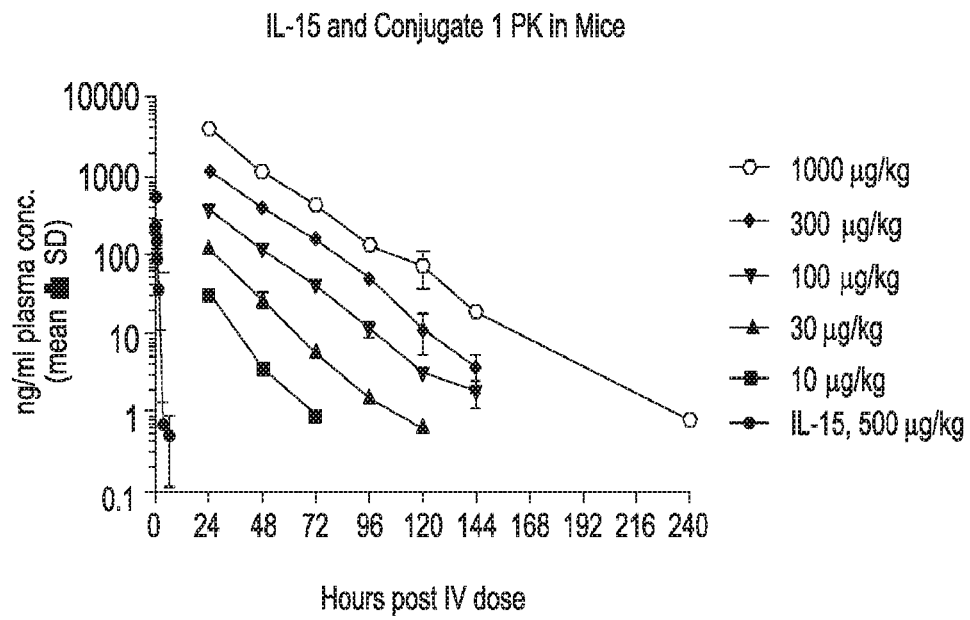
FIG. 39 is a plot of plasma concentration IL-15 at 500 μg/kg (green, solid circles) or Conjugate 1 at 10 μg/kg (pink, solid squares), 30 μg/kg (purple, solid upwards triangles), 100 μg/kg (red, solid downwards-facing triangles), 300 μg/kg (orange, solid diamonds) or 1000 μg/kg (dark red, open hexagons) over time following administration of a single intravenous dose in mice as described in Example 23.

As shown in FIG. 39, Conjugate 1 showed extended pharmacokinetics, measurable concentrations in plasma, with a half-life of approximately 14 hours as compared to plasma levels observed for non-long acting IL-15, which was rapidly cleared.

Example 24

In Vivo Study: Single Dose PK Study in Rat

Sprague Dawley rats (n=3) were administered a single intravenous dose of Conjugate 1 at 10, 75 and 150 µg/kg. Plasma concentration of drug was determined at the indicated time points post injection (0.03, 0.08, 0.25, 0.5, 1, 2, 4, 8, 24, 48, 72, 96, 120, 144 hours). See FIG. 40.

Figure 40:
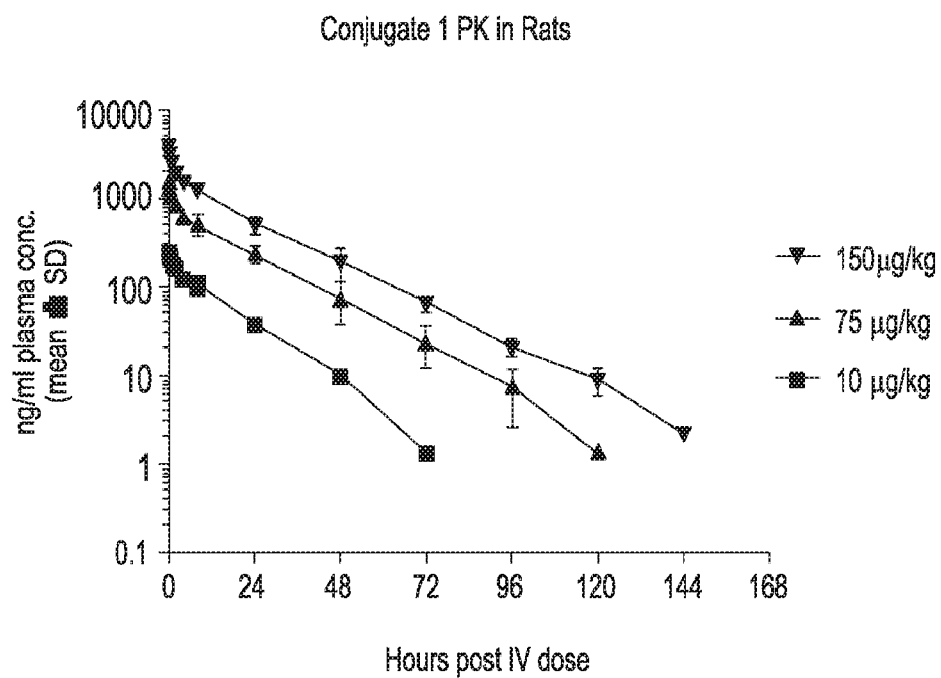
FIG. 40 is a plot of plasma concentration of Conjugate 1 at 10 μg/kg (pink, solid squares), 75 μg/kg (purple, solid upwards triangles) or 150 μg/kg (orange, solid downwards-facing triangles) over time following administration of a single intravenous dose in rats as described in Example 24.

As shown in FIG. 40, Conjugate 1 exhibits sustained pharmacokinetics, measurable concentrations in plasma, with a half-life of approximately 18 hours as compared to plasma levels observed for non-long acting IL-15 following administration, which was rapidly cleared, shown in FIG. 40.

Example 25

In Vivo Study: Single Dose PK Study in Non-Human Primates

Cynomolgus monkeys (n=2, 1 male and 1 female), were administered a single intravenous dose of Conjugate 1 at 10, 50 and 100 µg/kg. IL-15 was administered as a single intravenous dose at 50 µg/kg as a control. Plasma concentration of drug was determined at the indicated time points post injection (0.03, 0.25, 1, 4, 12, 24, 48, 72, 96, 120, 144, 168 hours). See FIG. 41.

Figure 41:
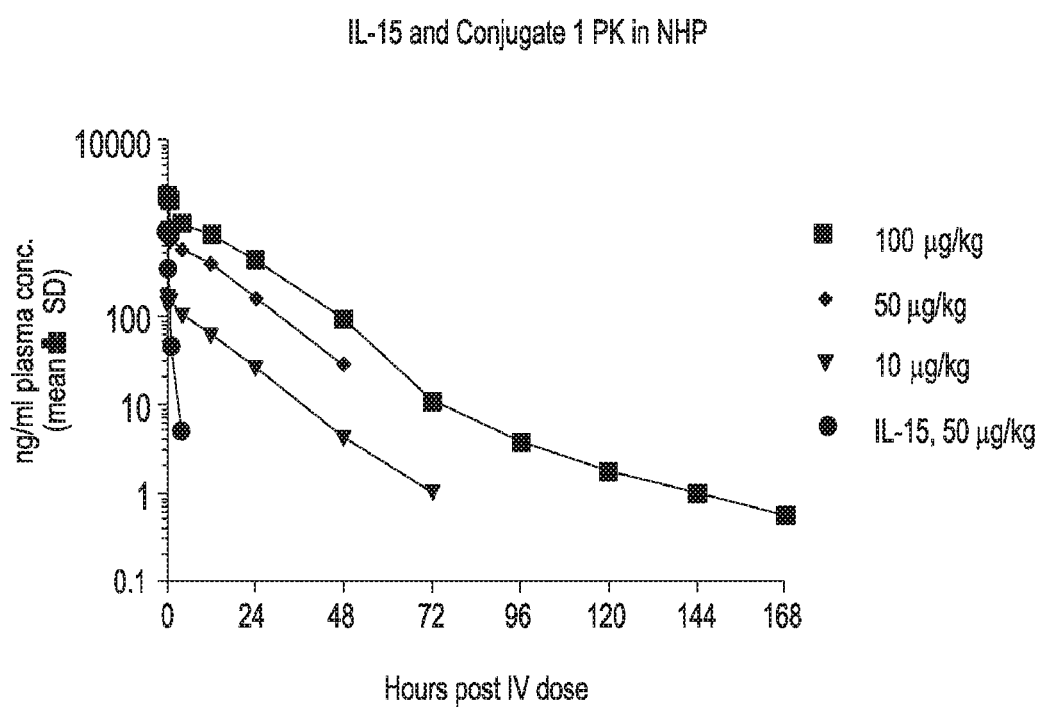
FIG. 41 is a plot of plasma concentration of IL-15 at 50 μg/kg (green, solid circles) or Conjugate 1 at 10 μg/kg (red, solid downwards facing triangles), 50 μg/kg (blue, solid diamonds) or 100 μg/kg (orange, solid squares) over time following administration of a single intravenous dose of test article in cynomolgus monkeys as described in Example 25.

As shown in FIG. 41, Conjugate 1 exhibits sustained pharmacokinetics, measurable concentrations in plasma, with a half-life of approximately 30 hours for the 100 µg/kg dose, as compared to non-long acting IL-15, which was rapidly cleared from the plasma.

Conjugate 1 achieved extended and sustained plasma exposure across multiple species (mice, rats and cynomolgus monkeys) after a single dose (see FIGS. 39-41).

Example 26

In Vivo Study: Single Dose PD Study in Mice—Cell Numbers, Proliferation and Engagement of JAK/STAT Signaling Balb/c mice (n=3/group) were administered a single intravenous dose of vehicle (as described in Example 11) or of Conjugate 1 at a dose of 0.3 mg/kg or 0.03 mg/kg. Following administration, blood samples were collected at time points after administration (24 hours, 48 hours, 72 hours, 96 hours, 120 hours, 144 hours and 240 hours). Samples were subjected to immunophenotyping for CD4 T cell numbers (see FIG. 42A) and % Ki-67 (see FIG. 42B) at the indicated time points.

Figure 42A:
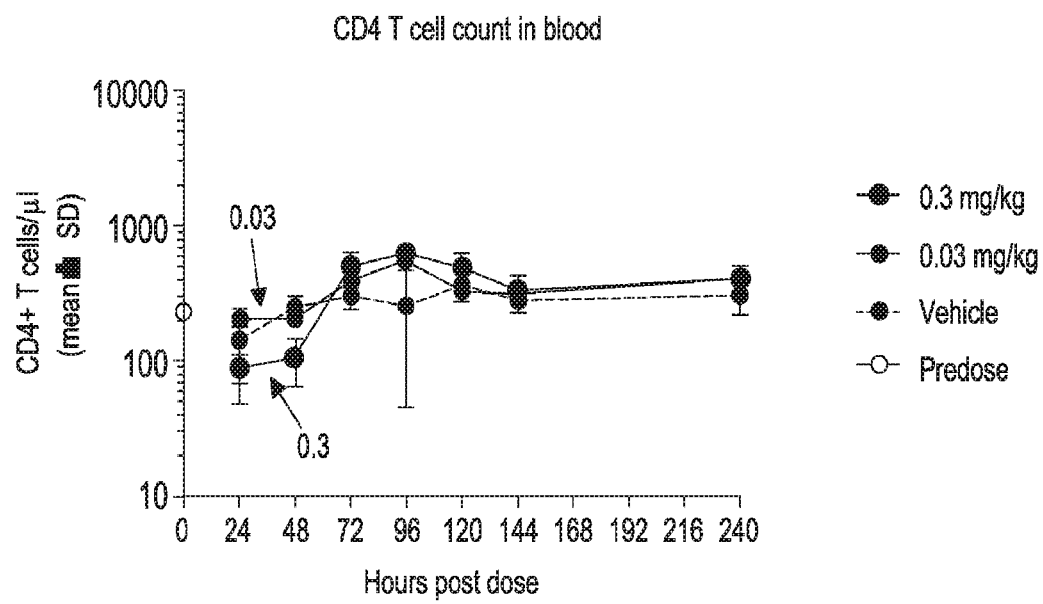
FIGS. 42A and 42B are plots of CD4 T cell numbers and Ki-67 percent positivity, respectively, after a single dose of Conjugate 1 at a dose of 0.03 mg/kg (blue, solid circles) or 0.3 mg/kg (orange, solid circles) in mice as described in Example 26. The vehicle (black) and pre-dose (open circles) cell levels are also shown. All dose levels returned to baseline by 240 hours post dose. The 0.3 mg/kg dose level induced a robust increase of Ki-67 percent positivity in CD4 T cells.
Figure 42B:
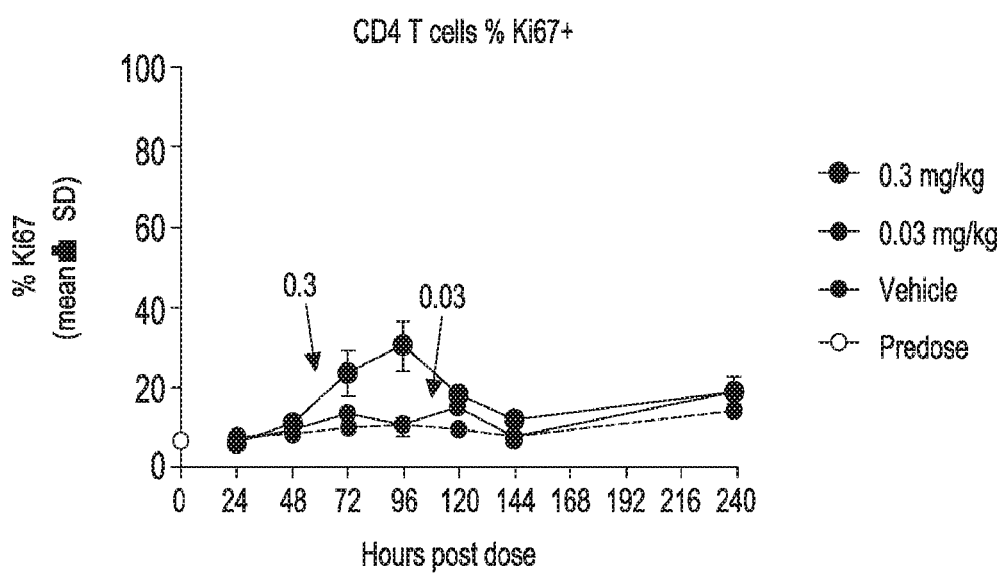

CD4 T cells and their proliferation were defined by CD45+CD3+CD4+CD8− and CD45+CD3+CD4+CD8-Ki-67+ markers, respectively. FIG. 42A is a plot of CD4 T cell numbers and FIG. 42B is a plot of CD4 T cell proliferation, measured by % Ki-67 positivity, over time. CD4 T cells were the least sensitive population to Conjugate 1 treatment with a relatively small increase in numbers and % Ki-67 expression (observed 72-144 hours post dose) compared to CD8 and NK cells (see, e.g., Example 11). NK cells were more sensitive to stimulation in proliferative responses by a single dose administration of Conjugate 1 than CD4 T cells or CD8 T cells in mice.

Figure 43:
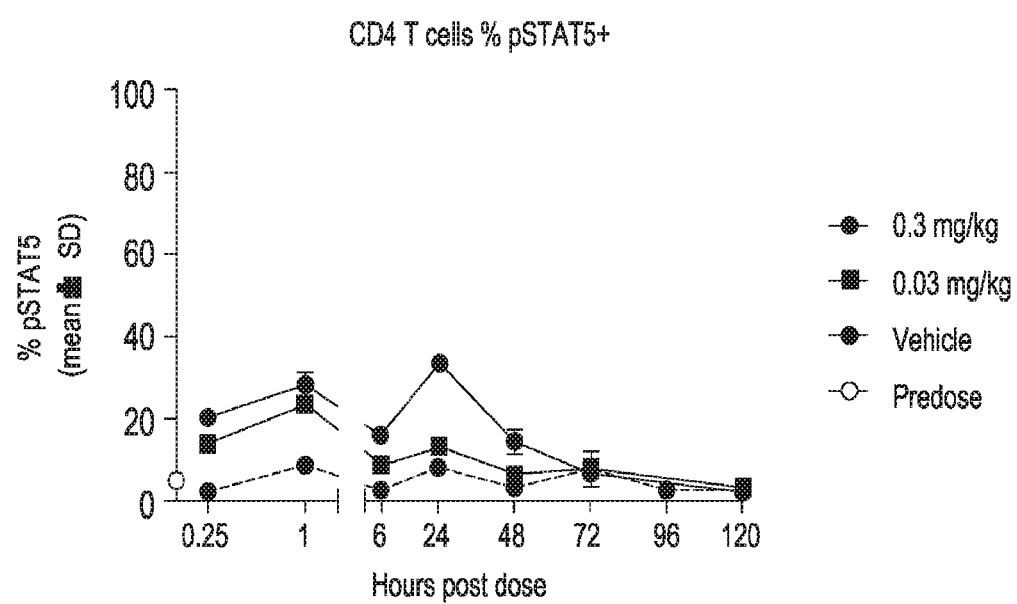
FIG. 43 is a graph of pSTAT5 percent positivity within CD4 T cells in mice after a single injection of Conjugate 1 at 0.03 mg/kg (orange, solid circles) or 0.3 mg/kg (blue, solid squares) as described in Example 26. Conjugate 1 at both dose levels induced increased pSTAT5 signaling in CD4 T cells, with the 0.3 mg/kg inducing a greater increase. A 120-hour time course, including vehicle (black) and pre-dose (open circles), are shown.

STAT5 phosphorylation in CD4 T cells was determined by using a CD3+CD4+CD8-pSTAT5+ marker combination. FIG. 43 is a plot of pSTAT5 phosphorylation percent positivity within CD4 T cells over time (at 0.25, 1, 6, 24, 48, 72, 96 and 120 hours post administration) at a dose of 0.03 mg/kg (blue, solid squares) or 0.3 mg/kg (orange, solid circles). The vehicle over time (black) and pre-dose (open circles) levels are also shown.

Results: CD4 T cells are the least sensitive population to Conjugate 1 treatment with relatively less increase in pSTAT5 expression (observed 0.25 to 72 hours post dose) as compared to CD8 and NK cells. NK cells are more sensitive to a single dose of Conjugate 1 stimulation in proliferative responses as compared to CD8 T cells or CD4 T cells in mice.

Example 27

In Vivo-Study: Minimum Efficacious Dose Study in Non-Human Primates (NHP)

Cynomolgus monkeys (n=3-4 males), were administered a single intravenous injection of Conjugate 1 at 0.003, 0.01, 0.1 mg/kg or a vehicle control. Blood samples were collected at the indicated time points pre and post dose (−5, −2, 1, 2, 3, 4, 5, 6, 7, 10, 14, 17 days) and subjected to flow cytometric analysis to examine pharmacodynamic effects within lymphocyte populations. Cell numbers of NK, CD8 T, and CD4 T cells were examined with the results shown in FIGS. 44A-C. Proliferation (% Ki-67) and JAK/STAT signaling (% pSTAT5) for NK cells, CD8 T cells, and CD4 T cells were examined, with the results shown in FIGS. 45A-C and FIGS. 46A-C, respectively. Proliferation (% Ki-67) of CD8 subpopulations ($T_{naive}$, $T_{em}$, $T_{cm}$ and $T_{scm}$) were examined with the results shown in FIGS. 47A-D.

In NHP, NK (CD45+CD3−CD16+) cell numbers increased substantially and in a dose-dependent manner after a single dose of Conjugate 1. Maximum cell numbers were observed five days after dosing and were sustained for up to 14 days at 0.1 and 0.01 mg/kg dose levels. The lowest dose level yielding a significant increase in NK cells was 0.01 mg/kg. Corroborating the observations in NK cell numbers, Conjugate 1 also drives a dose-dependent and robust induction of Ki-67 expression, which reaches a maximum approximately 3 to 4 days after treatment and can be sustained for up to about 14 days. A significant increase in % Ki-67 can be detected after the 0.001 mg/kg dose level. Conjugate 1 also robustly engages the JAK/STAT signaling pathway in NK cells, with a dose-dependent increase in % pSTAT5 that can be detected at a dose level as low as 0.001 mg/kg.

FIGS. 44A, 45A and 46A are plots of NK cell numbers, % Ki-67 and % pSTAT5 over time after Conjugate 1 treatment, respectively.

In NHP, Conjugate 1 induces a substantial increase in total CD8 T cells (defined as CD45+CD3+CD4−CD8+) with maximal cell numbers achieved around Day 5 after treatment. This effect is sustained for over seven days, returning to baseline between 10 to 14 days post dose. The effect of Conjugate 1 on the total CD8 cell numbers can be detected at 0.003 mg/kg. In support of these findings, Conjugate 1 induces abundant % Ki-67 positivity in CD8 T cells, detectable at a low dose of 0.01 mg/kg. Conjugate 1 engagement of the JAK/STAT signaling pathway is also robust in CD8 T cells with a dose-dependent increase in pSTAT5 at 0.1 and 0.01 mg/kg dose levels.

FIGS. 44B, 45B and 46B are plots of CD8 cell numbers, % Ki-67 and % pSTAT5, respectively, over time after Conjugate 1 treatment.

Conjugate 1 has a relatively small effect on total CD4 T cells (defined as CD45+CD3+CD4+CD8−) in NHP, compared to NK and CD8 T cells. Conjugate 1 dosed at the highest dose level of 0.1 mg/kg induced a small increase in CD4 T cell numbers, % Ki-67 and % pSTAT5.

FIGS. 44C, 45C and 46C are plots of CD4 T cell numbers, % Ki-67 and pSTAT5, respectively, over time after Conjugate 1 treatment.

NK cells are the most sensitive in Conjugate 1 dose response compared to CD8 T cells or CD4 T cells in vivo in NHP.

In cynomolgus monkey, CD8 naïve and memory subpopulations were defined by CD45Ra, CD197 and CD95. Examination of the proliferation (% Ki-67) of CD8 Tnaïve (CD45+CD3+CD4−CD8+CD45Ra+CD197+), CD8 Tscm (CD45+CD3+CD4−CD8+CD45Ra+CD197+CD95+), CD8 Tem (CD45+CD3+CD4−CD8+CD45Ra−CD197−) and CD8 Tcm (CD45+CD3+CD4−CD8+CD45Ra−CD197+) revealed increased sensitivity of CD8 memory subpopulations to Conjugate 1 compared to CD8 naïve T cells. Within the CD8 Tem, Tcm and Tscm populations, Conjugate 1 induced robust % Ki-67 expression in a dose dependent manner with detectable increases in proliferation marker positivity starting as early as day 2, reaching a maximum at day 5 and returning to baseline between days 10-14. The Ki-67 expression and kinetics within the CD8 populations support the sustained increase in CD8 T cell numbers shown in Example 27 and FIGS. 47A-D.

FIGS. 47A-D are plots of % Ki-67 of CD8 $T_{naïve}$, $T_{scm}$, $T_{cm}$ and $T_{em}$ populations over time after Conjugate 1 treatment. As seen in the figures, CD8 T cell memory populations showed increased sensitivity to a single dose of Conjugate 1 as compared to naïve CD8 T cells in vivo in NHPs.

Example 28

Induction of Granzyme B or Perforin by Conjugate 1

The expression of NK cytolytic enzymes, Granzyme B and Perforin, were examined in cynomolgus monkeys after a single dose of Conjugate 1. Expression levels of Granzyme B and Perforin were quantified by mean fluorescence intensity (MFI) within NK cells at 0.001 mg/kg, 0.01 mg/kg or 0.1 mg/kg dose levels. Conjugate 1 increased the MFI of Granzyme B by approximately 3-fold (peak versus pre-dose) at 0.01 and 0.1 mg/kg. Conjugate 1 also increased the MFI of Perforin approximately 2-fold (peak versus pre-dose) at 0.01 and 0.1 mg/kg. Altogether, Conjugate 1 not only induced robust expansion of NK cells, but can also enhance their function.

FIGS. 48A-C are plots of Granzyme B and FIGS. 49A-C are plots of Perforin MFI at pre-dose (baseline) and time of peak levels after Conjugate 1 treatment (0.0001-0.1 mg/kg) in NHP.

Conjugate 1 increases protein levels of cytotoxic enzymes, such as constitutively expressed Granzyme B and Perforin, in NHP NK cells.

---

SEQUENCE LISTING

```
SEQ ID NO: 1 (rhIL-15)
        10          20          30          40
NWVNVISDLK KIEDLIQSMH IDATLYTESD VHPSCKVTAM 50          60          70          80
KCFLLELQVI SLESGDASIH DTVENLIILA NNSLSSNGNV 90         100         110
TESGCKECEE LEEKNIKEFL QSFVHIVQMF INTS

SEQ ID NO: 2
 -1         10          20          30          40
  M NWVNVISDLK KIEDLIQSMH IDATLYTESD VHPSCKVTAM 50          60          70          80
KCFLLELQVI SLESGDASIH DTVENLIILA NNSLSSNGNV 90         100         110
TESGCKECEE LEEKNIKEFL QSFVHIVQMF INTS

SEQ ID NO: 3
        10          20          30          40
MRISKPHLRS ISIQCYLCLL LNSHFLTEAG IHVFILGCFS 50          60          70          80
AGLPKTEANW VNVISDLKKI EDLIQSMHID ATLYTESDVH 90         100         110         120
PSCKVTAMKC FLLELQVISL ESGDASIHDT VENLIILANN 130         140         150         160
SLSSNGNVTE SGCKECEELE EKNIKEFLQS FVHIVQMFIN TS
```

---

It is claimed:

1. A long-acting interleukin-15 (IL-15) receptor agonist composition comprising a mixture of poly(ethylene glycol)-interleukin-15 moiety conjugates according to Formula (I),

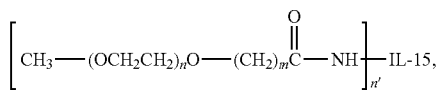

wherein n' is 1, and

Formula (II)

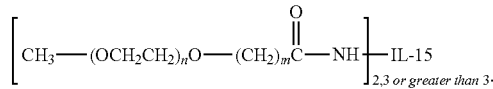

wherein with respect to each of Formula (I) and Formula (II), m is 3, IL-15 is an interleukin-15 moiety, n has a value corresponding to a weight average molecular weight of the poly(ethylene glycol) of about 40,000 daltons, and ~NH~ represents an amino group of the IL-15 moiety, wherein the average number of poly(ethylene glycol) moieties covalently attached to IL-15 amino groups for the conjugates of Formula (I) and Formula (II) comprised in the composition is in a range from 1.0 to about 1.3.

2. The long acting IL-15 receptor agonist composition of claim 1, comprising no more than about 15 mole percent of the IL-15 conjugates of Formula (II).

3. The long acting IL-15 receptor agonist composition of claim 2, comprising no more than about 10 mole percent of the IL-15 conjugates of Formula (II).

4. The long acting IL-15 receptor agonist composition of claim 2, comprising no more than about 7 mole percent of the IL-15 conjugates of Formula (II).

5. The long acting IL-15 receptor agonist composition of claim 2, comprising no more than about 5 mole percent of the IL-15 conjugates of Formula (II).

6. The long acting IL-15 receptor agonist composition of claim 1, wherein for the conjugates of Formula (I) and Formula (II) comprised in the composition, the average number of polyethylene glycol moieties covalently attached to IL-15 amino groups is selected from 1.0, 1.1, 1.2 and about 1.3.

7. The long acting IL-15 receptor agonist composition of claim 1, having an EC50 value (ng/mL, CTLL-2 pSTAT5) that, when compared to the EC50 value (ng/mL, CTLL-2 pSTAT5) of unmodified IL-15, is reduced by no more than about 2-fold.

8. The long acting IL-15 receptor agonist composition of claim 1, having a receptor alpha binding (KD, pM) value that is reduced by no more than about 50% when compared to IL-15.

9. The long acting IL-15 receptor agonist composition of claim 1, having a receptor alpha binding (KD, pM) value that is reduced by no more than about 45%, by no more than about 40%, by no more than about 35%, or by no more than about 30% when compared to the receptor alpha binding (KD, pM) value of unmodified IL-15.

10. The long acting IL-15 receptor agonist composition of claim 1, having an EC50 value (ng/mL, CTLL-2 pSTAT5) that is reduced by no more than about 2-fold when compared to the EC50 value of unmodified IL-15, and having a receptor alpha binding value (KD, pM) that is reduced by no more than about 50% when compared to the receptor alpha binding value (KD, pM) of unmodified IL-15.

11. The long acting IL-15 receptor agonist composition of claim 1, wherein the conjugates comprised in the composition are less than about 35% deamidated.

12. The long acting IL-15 receptor agonist composition of claim 1, comprising a mixture of positional isomers of the conjugates according to Formula (I).

13. The long acting IL-15 receptor agonist composition of claim 12, wherein for the mixture of positional isomers of Formula (I), the amino group is predominantly at the N-terminus of the IL-15 moiety.

14. The long acting IL-15 receptor agonist composition of claim 1, wherein the IL-15 moiety according to Formula (I) and Formula (II) is a recombinant human IL-15.

15. The long acting IL-15 receptor agonist composition of claim 1, wherein the IL-15 moiety according to Formula (I) and Formula (II) is unglycosylated.

16. The long acting IL-15 receptor agonist composition of claim 1, wherein the IL-15 moiety according to Formula (I) and Formula (II) has a sequence having at least about 90% identity to SEQ ID NO:1.

17. The long acting IL-15 receptor agonist composition of claim 1, wherein the IL-15 moiety according to Formula (I) and Formula (II) has a sequence having at least about 95% identity to SEQ ID NO:1.

18. The long acting IL-15 receptor agonist composition of claim 1, wherein the IL-15 moiety according to Formula (I) and Formula (II) has a sequence having at least about 99% identity to SEQ ID NO:1.

19. The long acting IL-15 receptor agonist composition of claim 1 comprised in a formulation for parenteral administration.

20. The long acting IL-15 receptor agonist composition of claim 1, further comprising at least one pharmaceutically acceptable excipient.

21. The long acting IL-15 receptor agonist composition of claim 20, wherein the pharmaceutically acceptable excipient is a buffer.

22. The long acting IL-15 receptor agonist of claim 21, wherein the buffer is potassium phosphate.

23. The long acting IL-15 receptor agonist composition of claim 20, wherein the pharmaceutically acceptable excipient is a carbohydrate.

24. The long acting IL-15 receptor agonist composition of claim 23, wherein the carbohydrate is trehalose.

25. The long acting IL-15 receptor agonist composition of claim 20, wherein the pharmaceutically acceptable excipient is a surfactant.

26. The long acting IL-15 receptor agonist composition of claim 25, wherein the surfactant is polysorbate 20.

27. The long acting IL-15 receptor agonist composition of claim 1, wherein the composition is comprised in an aqueous medium and has a pH of about 6.5 to 7.0.

28. The long acting IL-15 receptor agonist composition of claim 27, wherein the composition is comprised in an aqueous medium and has a pH of about 6.8.

\* \* \* \* \*